(12) United States Patent
Matsuzawa et al.

(10) Patent No.: US 7,833,972 B2
(45) Date of Patent: Nov. 16, 2010

(54) PROTEINS AND USE THEREOF

(75) Inventors: Yuji Matsuzawa, Takarazuka (JP); Tohru Funahashi, Suita (JP); Iichirou Shimomura, Toyonaka (JP); Naoki Furuyama, Kobe (JP)

(73) Assignee: Takeda Pharmaceutical Company Limited (JP)

( * ) Notice: Subject to any disclaimer, the term of this patent is extended or adjusted under 35 U.S.C. 154(b) by 0 days.

(21) Appl. No.: 12/371,525

(22) Filed: Feb. 13, 2009

(65) Prior Publication Data

US 2009/0203608 A1 Aug. 13, 2009

Related U.S. Application Data

(62) Division of application No. 10/520,783, filed as application No. PCT/JP03/08690 on Jul. 9, 2003, now abandoned.

(30) Foreign Application Priority Data

Jul. 10, 2002 (JP) ............................. 2002-201856

(51) Int. Cl.
*A61K 47/44* (2006.01)
*A61K 38/00* (2006.01)
(52) U.S. Cl. .............................. 514/2; 435/6; 435/7.21; 435/252.3; 435/326; 530/350; 536/23.1
(58) Field of Classification Search ........................ None
See application file for complete search history.

(56) References Cited

U.S. PATENT DOCUMENTS

| 7,189,807 | B2 | 3/2007 | Goddard et al. |
| 2002/0037540 | A1 | 3/2002 | Ali et al. |
| 2002/0197679 | A1 | 12/2002 | Tang et al. |
| 2003/0032155 | A1 | 2/2003 | Baker et al. |
| 2003/0040471 | A1 | 2/2003 | Watson et al. |

FOREIGN PATENT DOCUMENTS

| WO | WO 99/14328 | 3/1999 |
| WO | WO 00/53758 | 9/2000 |
| WO | WO 01/00638 | 1/2001 |
| WO | WO 01/48192 | 7/2001 |
| WO | WO 01/51636 | 7/2001 |
| WO | WO 01/57188 | 8/2001 |
| WO | WO 01/64835 | 9/2001 |
| WO | WO 02/22886 | A2 | 3/2002 |

OTHER PUBLICATIONS

Greeenbaum et al. (2003) Comparing protein abundance and mRNA expression levels on a genomic scale, Genome Biol., vol. 4, isssue 9, pp. 117.1-117.8.*
Dictionary (2010, updated) "represent", Encarta.msn.com/dictionary_/represented.html, pp. 1-3.*
Adachi et al., Riken functional annotation of a full-length mouse cDNA collection, Genbank, Jul. 10, 2000 Accession AK07787 & Apr. 16, 2002 Accession AK077118.
Adachi at al., Riken functional annotation of a full-length mouse cDNA collection, Genbank, Jul. 10, 2000 Accession AK09771, AK012437.
Adachi at al., Riken functional annotation of a full-length mouse cDNA collection, Genbank, Jul. 10, 2000 Accession AK17880.
Adachi at al., Riken functional annotation of a full-length mouse cDNA collection, Genbank, Jul. 16, 2001 Accession AK030584, AK0359 7 & Apr. 16, 2002 Accession AK082495, AK082963, AK080754.
Adachi at al., Riken functional annotation of a full-length mouse cDNA collection, Genbank, Jul. 16, 2001 Accession AK043006 & Apr. 16, 2002 Accession AK084668.
Arita et al., "Paradoxical decrease of an adipose-specific protein, adiponectin, in obesity," *Biochem. Biophys. Res. Common.*, 257(1): 79-83 (1999).
Baulande et al., "Adiponutrin, a transmembrane protein corresponding to a novel dietary- and obesity-linked mRNA specifically expressed in the adipose lineage," *J. Biol. Chem.*, 276(36): 3336-33344 (2001).
Bernlohr et al., "Fatty acid trafficking in the adipocyte," *Semin. Cell Dev. Biol.*, 10(1): 43-49 (1999).
Chen et al, "Discordant protein and mRNA expression in lung adenocarcinomas;" *Mol. Cell. Proteomics*, 1(4): 304-313 (2002).
Encarta Dictionary (2007, update), the term "represent," http://encarta.msn.com/dictionary_/represent.html, pp. 1-2.
EPO Communication of Mar. 6, 2007, regarding Application No. 03741288.9-2401, PCT/JP0308690.
Friedman et al., "Leptin and the regulation of body weight in mammals," *Nature*, 395(6704): 763-770 (1998).
Fujio et al., "Molecular cloning of a novel type 1 cytokine receptor similar to the common gamma chain," *Blood*, 95(7): 2204-2210 (2000).
Funahashi et al., "Role of adipocytokines on the pathogenesis of atherosclerosis in visceral obesity," *Intern. Med.*, 38(2): 202-206 (1999).
Gombart et al., "Mutations in the gene encoding the transcription factor CCAAT/enhancer binding protein alpha in myelodysplastic syndromes and acute myeloid leukemias," *Blood*, 99(4): 1332-1340 (2002).
Hu et al, "AdipoQ is a novel adipose-specific gene dysregulated in obesity," *J. Biol. Chem.*, 271(18): 10697-10703 (1996).
Kim et al., "A cysteine-rich adipose tissue-specific secretory factor inhibits adipocyte differentiation," *J. Biol. Chem.*, 276(14): 11252-11256 (2001).
Kishida et al., "Aquaporin adipose, a putative glycerol channel in adipocytes," *J. Biol. Chem.*, 275(27): 20896-20902 (2000).

(Continued)

*Primary Examiner*—Anand U Desai
*Assistant Examiner*—Samuel Liu
(74) *Attorney, Agent, or Firm*—Finnegan, Henderson, Farabow, Garrett & Dunner, LLP

(57) ABSTRACT

A method of suppressing the differentiation of an adipocite and/or lipid accumulation in an adipocyte, which comprises contacting the adipocyte with a protein comprising the amino acid sequence of SEQ ID NO: 2 or a salt thereof, or with a polynucleotide comprising a sense strand sequence encoding a protein comprising the amino acid sequence of SEQ ID NO: 2.

2 Claims, No Drawings

OTHER PUBLICATIONS

Kurtzhals et al., "Albumin binding of insulins acylated with fatty acids: characterization of the ligand-protein interaction and correlation between binding affinity and timing of the insulin effect in vivo," *Biochem. J.*, 312(Pt 3): 725-731 (1995).

Maeda et al., "Analysis of an expression profile of genes in the human adipose tissue," *Gene*, 190(2): 227-235 (1997).

NCBI Accession No. NM_172874 (mRNA sequence) (3 pages).

NCBI Sequence Revision History for 32526860, printed Aug. 11, 2008 (1 page).

Notice of Reasons for Refusal mailed Nov. 6, 2007, for Japanese Patent Application No. 2003/194658, including translation (14 pages).

Notice of Reasons for Refusal mailed Feb. 19, 2008, for Japanese Patent Application No. 2003/194658, including translation (12 pages).

Notice of Reasons for Refusal mailed May 13, 2008, for Japanese Patent Application No. 2003/194658, including translation (6 pages).

Orlicky et al, "Synthesis and accumulation of a receptor regulatory protein associated with lipid droplet accumulation in 3T3-L1 cells," *J. Lipid Res.*, 39(6): 1152-1161 (1998).

Ross et al., "Podocan, a Novel Small Leucine-rich Repeat. Protein Expressed in the Sclerotic Glomerular Lesion of Experimental HIV-associated Nephropathy," *J. Biol. Chem.*, 278(35): 33248-33255 (2003).

Satoh, "TNF-α," *Endocrinology & Diabetology*, 14(4): 347-352 (2002).

Scott et al., "Differential nucleocytoplasmic shuttling of beta-arrestins. Characterization of a leucine-rich nuclear export signal in beta-arrestin2," *J. Biol. Chem.*, 277(40): 37693-37701 (2002).

Shi et al., "Role of intracellular calcium in human adipocyte differentiation," *Physiol. Genomics*, 3(2): 75-82 (2000).

Shimizu-Hirota et al., "Functional characterization of podocan, a member of a new class in the small leucine-rich repeat protein family," *FEBS Letters*, 563: 69-74 (2004).

Shimomura et al., "Enhanced expression of PAI-1 in visceral fat: possible contributor to vascular disease in obesity," *Nature Medicine*, 2(7): 800-803 (1996).

Strausberg et al., Generation and initial analysis of more than 15,000 full-length human and mouse cDNA sequences, Genbank, May 1, 2002 Accession BC028869.

Strausberg et al., Riken Generation and initial analysis of more than 15,000 full-length human and mouse cDNA sequences, Genbank, Oct. 29, 2001 Accession BC016252.

Strausberg et al., Riken Generation and initial analysis of more than 15,000 full-length human and mouse cDNA sequences, Genbank, Sep. 4, 2001 Accession BC013497, Feb. 1, 2002 Accession BC022616 & Mar. 1, 2002 Accession BC024888.

Sugiyama et al., "A novel low-density lipoprotein receptor-related protein mediating cellular uptake of apolipoprotein E-enriched beta-VLDL in vitro," *Biochemistry*, 39(51): 15817-15825 (2000).

Tsuruga et al., "Identification of novel membrane and secreted proteins upregulated during adipocyte differentiation," *Biochem. Biophys. Res. Commun.*, 272(1): 293-297 (2000).

Yamauchi et al., "Cloning of adiponectin receptors that mediate antidiabetic metabolic effects," *Nature*, 423(6941): 762-769 (2003), and "Corrigendum," *Nature*, 431(7012): 1123 (2004).

* cited by examiner

SEQUENCE LISTING

<160> NUMBER OF SEQ ID NOS: 48

<210> SEQ ID NO 1
<211> LENGTH: 1836
<212> TYPE: DNA
<213> ORGANISM: Mus musculus
<220> FEATURE:
<221> NAME/KEY: CDS
<222> LOCATION: (1)..(1833)
<223> OTHER INFORMATION:

```
<220> FEATURE:
<221> NAME/KEY: sig_peptide
<222> LOCATION: (1)..(69)
<223> OTHER INFORMATION:
<220> FEATURE:
<221> NAME/KEY: mat_peptide
<222> LOCATION: (70)..()
<223> OTHER INFORMATION:
<220> FEATURE:
<221> NAME/KEY: misc_feature
<222> LOCATION: (798)..(798)
<223> OTHER INFORMATION: 'n' stands for unidentified base.

<400> SEQUENCE: 1 atg gct ggc agc agg ggc ctg cca ctc cta ctg ctg gtg ctt cag ctc      48
Met Ala Gly Ser Arg Gly Leu Pro Leu Leu Leu Leu Val Leu Gln Leu
        -20                 -15                 -10 ttc ctg ggc cct gtg ctg cct gtg agg gca cct gtg ttt ggc cga agt      96
Phe Leu Gly Pro Val Leu Pro Val Arg Ala Pro Val Phe Gly Arg Ser
 -5                  -1  1                   5 gac acc ccc acc ctg agc ccc gag gag aat gaa ttt gtg gag gaa gag     144
Asp Thr Pro Thr Leu Ser Pro Glu Glu Asn Glu Phe Val Glu Glu Glu
 10              15                  20                  25 aat cag cca gtg ctg gtt ctg agc tcc gag gag cca gag cct ggc cca     192
Asn Gln Pro Val Leu Val Leu Ser Ser Glu Glu Pro Glu Pro Gly Pro
             30                  35                  40 gcc act gtc gac tgt ccc cga gat tgt gcc tgt tcc cag gaa ggt gta     240
Ala Thr Val Asp Cys Pro Arg Asp Cys Ala Cys Ser Gln Glu Gly Val
             45                  50                  55 gtg gac tgt ggt ggc att gac ctg cgt gag ttt cca ggc gac ctg ccc     288
Val Asp Cys Gly Gly Ile Asp Leu Arg Glu Phe Pro Gly Asp Leu Pro
         60                  65                  70 gag cac acc aac cat ctc tcc ttg cag aac aac cag ctg gag aag atc     336
Glu His Thr Asn His Leu Ser Leu Gln Asn Asn Gln Leu Glu Lys Ile
     75                  80                  85 tac ccc gag gag ctg tcc cgg ctg cag cgg ctg gag acg ctg aac ctg     384
Tyr Pro Glu Glu Leu Ser Arg Leu Gln Arg Leu Glu Thr Leu Asn Leu
 90                  95                 100                 105 cag aac aac cgc ctg aca tcc cga ggg ctc cca gag gag gca ttt gag     432
Gln Asn Asn Arg Leu Thr Ser Arg Gly Leu Pro Glu Glu Ala Phe Glu
                 110                 115                 120 cat ctt act agc ctc aat tac ctg tac ctg gcc aac aac aag ctg aca     480
His Leu Thr Ser Leu Asn Tyr Leu Tyr Leu Ala Asn Asn Lys Leu Thr
                 125                 130                 135 ctg gca ccc cga ttc ctg cca aac gcc ctg atc agt gtg gac ttt gct     528
Leu Ala Pro Arg Phe Leu Pro Asn Ala Leu Ile Ser Val Asp Phe Ala
         140                 145                 150 gcc aat tat ctc act aag atc tat gga ctc acc ttt ggc caa aag cca     576
Ala Asn Tyr Leu Thr Lys Ile Tyr Gly Leu Thr Phe Gly Gln Lys Pro
     155                 160                 165 aat ctg agg tct gtg tac ctg cat aac aac aag cta gca gat gcc ggg     624
Asn Leu Arg Ser Val Tyr Leu His Asn Asn Lys Leu Ala Asp Ala Gly
 170                 175                 180                 185 ctg ccg gac cac atg ttc aat ggc tcc agc aac gtc gag atc cta atc     672
Leu Pro Asp His Met Phe Asn Gly Ser Ser Asn Val Glu Ile Leu Ile
                 190                 195                 200 ctg tcc agc aac ttc ctg cgc cat gtg ccc aag cac ctg cca ccc gct     720
Leu Ser Ser Asn Phe Leu Arg His Val Pro Lys His Leu Pro Pro Ala
                 205                 210                 215 ctg tac aag ctg cac ctc aag aac aat aag cta gag aag atc ccc cct     768
Leu Tyr Lys Leu His Leu Lys Asn Asn Lys Leu Glu Lys Ile Pro Pro
         220                 225                 230
```

| | | |
|---|---|---|
| ggg gcc ttc agt gag ctg agc aac cta cgn gaa ctc tac ctg cag aac<br>Gly Ala Phe Ser Glu Leu Ser Asn Leu Arg Glu Leu Tyr Leu Gln Asn<br>235                         240                         245 | | 816 |
| aac tac ctg acc gac gag ggt ctg gac aac gag acc ttc tgg aag ctg<br>Asn Tyr Leu Thr Asp Glu Gly Leu Asp Asn Glu Thr Phe Trp Lys Leu<br>250                         255                       260                     265 | | 864 |
| tcc agc ctg gag tac ctg gac ttg tcc agc acc aac ctg tcg agg gtc<br>Ser Ser Leu Glu Tyr Leu Asp Leu Ser Ser Thr Asn Leu Ser Arg Val<br>                     270                       275                     280 | | 912 |
| cca gcg ggt ctt ccc cgc agc ctg gtc ctg ctg cac ctg gag aaa aat<br>Pro Ala Gly Leu Pro Arg Ser Leu Val Leu Leu His Leu Glu Lys Asn<br>            285                      290                     295 | | 960 |
| gcc atc cag agc gta gaa gct gat gtg ctg aca ccc atc cgc aac ctg<br>Ala Ile Gln Ser Val Glu Ala Asp Val Leu Thr Pro Ile Arg Asn Leu<br>                 300                     305                     310 | | 1008 |
| gag tac ctg ctg cta cat agc aac cag ctg cag gcc aag ggt atc cac<br>Glu Tyr Leu Leu Leu His Ser Asn Gln Leu Gln Ala Lys Gly Ile His<br>            315                      320                     325 | | 1056 |
| cca ctg gcc ttc cag ggc ctc aag aag ctc cac aca gtg cat cta tac<br>Pro Leu Ala Phe Gln Gly Leu Lys Lys Leu His Thr Val His Leu Tyr<br>330                         335                       340                     345 | | 1104 |
| aac aac gcg ctg gaa cgt gtg ccc agc ggc ctg ccc cgc cga gtg cgc<br>Asn Asn Ala Leu Glu Arg Val Pro Ser Gly Leu Pro Arg Arg Val Arg<br>                 350                     355                     360 | | 1152 |
| acc ctc atg atc ctg cac aac cag att aca ggc ata ggc cgt gag gac<br>Thr Leu Met Ile Leu His Asn Gln Ile Thr Gly Ile Gly Arg Glu Asp<br>            365                      370                     375 | | 1200 |
| ttc gct acc acc tac ttc ctg gaa gag ctc aac ctc agc tac aac cgc<br>Phe Ala Thr Thr Tyr Phe Leu Glu Glu Leu Asn Leu Ser Tyr Asn Arg<br>                 380                     385                     390 | | 1248 |
| atc acc agc cca cag atg cac cga gat gcc ttc cgc aag cta cgc ctg<br>Ile Thr Ser Pro Gln Met His Arg Asp Ala Phe Arg Lys Leu Arg Leu<br>            395                      400                     405 | | 1296 |
| ctg cgt tca ctt gac ttg tct ggc aac cgt ctg caa aca ctg cct cca<br>Leu Arg Ser Leu Asp Leu Ser Gly Asn Arg Leu Gln Thr Leu Pro Pro<br>410                         415                       420                     425 | | 1344 |
| ggc ctg ccg aaa aac gta cac gtg ctc aag gtc aag cgg aat gag ctg<br>Gly Leu Pro Lys Asn Val His Val Leu Lys Val Lys Arg Asn Glu Leu<br>                 430                     435                     440 | | 1392 |
| gct gcc ctg gca cgt ggg gca cta gct ggc atg gcc cag ctt cgg gaa<br>Ala Ala Leu Ala Arg Gly Ala Leu Ala Gly Met Ala Gln Leu Arg Glu<br>                 445                     450                     455 | | 1440 |
| ctc tac ctc aca ggc aac cga ctg cga agc cgg gcc ctg gga ccc cgt<br>Leu Tyr Leu Thr Gly Asn Arg Leu Arg Ser Arg Ala Leu Gly Pro Arg<br>            460                      465                     470 | | 1488 |
| gcc tgg gtg gac ctt gct ggt ctg cag ctg ctg gac atc gct ggg aat<br>Ala Trp Val Asp Leu Ala Gly Leu Gln Leu Leu Asp Ile Ala Gly Asn<br>475                         480                       485 | | 1536 |
| cag ctc aca gag gtc cct gag ggg ctc ccc cca tct ctg gag tat ctg<br>Gln Leu Thr Glu Val Pro Glu Gly Leu Pro Pro Ser Leu Glu Tyr Leu<br>490                         495                       500                     505 | | 1584 |
| tac ctg cag aat aac aag att agt gcc gtt cct gcc aac gcc ttt gac<br>Tyr Leu Gln Asn Asn Lys Ile Ser Ala Val Pro Ala Asn Ala Phe Asp<br>                 510                     515                     520 | | 1632 |
| tcc act ccc aac ctt aag ggg atc ttt ctc agg ttc aac aag ctg gct<br>Ser Thr Pro Asn Leu Lys Gly Ile Phe Leu Arg Phe Asn Lys Leu Ala<br>            525                      530                     535 | | 1680 |
| gtg ggc tcc gtg gtg gaa agc gcc ttc cgg agg ctg aaa cac ctg cag<br>Val Gly Ser Val Val Glu Ser Ala Phe Arg Arg Leu Lys His Leu Gln<br>540                         545                       550 | | 1728 |

```
gtc ttg gac att gaa ggc aac ttt gag ttt ggt aat ggt tcc aag gac    1776
Val Leu Asp Ile Glu Gly Asn Phe Glu Phe Gly Asn Gly Ser Lys Asp
    555                 560                 565 aaa gat gag gaa gag gaa gag gag gaa gag gaa gat gag gaa gag        1824
Lys Asp Glu Glu Glu Glu Glu Glu Glu Glu Glu Asp Glu Glu Glu
570                 575                 580                 585 gaa act aga tag                                                    1836
Glu Thr Arg <210> SEQ ID NO 2
<211> LENGTH: 611
<212> TYPE: PRT
<213> ORGANISM: Mus musculus

<400> SEQUENCE: 2

Met Ala Gly Ser Arg Gly Leu Pro Leu Leu Leu Val Leu Gln Leu
            -20                 -15                 -10

Phe Leu Gly Pro Val Leu Pro Val Arg Ala Pro Val Phe Gly Arg Ser
        -5                  -1  1                   5

Asp Thr Pro Thr Leu Ser Pro Glu Glu Asn Glu Phe Val Glu Glu
10                  15                  20                  25

Asn Gln Pro Val Leu Val Leu Ser Ser Glu Glu Pro Glu Pro Gly Pro
                30                  35                  40

Ala Thr Val Asp Cys Pro Arg Asp Cys Ala Cys Ser Gln Glu Gly Val
                45                  50                  55

Val Asp Cys Gly Gly Ile Asp Leu Arg Glu Phe Pro Gly Asp Leu Pro
            60                  65                  70

Glu His Thr Asn His Leu Ser Leu Gln Asn Asn Gln Leu Glu Lys Ile
    75                  80                  85

Tyr Pro Glu Glu Leu Ser Arg Leu Gln Arg Leu Glu Thr Leu Asn Leu
90                  95                  100                 105

Gln Asn Asn Arg Leu Thr Ser Arg Gly Leu Pro Glu Glu Ala Phe Glu
                110                 115                 120

His Leu Thr Ser Leu Asn Tyr Leu Tyr Leu Ala Asn Asn Lys Leu Thr
            125                 130                 135

Leu Ala Pro Arg Phe Leu Pro Asn Ala Leu Ile Ser Val Asp Phe Ala
        140                 145                 150

Ala Asn Tyr Leu Thr Lys Ile Tyr Gly Leu Thr Phe Gly Gln Lys Pro
    155                 160                 165

Asn Leu Arg Ser Val Tyr Leu His Asn Asn Lys Leu Ala Asp Ala Gly
170                 175                 180                 185

Leu Pro Asp His Met Phe Asn Gly Ser Ser Asn Val Glu Ile Leu Ile
                190                 195                 200

Leu Ser Ser Asn Phe Leu Arg His Val Pro Lys His Leu Pro Pro Ala
            205                 210                 215

Leu Tyr Lys Leu His Leu Lys Asn Asn Lys Leu Glu Lys Ile Pro Pro
        220                 225                 230

Gly Ala Phe Ser Glu Leu Ser Asn Leu Arg Glu Leu Tyr Leu Gln Asn
    235                 240                 245

Asn Tyr Leu Thr Asp Glu Gly Leu Asp Asn Glu Thr Phe Trp Lys Leu
250                 255                 260                 265

Ser Ser Leu Glu Tyr Leu Asp Leu Ser Ser Thr Asn Leu Ser Arg Val
                270                 275                 280

Pro Ala Gly Leu Pro Arg Ser Leu Val Leu Leu His Leu Glu Lys Asn
            285                 290                 295
```

```
Ala Ile Gln Ser Val Glu Ala Asp Val Leu Thr Pro Ile Arg Asn Leu
            300                 305                 310
Glu Tyr Leu Leu Leu His Ser Asn Gln Leu Gln Ala Lys Gly Ile His
        315                 320                 325
Pro Leu Ala Phe Gln Gly Leu Lys Lys Leu His Thr Val His Leu Tyr
330                 335                 340                 345
Asn Asn Ala Leu Glu Arg Val Pro Ser Gly Leu Pro Arg Arg Val Arg
                350                 355                 360
Thr Leu Met Ile Leu His Asn Gln Ile Thr Gly Ile Gly Arg Glu Asp
            365                 370                 375
Phe Ala Thr Thr Tyr Phe Leu Glu Glu Leu Asn Leu Ser Tyr Asn Arg
        380                 385                 390
Ile Thr Ser Pro Gln Met His Arg Asp Ala Phe Arg Lys Leu Arg Leu
395                 400                 405
Leu Arg Ser Leu Asp Leu Ser Gly Asn Arg Leu Gln Thr Leu Pro Pro
410                 415                 420                 425
Gly Leu Pro Lys Asn Val His Val Leu Lys Val Lys Arg Asn Glu Leu
                430                 435                 440
Ala Ala Leu Ala Arg Gly Ala Leu Ala Gly Met Ala Gln Leu Arg Glu
            445                 450                 455
Leu Tyr Leu Thr Gly Asn Arg Leu Arg Ser Arg Ala Leu Gly Pro Arg
        460                 465                 470
Ala Trp Val Asp Leu Ala Gly Leu Gln Leu Leu Asp Ile Ala Gly Asn
475                 480                 485
Gln Leu Thr Glu Val Pro Glu Gly Leu Pro Pro Ser Leu Glu Tyr Leu
490                 495                 500                 505
Tyr Leu Gln Asn Asn Lys Ile Ser Ala Val Pro Ala Asn Ala Phe Asp
                510                 515                 520
Ser Thr Pro Asn Leu Lys Gly Ile Phe Leu Arg Phe Asn Lys Leu Ala
            525                 530                 535
Val Gly Ser Val Val Glu Ser Ala Phe Arg Arg Leu Lys His Leu Gln
        540                 545                 550
Val Leu Asp Ile Glu Gly Asn Phe Glu Phe Gly Asn Gly Ser Lys Asp
555                 560                 565
Lys Asp Glu Glu Glu Glu Glu Glu Glu Glu Asp Glu Glu Glu
570                 575                 580                 585
Glu Thr Arg

<210> SEQ ID NO 3
<211> LENGTH: 480
<212> TYPE: DNA
<213> ORGANISM: Mus musculus
<220> FEATURE:
<221> NAME/KEY: CDS
<222> LOCATION: (1)..(477)
<223> OTHER INFORMATION:
<220> FEATURE:
<221> NAME/KEY: sig_peptide
<222> LOCATION: (1)..(69)
<223> OTHER INFORMATION:
<220> FEATURE:
<221> NAME/KEY: mat_peptide
<222> LOCATION: (70)..()
<223> OTHER INFORMATION:

<400> SEQUENCE: 3 atg gct ggc agc agg ggc ctg cca ctc cta ctg ctg gtg ctt cag ctc      48
Met Ala Gly Ser Arg Gly Leu Pro Leu Leu Leu Leu Val Leu Gln Leu
```

```
                -20                 -15                 -10
ttc ctg ggc cct gtg ctg cct gtg agg gca cct gtg ttt ggc cga agt      96
Phe Leu Gly Pro Val Leu Pro Val Arg Ala Pro Val Phe Gly Arg Ser
         -5                  -1  1                   5 gac acc ccc acc ctg agc ccc gag gag aat gaa ttt gtg gag gaa gag     144
Asp Thr Pro Thr Leu Ser Pro Glu Glu Asn Glu Phe Val Glu Glu Glu
 10                  15                  20                  25 aat cag cca gtg ctg gtt ctg agc tcc gag gag cca gag cct ggc cca     192
Asn Gln Pro Val Leu Val Leu Ser Ser Glu Glu Pro Glu Pro Gly Pro
                 30                  35                  40 gcc act gtc gac tgt ccc cga gat tgt gcc tgt tcc cag gaa ggt gta     240
Ala Thr Val Asp Cys Pro Arg Asp Cys Ala Cys Ser Gln Glu Gly Val
             45                  50                  55 gtg gac tgt ggt ggc att gac ctg cgt gag ttt cca ggc gac ctg ccc     288
Val Asp Cys Gly Gly Ile Asp Leu Arg Glu Phe Pro Gly Asp Leu Pro
         60                  65                  70 gag cac acc aac cat ctc tcc ttg cag aac aac cag ctg gag aag atc     336
Glu His Thr Asn His Leu Ser Leu Gln Asn Asn Gln Leu Glu Lys Ile
 75                  80                  85 tac ccc gag gag ctg tcc cgg ctg cag cgg ctg gag acg ctg aac ctg     384
Tyr Pro Glu Glu Leu Ser Arg Leu Gln Arg Leu Glu Thr Leu Asn Leu
 90                  95                 100                 105 cag aac aac cgc ctg aca tcc cga gct gac act ggc acc ccg att cct     432
Gln Asn Asn Arg Leu Thr Ser Arg Ala Asp Thr Gly Thr Pro Ile Pro
                110                 115                 120 gcc aaa cgc cct gat cag tgt gga ctt tgc tgc caa tta tct cac taa     480
Ala Lys Arg Pro Asp Gln Cys Gly Leu Cys Cys Gln Leu Ser His
            125                 130                 135

<210> SEQ ID NO 4
<211> LENGTH: 159
<212> TYPE: PRT
<213> ORGANISM: Mus musculus

<400> SEQUENCE: 4

Met Ala Gly Ser Arg Gly Leu Pro Leu Leu Leu Val Leu Gln Leu
            -20                 -15                 -10

Phe Leu Gly Pro Val Leu Pro Val Arg Ala Pro Val Phe Gly Arg Ser
         -5                  -1  1                   5

Asp Thr Pro Thr Leu Ser Pro Glu Glu Asn Glu Phe Val Glu Glu Glu
 10                  15                  20                  25

Asn Gln Pro Val Leu Val Leu Ser Ser Glu Glu Pro Glu Pro Gly Pro
                 30                  35                  40

Ala Thr Val Asp Cys Pro Arg Asp Cys Ala Cys Ser Gln Glu Gly Val
             45                  50                  55

Val Asp Cys Gly Gly Ile Asp Leu Arg Glu Phe Pro Gly Asp Leu Pro
         60                  65                  70

Glu His Thr Asn His Leu Ser Leu Gln Asn Asn Gln Leu Glu Lys Ile
 75                  80                  85

Tyr Pro Glu Glu Leu Ser Arg Leu Gln Arg Leu Glu Thr Leu Asn Leu
 90                  95                 100                 105

Gln Asn Asn Arg Leu Thr Ser Arg Ala Asp Thr Gly Thr Pro Ile Pro
                110                 115                 120

Ala Lys Arg Pro Asp Gln Cys Gly Leu Cys Cys Gln Leu Ser His
            125                 130                 135

<210> SEQ ID NO 5
<211> LENGTH: 1092
```

```
<212> TYPE: DNA
<213> ORGANISM: Mus musculus
<220> FEATURE:
<221> NAME/KEY: CDS
<222> LOCATION: (1)..(1089)
<223> OTHER INFORMATION:
<220> FEATURE:
<221> NAME/KEY: sig_peptide
<222> LOCATION: (1)..(180)
<223> OTHER INFORMATION:
<220> FEATURE:
<221> NAME/KEY: mat_peptide
<222> LOCATION: (181)..()
<223> OTHER INFORMATION:

<400> SEQUENCE: 5
```

| | | | | | | | | | | | | | | | | |
|---|---|---|---|---|---|---|---|---|---|---|---|---|---|---|---|---|
| atg | gtg | ggt | tcc | tgt | ggt | cgc | tgc | gca | gcg | gct | ggc | cga | ctt | ccg | cag | 48 |
| Met | Val | Gly | Ser | Cys | Gly | Arg | Cys | Ala | Ala | Gly | Arg | Leu | Pro | Gln | |
| -60 | | | | -55 | | | | -50 | | | | -45 | | | | |
| cgg | gtc | tcg | ggc | cac | cga | gcg | ccg | tct | tca | ccc | agc | gcc | atg | gct | gtg | 96 |
| Arg | Val | Ser | Gly | His | Arg | Ala | Pro | Ser | Ser | Pro | Ser | Ala | Met | Ala | Val | |
| | | | -40 | | | | -35 | | | | | -30 | | | | |
| gcc | gct | gtc | ggc | cgc | ccg | aga | gcc | ctg | cgc | tgc | ccg | ctg | ttg | ctc | ctg | 144 |
| Ala | Ala | Val | Gly | Arg | Pro | Arg | Ala | Leu | Arg | Cys | Pro | Leu | Leu | Leu | Leu | |
| | -25 | | | | | -20 | | | | | -15 | | | | | |
| ctg | tca | ctc | ctg | ctg | gta | gcc | ggc | cct | gcg | ctg | ggc | tgg | aac | gac | cct | 192 |
| Leu | Ser | Leu | Leu | Leu | Val | Ala | Gly | Pro | Ala | Leu | Gly | Trp | Asn | Asp | Pro | |
| | -10 | | | | | -5 | | | | | -1 | 1 | | | | |
| gac | aga | ata | ctc | ttg | cgg | gat | gtg | aaa | gct | ctt | acc | ctc | tac | tcc | gac | 240 |
| Asp | Arg | Ile | Leu | Leu | Arg | Asp | Val | Lys | Ala | Leu | Thr | Leu | Tyr | Ser | Asp | |
| 5 | | | | 10 | | | | | 15 | | | | | 20 | | |
| cgc | tac | acc | acc | tcc | cgg | agg | ctg | gac | cct | atc | cca | cag | ttg | aag | tgt | 288 |
| Arg | Tyr | Thr | Thr | Ser | Arg | Arg | Leu | Asp | Pro | Ile | Pro | Gln | Leu | Lys | Cys | |
| | | | 25 | | | | | 30 | | | | | 35 | | | |
| gtt | gga | ggc | acc | gcc | ggt | tgt | gag | gcc | tat | acc | ccc | agg | gtg | ata | cag | 336 |
| Val | Gly | Gly | Thr | Ala | Gly | Cys | Glu | Ala | Tyr | Thr | Pro | Arg | Val | Ile | Gln | |
| | | 40 | | | | | 45 | | | | | 50 | | | | |
| tgc | cag | aac | aaa | ggc | tgg | gat | ggc | tac | gat | gta | cag | tgg | gaa | tgt | aag | 384 |
| Cys | Gln | Asn | Lys | Gly | Trp | Asp | Gly | Tyr | Asp | Val | Gln | Trp | Glu | Cys | Lys | |
| | 55 | | | | | 60 | | | | | 65 | | | | | |
| acc | gac | ttg | gat | att | gca | tac | aaa | ttt | ggc | aaa | act | gtg | gtg | agc | tgt | 432 |
| Thr | Asp | Leu | Asp | Ile | Ala | Tyr | Lys | Phe | Gly | Lys | Thr | Val | Val | Ser | Cys | |
| 70 | | | | | 75 | | | | | 80 | | | | | | |
| gaa | ggc | tac | gag | tcc | tct | gaa | gac | cag | tat | gtc | ctc | agg | ggt | tcc | tgc | 480 |
| Glu | Gly | Tyr | Glu | Ser | Ser | Glu | Asp | Gln | Tyr | Val | Leu | Arg | Gly | Ser | Cys | |
| 85 | | | | 90 | | | | | 95 | | | | | 100 | | |
| ggc | ttg | gag | tac | aac | tta | gat | tac | aca | gag | ctg | ggc | ctg | aag | aaa | ctg | 528 |
| Gly | Leu | Glu | Tyr | Asn | Leu | Asp | Tyr | Thr | Glu | Leu | Gly | Leu | Lys | Lys | Leu | |
| | | | | 105 | | | | | 110 | | | | | 115 | | |
| aag | gag | tct | gga | aag | cac | cag | ggc | ttc | tct | gat | tat | tat | cac | aag | ctg | 576 |
| Lys | Glu | Ser | Gly | Lys | His | Gln | Gly | Phe | Ser | Asp | Tyr | Tyr | His | Lys | Leu | |
| | | | 120 | | | | | 125 | | | | | 130 | | | |
| tgc | tcc | tca | gat | tcc | tgt | ggc | ttt | att | acc | att | gca | gta | ctg | ttt | gtt | 624 |
| Cys | Ser | Ser | Asp | Ser | Cys | Gly | Phe | Ile | Thr | Ile | Ala | Val | Leu | Phe | Val | |
| | | 135 | | | | | 140 | | | | | 145 | | | | |
| ctc | gcc | ttt | gcg | gtt | tac | aag | ctg | ttc | ctc | agc | gat | ggc | cag | ggg | tcg | 672 |
| Leu | Ala | Phe | Ala | Val | Tyr | Lys | Leu | Phe | Leu | Ser | Asp | Gly | Gln | Gly | Ser | |
| | 150 | | | | | 155 | | | | | 160 | | | | | |
| cct | ccg | ccg | tat | tct | gag | cac | ccg | cca | tac | tca | gag | cac | tct | cag | agg | 720 |
| Pro | Pro | Pro | Tyr | Ser | Glu | His | Pro | Pro | Tyr | Ser | Glu | His | Ser | Gln | Arg | |
| 165 | | | | | 170 | | | | | 175 | | | | | 180 | |
| ttt | gcc | agt | gcc | gca | ggg | gcg | cct | cct | ccg | ggc | ttt | aag | tcg | gag | ttc | 768 |
| Phe | Ala | Ser | Ala | Ala | Gly | Ala | Pro | Pro | Pro | Gly | Phe | Lys | Ser | Glu | Phe | |

```
aca gga cca cag aat act ggc tat ggt gca agc tct ggc ttc ggg agt      816
Thr Gly Pro Gln Asn Thr Gly Tyr Gly Ala Ser Ser Gly Phe Gly Ser
            200                 205                 210 gct ttt gga ggc caa ggc tat ggc agt tca ggg ccg ggg ttc tgg tct      864
Ala Phe Gly Gly Gln Gly Tyr Gly Ser Ser Gly Pro Gly Phe Trp Ser
        215                 220                 225 ggc ctg gga gct gga gga ctg ctt ggg tat ttg ttt ggc agc aac aga      912
Gly Leu Gly Ala Gly Gly Leu Leu Gly Tyr Leu Phe Gly Ser Asn Arg
    230                 235                 240 gcg gcg acg cct ttc tca gac tcg tgg tac cat cca gcc tac cct cct      960
Ala Ala Thr Pro Phe Ser Asp Ser Trp Tyr His Pro Ala Tyr Pro Pro
245                 250                 255                 260 tcc cac tct ggg gcc tgg aac agt cgg gcc tac tca ccc ctg ggt gga     1008
Ser His Ser Gly Ala Trp Asn Ser Arg Ala Tyr Ser Pro Leu Gly Gly
                265                 270                 275 ggc gca ggg agc tat tgt gca tcc tct aat gca gac tcg aga acc aga     1056
Gly Ala Gly Ser Tyr Cys Ala Ser Ser Asn Ala Asp Ser Arg Thr Arg
            280                 285                 290 aca gca tca gga tat ggt ggc acc aga aga cgg taa                     1092
Thr Ala Ser Gly Tyr Gly Gly Thr Arg Arg Arg
        295                 300

<210> SEQ ID NO 6
<211> LENGTH: 363
<212> TYPE: PRT
<213> ORGANISM: Mus musculus

<400> SEQUENCE: 6

Met Val Gly Ser Cys Gly Arg Cys Ala Ala Gly Arg Leu Pro Gln
-60                 -55                 -50                 -45

Arg Val Ser Gly His Arg Ala Pro Ser Ser Pro Ser Ala Met Ala Val
                -40                 -35                 -30

Ala Ala Val Gly Arg Pro Arg Ala Leu Arg Cys Pro Leu Leu Leu
            -25                 -20                 -15

Leu Ser Leu Leu Leu Val Ala Gly Pro Ala Leu Gly Trp Asn Asp Pro
        -10                 -5                  -1  1

Asp Arg Ile Leu Leu Arg Asp Val Lys Ala Leu Thr Leu Tyr Ser Asp
5                   10                  15                  20

Arg Tyr Thr Thr Ser Arg Arg Leu Asp Pro Ile Pro Gln Leu Lys Cys
                25                  30                  35

Val Gly Gly Thr Ala Gly Cys Glu Ala Tyr Thr Pro Arg Val Ile Gln
            40                  45                  50

Cys Gln Asn Lys Gly Trp Asp Gly Tyr Asp Val Gln Trp Glu Cys Lys
        55                  60                  65

Thr Asp Leu Asp Ile Ala Tyr Lys Phe Gly Lys Thr Val Ser Cys
    70                  75                  80

Glu Gly Tyr Glu Ser Ser Glu Asp Gln Tyr Val Leu Arg Gly Ser Cys
85                  90                  95                  100

Gly Leu Glu Tyr Asn Leu Asp Tyr Thr Glu Leu Gly Leu Lys Lys Leu
                105                 110                 115

Lys Glu Ser Gly Lys His Gln Gly Phe Ser Asp Tyr Tyr His Lys Leu
            120                 125                 130

Cys Ser Ser Asp Ser Cys Gly Phe Ile Thr Ile Ala Val Leu Phe Val
        135                 140                 145

Leu Ala Phe Ala Val Tyr Lys Leu Phe Leu Ser Asp Gly Gln Gly Ser
    150                 155                 160
```

```
Pro Pro Pro Tyr Ser Glu His Pro Pro Tyr Ser Glu His Ser Gln Arg
165                 170                 175                 180

Phe Ala Ser Ala Ala Gly Ala Pro Pro Gly Phe Lys Ser Glu Phe
            185                 190                 195

Thr Gly Pro Gln Asn Thr Gly Tyr Gly Ala Ser Ser Gly Phe Gly Ser
        200                 205                 210

Ala Phe Gly Gly Gln Gly Tyr Gly Ser Ser Gly Pro Gly Phe Trp Ser
            215                 220                 225

Gly Leu Gly Ala Gly Leu Leu Gly Tyr Leu Phe Gly Ser Asn Arg
    230                 235                 240

Ala Ala Thr Pro Phe Ser Asp Ser Trp Tyr His Pro Ala Tyr Pro Pro
245                 250                 255                 260

Ser His Ser Gly Ala Trp Asn Ser Arg Ala Tyr Ser Pro Leu Gly Gly
                265                 270                 275

Gly Ala Gly Ser Tyr Cys Ala Ser Ser Asn Ala Asp Ser Arg Thr Arg
            280                 285                 290

Thr Ala Ser Gly Tyr Gly Gly Thr Arg Arg Arg
        295                 300
```

<210> SEQ ID NO 7
<211> LENGTH: 1005
<212> TYPE: DNA
<213> ORGANISM: Mus musculus
<220> FEATURE:
<221> NAME/KEY: CDS
<222> LOCATION: (1)..(1002)
<223> OTHER INFORMATION:
<220> FEATURE:
<221> NAME/KEY: sig_peptide
<222> LOCATION: (1)..(93)
<223> OTHER INFORMATION:
<220> FEATURE:
<221> NAME/KEY: mat_peptide
<222> LOCATION: (94)..()
<223> OTHER INFORMATION:

<400> SEQUENCE: 7

```
atg gct gtg gcc gct gtc ggc cgc ccg aga gcc ctg cgc tgc ccg ctg        48
Met Ala Val Ala Ala Val Gly Arg Pro Arg Ala Leu Arg Cys Pro Leu
    -30                 -25                 -20 ttg ctc ctg ctg tca ctc ctg ctg gta gcc ggc cct gcg ctg ggc tgg        96
Leu Leu Leu Leu Ser Leu Leu Leu Val Ala Gly Pro Ala Leu Gly Trp
-15                 -10                  -5                  -1  1 aac gac cct gac aga ata ctc ttg cgg gat gtg aaa gct ctt acc ctc       144
Asn Asp Pro Asp Arg Ile Leu Leu Arg Asp Val Lys Ala Leu Thr Leu
                5                  10                  15 tac tcc gac cgc tac acc acc tcc cgg agg ctg gac cct atc cca cag       192
Tyr Ser Asp Arg Tyr Thr Thr Ser Arg Arg Leu Asp Pro Ile Pro Gln
            20                  25                  30 ttg aag tgt gtt gga ggc acc gcc ggt tgt gag gcc tat acc ccc agg       240
Leu Lys Cys Val Gly Gly Thr Ala Gly Cys Glu Ala Tyr Thr Pro Arg
35                  40                  45 gtg ata cag tgc cag aac aaa ggc tgg gat ggc tac gat gta cag tgg       288
Val Ile Gln Cys Gln Asn Lys Gly Trp Asp Gly Tyr Asp Val Gln Trp
50                  55                  60                  65 gaa tgt aag acc gac ttg gat att gca tac aaa ttt ggc aaa act gtg       336
Glu Cys Lys Thr Asp Leu Asp Ile Ala Tyr Lys Phe Gly Lys Thr Val
                70                  75                  80 gtg agc tgt gaa ggc tac gag tcc tct gaa gac cag tat gtc ctc agg       384
Val Ser Cys Glu Gly Tyr Glu Ser Ser Glu Asp Gln Tyr Val Leu Arg
            85                  90                  95
```

```
ggt tcc tgc ggc ttg gag tac aac tta gat tac aca gag ctg ggc ctg        432
Gly Ser Cys Gly Leu Glu Tyr Asn Leu Asp Tyr Thr Glu Leu Gly Leu
            100                 105                 110 aag aaa ctg aag gag tct gga aag cac cag ggc ttc tct gat tat tat        480
Lys Lys Leu Lys Glu Ser Gly Lys His Gln Gly Phe Ser Asp Tyr Tyr
    115                 120                 125 cac aag ctg tgc tcc tca gat tcc tgt ggc ttt att acc att gca gta        528
His Lys Leu Cys Ser Ser Asp Ser Cys Gly Phe Ile Thr Ile Ala Val
130                 135                 140                 145 ctg ttt gtt ctc gcc ttt gcg gtt tac aag ctg ttc ctc agc gat ggc        576
Leu Phe Val Leu Ala Phe Ala Val Tyr Lys Leu Phe Leu Ser Asp Gly
                150                 155                 160 cag ggg tcg cct ccg ccg tat tct gag cac ccg cca tac tca gag cac        624
Gln Gly Ser Pro Pro Pro Tyr Ser Glu His Pro Pro Tyr Ser Glu His
            165                 170                 175 tct cag agg ttt gcc agt gcc gca ggg gcg cct cct ccg ggc ttt aag        672
Ser Gln Arg Phe Ala Ser Ala Ala Gly Ala Pro Pro Pro Gly Phe Lys
        180                 185                 190 tcg gag ttc aca gga cca cag aat act ggc tat ggt gca agc tct ggc        720
Ser Glu Phe Thr Gly Pro Gln Asn Thr Gly Tyr Gly Ala Ser Ser Gly
    195                 200                 205 ttc ggg agt gct ttt gga ggc caa ggc tat ggc agt tca ggg ccg ggg        768
Phe Gly Ser Ala Phe Gly Gly Gln Gly Tyr Gly Ser Ser Gly Pro Gly
210                 215                 220                 225 ttc tgg tct ggc ctg gga gct gga gga ctg ctt ggg tat ttg ttt ggc        816
Phe Trp Ser Gly Leu Gly Ala Gly Gly Leu Leu Gly Tyr Leu Phe Gly
                230                 235                 240 agc aac aga gcg gcg acg cct ttc tca gac tcg tgg tac cat cca gcc        864
Ser Asn Arg Ala Ala Thr Pro Phe Ser Asp Ser Trp Tyr His Pro Ala
            245                 250                 255 tac cct cct tcc cac tct ggg gcc tgg aac agt cgg gcc tac tca ccc        912
Tyr Pro Pro Ser His Ser Gly Ala Trp Asn Ser Arg Ala Tyr Ser Pro
        260                 265                 270 ctg ggt gga ggc gca ggg agc tat tgt gca tcc tct aat gca gac tcg        960
Leu Gly Gly Gly Ala Gly Ser Tyr Cys Ala Ser Ser Asn Ala Asp Ser
    275                 280                 285 aga acc aga aca gca tca gga tat ggt ggc acc aga aga cgg taa           1005
Arg Thr Arg Thr Ala Ser Gly Tyr Gly Gly Thr Arg Arg Arg
290                 295                 300

<210> SEQ ID NO 8
<211> LENGTH: 334
<212> TYPE: PRT
<213> ORGANISM: Mus musculus

<400> SEQUENCE: 8

Met Ala Val Ala Ala Val Gly Arg Pro Arg Ala Leu Arg Cys Pro Leu
        -30                 -25                 -20

Leu Leu Leu Leu Ser Leu Leu Val Ala Gly Pro Ala Leu Gly Trp
-15                 -10                 -5                 -1  1

Asn Asp Pro Asp Arg Ile Leu Leu Arg Asp Val Lys Ala Leu Thr Leu
                5                   10                  15

Tyr Ser Asp Arg Tyr Thr Thr Ser Arg Arg Leu Asp Pro Ile Pro Gln
        20                  25                  30

Leu Lys Cys Val Gly Gly Thr Ala Gly Cys Glu Ala Tyr Thr Pro Arg
    35                  40                  45

Val Ile Gln Cys Gln Asn Lys Gly Trp Asp Gly Tyr Asp Val Gln Trp
50                  55                  60                  65
```

```
Glu Cys Lys Thr Asp Leu Asp Ile Ala Tyr Lys Phe Gly Lys Thr Val
                 70                  75                  80
Val Ser Cys Glu Gly Tyr Glu Ser Ser Glu Asp Gln Tyr Val Leu Arg
             85                  90                  95
Gly Ser Cys Gly Leu Glu Tyr Asn Leu Asp Tyr Thr Glu Leu Gly Leu
            100                 105                 110
Lys Lys Leu Lys Glu Ser Gly Lys His Gln Gly Phe Ser Asp Tyr Tyr
        115                 120                 125
His Lys Leu Cys Ser Ser Asp Ser Cys Gly Phe Ile Thr Ile Ala Val
130                 135                 140                 145
Leu Phe Val Leu Ala Phe Ala Val Tyr Lys Leu Phe Leu Ser Asp Gly
                150                 155                 160
Gln Gly Ser Pro Pro Tyr Ser Glu His Pro Tyr Ser Glu His
            165                 170                 175
Ser Gln Arg Phe Ala Ser Ala Ala Gly Ala Pro Pro Gly Phe Lys
            180                 185                 190
Ser Glu Phe Thr Gly Pro Gln Asn Thr Gly Tyr Gly Ala Ser Ser Gly
        195                 200                 205
Phe Gly Ser Ala Phe Gly Gly Gln Gly Tyr Gly Ser Ser Gly Pro Gly
210                 215                 220                 225
Phe Trp Ser Gly Leu Gly Ala Gly Gly Leu Leu Gly Tyr Leu Phe Gly
                230                 235                 240
Ser Asn Arg Ala Ala Thr Pro Phe Ser Asp Ser Trp Tyr His Pro Ala
            245                 250                 255
Tyr Pro Pro Ser His Ser Gly Ala Trp Asn Ser Arg Ala Tyr Ser Pro
            260                 265                 270
Leu Gly Gly Gly Ala Gly Ser Tyr Cys Ala Ser Ser Asn Ala Asp Ser
        275                 280                 285
Arg Thr Arg Thr Ala Ser Gly Tyr Gly Gly Thr Arg Arg
290                 295                 300

<210> SEQ ID NO 9
<211> LENGTH: 1053
<212> TYPE: DNA
<213> ORGANISM: Mus musculus
<220> FEATURE:
<221> NAME/KEY: CDS
<222> LOCATION: (1)..(1050)
<223> OTHER INFORMATION:
<220> FEATURE:
<221> NAME/KEY: sig_peptide
<222> LOCATION: (1)..(66)
<223> OTHER INFORMATION:
<220> FEATURE:
<221> NAME/KEY: mat_peptide
<222> LOCATION: (67)..()
<223> OTHER INFORMATION:

<400> SEQUENCE: 9 atg cac ctg ctg ctt gca gcc gcg ttc ggg ctg ctg ctg ctg ccg          48
Met His Leu Leu Leu Ala Ala Ala Phe Gly Leu Leu Leu Leu Pro
        -20                 -15                 -10 ccg ccc ggg gcc gta gcc tcc cgg aag ccg acg atg tgc cag aga tgc     96
Pro Pro Gly Ala Val Ala Ser Arg Lys Pro Thr Met Cys Gln Arg Cys
     -5              -1   1               5                  10 cgg acg ctg gtg gac aag ttc aac cag ggg atg gcc aac acg gcc agg    144
Arg Thr Leu Val Asp Lys Phe Asn Gln Gly Met Ala Asn Thr Ala Arg
                 15                  20                  25 aag aat ttc ggt ggc ggc aac acg gcg tgg gaa gag aag acg ctg tct    192
Lys Asn Phe Gly Gly Gly Asn Thr Ala Trp Glu Glu Lys Thr Leu Ser
```

-continued

```
                30                  35                  40
aag tac gaa ttc agt gag atc cgg ctt ctg gag atc atg gag ggt ctg     240
Lys Tyr Glu Phe Ser Glu Ile Arg Leu Leu Glu Ile Met Glu Gly Leu
            45                  50                  55 tgt gac agc agt gac ttt gag tgc aac caa ctc ttg gag cag cag gag     288
Cys Asp Ser Ser Asp Phe Glu Cys Asn Gln Leu Leu Glu Gln Gln Glu
 60                  65                  70 gag cag cta gag gct tgg tgg cag aca ctg aag aag gag cac ccc aac     336
Glu Gln Leu Glu Ala Trp Trp Gln Thr Leu Lys Lys Glu His Pro Asn
 75                  80                  85                  90 cta ttt gag tgg ttc tgt gta cac aca ctg aaa gcg tgc tgt ctt cca     384
Leu Phe Glu Trp Phe Cys Val His Thr Leu Lys Ala Cys Cys Leu Pro
                 95                 100                 105 ggc acc tac ggg cca gac tgt caa aag tgc cag ggt ggg tcc gag agg     432
Gly Thr Tyr Gly Pro Asp Cys Gln Lys Cys Gln Gly Gly Ser Glu Arg
             110                 115                 120 cct tgc agc gga aac ggc tat tgc agc gga gac ggc agc aga cag ggc     480
Pro Cys Ser Gly Asn Gly Tyr Cys Ser Gly Asp Gly Ser Arg Gln Gly
         125                 130                 135 gac ggg tcc tgc cag tgt cac aca ggc tac aag gga cca ctg tgt att     528
Asp Gly Ser Cys Gln Cys His Thr Gly Tyr Lys Gly Pro Leu Cys Ile
     140                 145                 150 gac tgc aca gac ggc ttc ttc agc ttg cag agg aac gag acc cac agc     576
Asp Cys Thr Asp Gly Phe Phe Ser Leu Gln Arg Asn Glu Thr His Ser
155                 160                 165                 170 atc tgc tca gcc tgt gat gag tct tgc aag acc tgc tct ggt cca agc     624
Ile Cys Ser Ala Cys Asp Glu Ser Cys Lys Thr Cys Ser Gly Pro Ser
                 175                 180                 185 aac aaa gac tgt atc cag tgt gaa gtg ggc tgg gca cgt gtg gag gat     672
Asn Lys Asp Cys Ile Gln Cys Glu Val Gly Trp Ala Arg Val Glu Asp
             190                 195                 200 gcc tgt gtg gat gtg gat gag tgt gca gca gag aca tct ccg tgc agc     720
Ala Cys Val Asp Val Asp Glu Cys Ala Ala Glu Thr Ser Pro Cys Ser
         205                 210                 215 gat ggc cag tac tgt gag aat gtc aac ggc tcg tac aca tgt gaa gac     768
Asp Gly Gln Tyr Cys Glu Asn Val Asn Gly Ser Tyr Thr Cys Glu Asp
     220                 225                 230 tgt gat tct acc tgc gtg ggc tgt aca gga aaa ggc cca gcc aac tgt     816
Cys Asp Ser Thr Cys Val Gly Cys Thr Gly Lys Gly Pro Ala Asn Cys
235                 240                 245                 250 aag gag tgt att gcc ggc tac acc aag gag agt gga cag tgc aca gat     864
Lys Glu Cys Ile Ala Gly Tyr Thr Lys Glu Ser Gly Gln Cys Thr Asp
                 255                 260                 265 ata gat gaa tgc tca cta gaa gaa aaa gcc tgt aag agg aaa aac gaa     912
Ile Asp Glu Cys Ser Leu Glu Glu Lys Ala Cys Lys Arg Lys Asn Glu
             270                 275                 280 aac tgc tac aat gtt ccg ggg agc ttc gtg tgc gtg tgt ccg gaa ggc     960
Asn Cys Tyr Asn Val Pro Gly Ser Phe Val Cys Val Cys Pro Glu Gly
         285                 290                 295 ttt gag gag aca gaa gac gct tgt gtg cag aca gca gaa ggc aaa gtc    1008
Phe Glu Glu Thr Glu Asp Ala Cys Val Gln Thr Ala Glu Gly Lys Val
     300                 305                 310 aca gag gaa aac ccc aca cag cca ccc tcc cgt gag gat ttg tga        1053
Thr Glu Glu Asn Pro Thr Gln Pro Pro Ser Arg Glu Asp Leu
315                 320                 325
```

<210> SEQ ID NO 10
<211> LENGTH: 350
<212> TYPE: PRT
<213> ORGANISM: Mus musculus

<400> SEQUENCE: 10

```
Met His Leu Leu Leu Ala Ala Ala Phe Gly Leu Leu Leu Leu Pro
    -20                 -15                 -10

Pro Pro Gly Ala Val Ala Ser Arg Lys Pro Thr Met Cys Gln Arg Cys
 -5              -1   1               5                      10

Arg Thr Leu Val Asp Lys Phe Asn Gln Gly Met Ala Asn Thr Ala Arg
                 15                  20                  25

Lys Asn Phe Gly Gly Gly Asn Thr Ala Trp Glu Glu Lys Thr Leu Ser
             30                  35                  40

Lys Tyr Glu Phe Ser Glu Ile Arg Leu Leu Glu Ile Met Glu Gly Leu
         45                  50                  55

Cys Asp Ser Ser Asp Phe Glu Cys Asn Gln Leu Leu Glu Gln Gln Glu
 60                  65                  70

Glu Gln Leu Glu Ala Trp Trp Gln Thr Leu Lys Lys Glu His Pro Asn
 75              80                  85                      90

Leu Phe Glu Trp Phe Cys Val His Thr Leu Lys Ala Cys Cys Leu Pro
                 95                 100                 105

Gly Thr Tyr Gly Pro Asp Cys Gln Lys Cys Gln Gly Ser Glu Arg
            110                 115                 120

Pro Cys Ser Gly Asn Gly Tyr Cys Ser Gly Asp Gly Ser Arg Gln Gly
            125                 130                 135

Asp Gly Ser Cys Gln Cys His Thr Gly Tyr Lys Gly Pro Leu Cys Ile
            140                 145                 150

Asp Cys Thr Asp Gly Phe Phe Ser Leu Gln Arg Asn Glu Thr His Ser
155                 160                 165                 170

Ile Cys Ser Ala Cys Asp Glu Ser Cys Lys Thr Cys Ser Gly Pro Ser
                175                 180                 185

Asn Lys Asp Cys Ile Gln Cys Glu Val Gly Trp Ala Arg Val Glu Asp
            190                 195                 200

Ala Cys Val Asp Val Asp Glu Cys Ala Ala Glu Thr Ser Pro Cys Ser
        205                 210                 215

Asp Gly Gln Tyr Cys Glu Asn Val Asn Gly Ser Tyr Thr Cys Glu Asp
    220                 225                 230

Cys Asp Ser Thr Cys Val Gly Cys Thr Gly Lys Gly Pro Ala Asn Cys
235                 240                 245                 250

Lys Glu Cys Ile Ala Gly Tyr Thr Lys Glu Ser Gly Gln Cys Thr Asp
                255                 260                 265

Ile Asp Glu Cys Ser Leu Glu Glu Lys Ala Cys Lys Arg Lys Asn Glu
            270                 275                 280

Asn Cys Tyr Asn Val Pro Gly Ser Phe Val Cys Val Cys Pro Glu Gly
        285                 290                 295

Phe Glu Glu Thr Glu Asp Ala Cys Val Gln Thr Ala Glu Gly Lys Val
    300                 305                 310

Thr Glu Glu Asn Pro Thr Gln Pro Pro Ser Arg Glu Asp Leu
315                 320                 325
```

<210> SEQ ID NO 11
<211> LENGTH: 1254
<212> TYPE: DNA
<213> ORGANISM: Mus musculus
<220> FEATURE:
<221> NAME/KEY: CDS
<222> LOCATION: (1)..(1251)
<223> OTHER INFORMATION:
<220> FEATURE:

<220> FEATURE:
<221> NAME/KEY: sig_peptide
<222> LOCATION: (1)..(99)
<223> OTHER INFORMATION:
<220> FEATURE:
<221> NAME/KEY: mat_peptide
<222> LOCATION: (100)..()
<223> OTHER INFORMATION:

<400> SEQUENCE: 11

```
atg ccc ccg cgc cca gga cgc ctc ctc cag ccg ctg gcc ggg ctg ccg        48
Met Pro Pro Arg Pro Gly Arg Leu Leu Gln Pro Leu Ala Gly Leu Pro
        -30                 -25                 -20 gcc ctg gcc acg ctc ctg ctg ctc ggg gcg cgc aaa ggc gcc cgg            96
Ala Leu Ala Thr Leu Leu Leu Leu Gly Ala Arg Lys Gly Ala Arg
    -15                 -10                  -5 gcc cag gag gtg gaa gcg gac agc ggg gtc gag cag gac ccg cac gcc       144
Ala Gln Glu Val Glu Ala Asp Ser Gly Val Glu Gln Asp Pro His Ala
 -1  1                   5                  10                  15 aag cac ctg tat acg gcc gac atg ttc acg cac ggg atc cag agc gcc       192
Lys His Leu Tyr Thr Ala Asp Met Phe Thr His Gly Ile Gln Ser Ala
                 20                  25                  30 gcg cac ttc gtc atg ttc ttc gcg ccc tgg tgt gga cac tgc cag cgg       240
Ala His Phe Val Met Phe Phe Ala Pro Trp Cys Gly His Cys Gln Arg
             35                  40                  45 ctg cag cca act tgg aat gac ctg gga gac aag tac aac agc atg gag       288
Leu Gln Pro Thr Trp Asn Asp Leu Gly Asp Lys Tyr Asn Ser Met Glu
         50                  55                  60 gat gcc aag gtc tac gtg gcc aaa gtg gac tgc acg gct gat tcc gac       336
Asp Ala Lys Val Tyr Val Ala Lys Val Asp Cys Thr Ala Asp Ser Asp
     65                  70                  75 gtg tgt tct gcc cag gga gtg cga gga tac ccc acc ctg aag ttt ttt       384
Val Cys Ser Ala Gln Gly Val Arg Gly Tyr Pro Thr Leu Lys Phe Phe
 80                  85                  90                  95 aag cct gga caa gaa gca gtg aag tac cag ggt cct aga gac ttt gaa       432
Lys Pro Gly Gln Glu Ala Val Lys Tyr Gln Gly Pro Arg Asp Phe Glu
                100                 105                 110 aca ctg gaa aac tgg atg ctg cag aca ctg aac gag gag cca gcc aca       480
Thr Leu Glu Asn Trp Met Leu Gln Thr Leu Asn Glu Glu Pro Ala Thr
            115                 120                 125 ccg gag ccg gaa gcg gaa cca ccc aga gcc cct gag ctc aaa cag ggg       528
Pro Glu Pro Glu Ala Glu Pro Pro Arg Ala Pro Glu Leu Lys Gln Gly
        130                 135                 140 ttg tat gag ctc tcg gcc aac aac ttt gag ctg cat gtt tct caa ggc       576
Leu Tyr Glu Leu Ser Ala Asn Asn Phe Glu Leu His Val Ser Gln Gly
    145                 150                 155 aac cac ttt atc aag ttc ttc gct ccg tgg tgc ggt cac tgc aaa gct       624
Asn His Phe Ile Lys Phe Phe Ala Pro Trp Cys Gly His Cys Lys Ala
160                 165                 170                 175 ctg gct cca acc tgg gag cag ctg gct ctg ggc ctt gaa cat tct gaa       672
Leu Ala Pro Thr Trp Glu Gln Leu Ala Leu Gly Leu Glu His Ser Glu
                180                 185                 190 acc gtc aag att ggc aag gtt gac tgc acg cag cac tac gct gtc tgc       720
Thr Val Lys Ile Gly Lys Val Asp Cys Thr Gln His Tyr Ala Val Cys
            195                 200                 205 tca gag cat cag gtc aga ggc tat cca act ctg ctc tgg ttt cga gat       768
Ser Glu His Gln Val Arg Gly Tyr Pro Thr Leu Leu Trp Phe Arg Asp
        210                 215                 220 ggc aag aag gtg gat cag tac aag gga aag cgg gac ttg gag tca ctg       816
Gly Lys Lys Val Asp Gln Tyr Lys Gly Lys Arg Asp Leu Glu Ser Leu
    225                 230                 235 aga gac tat gtg cag tcc cag ctg cag ggt tca gag gca gct ccg gag       864
```

```
Arg Asp Tyr Val Gln Ser Gln Leu Gln Gly Ser Glu Ala Ala Pro Glu
240                 245                 250                 255 act gtt gag ccg tca gag gcc cca gtg atg gct gct gag ccc acg ggt      912
Thr Val Glu Pro Ser Glu Ala Pro Val Met Ala Ala Glu Pro Thr Gly
                260                 265                 270 gac aag ggc act gtg ctg gca ctc acc gag aag agc ttc gag gac act      960
Asp Lys Gly Thr Val Leu Ala Leu Thr Glu Lys Ser Phe Glu Asp Thr
            275                 280                 285 att gca cag ggg ata acc ttc gtc aag ttc tat gct ccg tgg tgt ggc     1008
Ile Ala Gln Gly Ile Thr Phe Val Lys Phe Tyr Ala Pro Trp Cys Gly
        290                 295                 300 cac tgt aag aat ctg gct cct acc tgg gag gag ctc tct aaa aag gaa     1056
His Cys Lys Asn Leu Ala Pro Thr Trp Glu Glu Leu Ser Lys Lys Glu
    305                 310                 315 ttc cca ggc ttg tca gat gtc acc atc gca gaa gtg gac tgc acc gct     1104
Phe Pro Gly Leu Ser Asp Val Thr Ile Ala Glu Val Asp Cys Thr Ala
320                 325                 330                 335 gag cgc aat gtc tgc agc aag tac tcg gta cga ggt tat ccc acg ttg     1152
Glu Arg Asn Val Cys Ser Lys Tyr Ser Val Arg Gly Tyr Pro Thr Leu
                340                 345                 350 ccg ctt ttc cga gga ggt gaa aaa gtg gga gac cac aac gga ggt aga     1200
Pro Leu Phe Arg Gly Gly Glu Lys Val Gly Asp His Asn Gly Gly Arg
            355                 360                 365 gac ctc gac tcc tta cac agc ttt gtt ctg cgc cag gca aag gat gaa     1248
Asp Leu Asp Ser Leu His Ser Phe Val Leu Arg Gln Ala Lys Asp Glu
        370                 375                 380 cta tag                                                              1254
Leu

<210> SEQ ID NO 12
<211> LENGTH: 417
<212> TYPE: PRT
<213> ORGANISM: Mus musculus

<400> SEQUENCE: 12

Met Pro Pro Arg Pro Gly Arg Leu Leu Gln Pro Leu Ala Gly Leu Pro
            -30                 -25                 -20

Ala Leu Ala Thr Leu Leu Leu Leu Gly Ala Arg Lys Gly Ala Arg
        -15                 -10                  -5

Ala Gln Glu Val Glu Ala Asp Ser Gly Val Gln Asp Pro His Ala
 -1  1               5                  10                  15

Lys His Leu Tyr Thr Ala Asp Met Phe Thr His Gly Ile Gln Ser Ala
                20                  25                  30

Ala His Phe Val Met Phe Phe Ala Pro Trp Cys Gly His Cys Gln Arg
            35                  40                  45

Leu Gln Pro Thr Trp Asn Asp Leu Gly Asp Lys Tyr Asn Ser Met Glu
        50                  55                  60

Asp Ala Lys Val Tyr Val Ala Lys Val Asp Cys Thr Ala Asp Ser Asp
    65                  70                  75

Val Cys Ser Ala Gln Gly Val Arg Gly Tyr Pro Thr Leu Lys Phe Phe
80                  85                  90                  95

Lys Pro Gly Gln Glu Ala Val Lys Tyr Gln Gly Pro Arg Asp Phe Glu
                100                 105                 110

Thr Leu Glu Asn Trp Met Leu Gln Thr Leu Asn Glu Glu Pro Ala Thr
            115                 120                 125

Pro Glu Pro Glu Ala Glu Pro Pro Arg Ala Pro Glu Leu Lys Gln Gly
        130                 135                 140
```

-continued

```
Leu Tyr Glu Leu Ser Ala Asn Phe Glu Leu His Val Ser Gln Gly
    145                 150                 155

Asn His Phe Ile Lys Phe Phe Ala Pro Trp Cys Gly His Cys Lys Ala
160                 165                 170                 175

Leu Ala Pro Thr Trp Glu Gln Leu Ala Leu Gly Leu Glu His Ser Glu
                180                 185                 190

Thr Val Lys Ile Gly Lys Val Asp Cys Thr Gln His Tyr Ala Val Cys
                195                 200                 205

Ser Glu His Gln Val Arg Gly Tyr Pro Thr Leu Leu Trp Phe Arg Asp
                210                 215                 220

Gly Lys Lys Val Asp Gln Tyr Lys Gly Lys Arg Asp Leu Glu Ser Leu
    225                 230                 235

Arg Asp Tyr Val Gln Ser Gln Leu Gln Gly Ser Glu Ala Ala Pro Glu
240                 245                 250                 255

Thr Val Glu Pro Ser Glu Ala Pro Val Met Ala Ala Glu Pro Thr Gly
                260                 265                 270

Asp Lys Gly Thr Val Leu Ala Leu Thr Glu Lys Ser Phe Glu Asp Thr
                275                 280                 285

Ile Ala Gln Gly Ile Thr Phe Val Lys Phe Tyr Ala Pro Trp Cys Gly
                290                 295                 300

His Cys Lys Asn Leu Ala Pro Thr Trp Glu Glu Leu Ser Lys Lys Glu
    305                 310                 315

Phe Pro Gly Leu Ser Asp Val Thr Ile Ala Glu Val Asp Cys Thr Ala
320                 325                 330                 335

Glu Arg Asn Val Cys Ser Lys Tyr Ser Val Arg Gly Tyr Pro Thr Leu
                340                 345                 350

Pro Leu Phe Arg Gly Gly Glu Lys Val Gly Asp His Asn Gly Gly Arg
                355                 360                 365

Asp Leu Asp Ser Leu His Ser Phe Val Leu Arg Gln Ala Lys Asp Glu
                370                 375                 380

Leu
```

```
<210> SEQ ID NO 13
<211> LENGTH: 843
<212> TYPE: DNA
<213> ORGANISM: Mus musculus
<220> FEATURE:
<221> NAME/KEY: CDS
<222> LOCATION: (1)..(840)
<223> OTHER INFORMATION:
<220> FEATURE:
<221> NAME/KEY: sig_peptide
<222> LOCATION: (1)..(99)
<223> OTHER INFORMATION:
<220> FEATURE:
<221> NAME/KEY: mat_peptide
<222> LOCATION: (100)..()
<223> OTHER INFORMATION:

<400> SEQUENCE: 13
```

```
atg ccc ccg cgc cca gga cgc ctc ctc cag ccg ctg gcc ggg ctg ccg      48
Met Pro Pro Arg Pro Gly Arg Leu Leu Gln Pro Leu Ala Gly Leu Pro
            -30                 -25                 -20 gcc ctg gcc acg ctc ctg ctg ctg ctc ggg gcg cgc aaa ggc gcc cgg      96
Ala Leu Ala Thr Leu Leu Leu Leu Leu Gly Ala Arg Lys Gly Ala Arg
        -15                 -10                  -5 gcc cag gag gtg gaa gcg gac agc ggg gtc gag cag gac ccg cac gcc     144
Ala Gln Glu Val Glu Ala Asp Ser Gly Val Glu Gln Asp Pro His Ala
 -1   1               5                  10                  15
```

-continued

| | |
|---|---|
| aag cac ctg tat acg gcc gac atg ttc acg cac ggg atc cag agc gcc<br>Lys His Leu Tyr Thr Ala Asp Met Phe Thr His Gly Ile Gln Ser Ala<br>20              25              30 | 192 |
| gcg cac ttc gtc atg ttc ttc gcg ccc tgg tgt gga cac tgc cag cgg<br>Ala His Phe Val Met Phe Phe Ala Pro Trp Cys Gly His Cys Gln Arg<br>35              40              45 | 240 |
| ctg cag cca act tgg aat gac ctg gga gac aag tac aac agc atg gag<br>Leu Gln Pro Thr Trp Asn Asp Leu Gly Asp Lys Tyr Asn Ser Met Glu<br>50              55              60 | 288 |
| gat gcc aag gtc tac gtg gcc aaa gtg gac tgc acg gct gat tcc gac<br>Asp Ala Lys Val Tyr Val Ala Lys Val Asp Cys Thr Ala Asp Ser Asp<br>65              70              75 | 336 |
| gtg tgc tct gcc cag gga gtg cga gga tac ccc acc ctg aag ttt ttt<br>Val Cys Ser Ala Gln Gly Val Arg Gly Tyr Pro Thr Leu Lys Phe Phe<br>80              85              90              95 | 384 |
| aag cct gga caa gaa gca gtg aag tac cag ggt cct aga gac ttt gaa<br>Lys Pro Gly Gln Glu Ala Val Lys Tyr Gln Gly Pro Arg Asp Phe Glu<br>100             105             110 | 432 |
| aca ctg gaa aac tgg atg ctg cag aca ctg aac gag gag cca gcc aca<br>Thr Leu Glu Asn Trp Met Leu Gln Thr Leu Asn Glu Glu Pro Ala Thr<br>115             120             125 | 480 |
| ccg gag ccg gaa gcg gaa cca ccc aga gcc cct gag ctc aaa cag ggg<br>Pro Glu Pro Glu Ala Glu Pro Pro Arg Ala Pro Glu Leu Lys Gln Gly<br>130             135             140 | 528 |
| ttg tat gag ctc tcg gcc aac aac ttt gag ctg cat gtt tct caa ggc<br>Leu Tyr Glu Leu Ser Ala Asn Asn Phe Glu Leu His Val Ser Gln Gly<br>145             150             155 | 576 |
| aac cac ttt atc aag ttc ttc gct ccg tgg tgc ggt cac tgc aaa gct<br>Asn His Phe Ile Lys Phe Phe Ala Pro Trp Cys Gly His Cys Lys Ala<br>160             165             170             175 | 624 |
| ctg gct cca acc tgg gag cag ctg gct ctg ggc ctt gaa cat tct gaa<br>Leu Ala Pro Thr Trp Glu Gln Leu Ala Leu Gly Leu Glu His Ser Glu<br>180             185             190 | 672 |
| acc gtc aag att ggc aag gtt gac tgc acg cag cac tac gct gtc tgc<br>Thr Val Lys Ile Gly Lys Val Asp Cys Thr Gln His Tyr Ala Val Cys<br>195             200             205 | 720 |
| tca gag cat cag gtc aga ggc tat cca act ctg ctc tgg ttt cga gat<br>Ser Glu His Gln Val Arg Gly Tyr Pro Thr Leu Leu Trp Phe Arg Asp<br>210             215             220 | 768 |
| ggc aag aag gtg gat cag tac aag gga aag cgg gac ttg gag tca ctg<br>Gly Lys Lys Val Asp Gln Tyr Lys Gly Lys Arg Asp Leu Glu Ser Leu<br>225             230             235 | 816 |
| aga gac tat gtg cag tcc cag ctg tag<br>Arg Asp Tyr Val Gln Ser Gln Leu<br>240             245 | 843 |

<210> SEQ ID NO 14
<211> LENGTH: 280
<212> TYPE: PRT
<213> ORGANISM: Mus musculus

<400> SEQUENCE: 14

Met Pro Pro Arg Pro Gly Arg Leu Leu Gln Pro Leu Ala Gly Leu Pro
              -30             -25             -20

Ala Leu Ala Thr Leu Leu Leu Leu Gly Ala Arg Lys Gly Ala Arg
        -15             -10             -5

Ala Gln Glu Val Glu Ala Asp Ser Gly Val Glu Gln Asp Pro His Ala
-1  1               5               10              15

Lys His Leu Tyr Thr Ala Asp Met Phe Thr His Gly Ile Gln Ser Ala
                20              25              30

```
Ala His Phe Val Met Phe Phe Ala Pro Trp Cys Gly His Cys Gln Arg
            35                  40                  45

Leu Gln Pro Thr Trp Asn Asp Leu Gly Asp Lys Tyr Asn Ser Met Glu
            50                  55                  60

Asp Ala Lys Val Tyr Val Ala Lys Val Asp Cys Thr Ala Asp Ser Asp
            65                  70                  75

Val Cys Ser Ala Gln Gly Val Arg Gly Tyr Pro Thr Leu Lys Phe Phe
80                  85                  90                  95

Lys Pro Gly Gln Glu Ala Val Lys Tyr Gln Gly Pro Arg Asp Phe Glu
                100                 105                 110

Thr Leu Glu Asn Trp Met Leu Gln Thr Leu Asn Glu Glu Pro Ala Thr
                115                 120                 125

Pro Glu Pro Glu Ala Glu Pro Pro Arg Ala Pro Glu Leu Lys Gln Gly
                130                 135                 140

Leu Tyr Glu Leu Ser Ala Asn Asn Phe Glu Leu His Val Ser Gln Gly
                145                 150                 155

Asn His Phe Ile Lys Phe Phe Ala Pro Trp Cys Gly His Cys Lys Ala
160                 165                 170                 175

Leu Ala Pro Thr Trp Glu Gln Leu Ala Leu Gly Leu Glu His Ser Glu
                180                 185                 190

Thr Val Lys Ile Gly Lys Val Asp Cys Thr Gln His Tyr Ala Val Cys
                195                 200                 205

Ser Glu His Gln Val Arg Gly Tyr Pro Thr Leu Leu Trp Phe Arg Asp
                210                 215                 220

Gly Lys Lys Val Asp Gln Tyr Lys Gly Lys Arg Asp Leu Glu Ser Leu
                225                 230                 235

Arg Asp Tyr Val Gln Ser Gln Leu
240                 245

<210> SEQ ID NO 15
<211> LENGTH: 1269
<212> TYPE: DNA
<213> ORGANISM: Mus musculus
<220> FEATURE:
<221> NAME/KEY: CDS
<222> LOCATION: (1)..(1266)
<223> OTHER INFORMATION:
<220> FEATURE:
<221> NAME/KEY: sig_peptide
<222> LOCATION: (1)..(63)
<223> OTHER INFORMATION:
<220> FEATURE:
<221> NAME/KEY: mat_peptide
<222> LOCATION: (64)..()
<223> OTHER INFORMATION:

<400> SEQUENCE: 15 atg cgt gcg ggc cgg tgt gcc gcg gcg ctg ctg ctg cta ctg agc        48
Met Arg Ala Gly Arg Cys Ala Ala Ala Leu Leu Leu Leu Leu Leu Ser
        -20                 -15                 -10 ggc gcg ggg cgc gcg atc ggc tcc gag gac atc gtg gta ggc tgc ggg    96
Gly Ala Gly Arg Ala Ile Gly Ser Glu Asp Ile Val Val Gly Cys Gly
 -5                  -1   1                   5                  10 ggt ttc gtg aag tcg gac gtg gag atc aac tac tcg ctc atc gag ata   144
Gly Phe Val Lys Ser Asp Val Glu Ile Asn Tyr Ser Leu Ile Glu Ile
                 15                  20                  25 aag tta tac acc aag cat ggg act ttg aaa tat cag acg gac tgt gct   192
Lys Leu Tyr Thr Lys His Gly Thr Leu Lys Tyr Gln Thr Asp Cys Ala
             30                  35                  40
```

| | |
|---|---:|
| cct aac aac ggc tac ttt atg atc ccc ttg tat gat aag ggg gat ttc<br>Pro Asn Asn Gly Tyr Phe Met Ile Pro Leu Tyr Asp Lys Gly Asp Phe<br>45                    50                    55 | 240 |
| atc ctg aag atc gaa cct cct ctg ggc tgg agt ttt gag cca acc aac<br>Ile Leu Lys Ile Glu Pro Pro Leu Gly Trp Ser Phe Glu Pro Thr Asn<br>60                    65                    70                    75 | 288 |
| gtg gag ctg cga gtg gat ggt gtg agc gac atc tgc acg aag ggc ggg<br>Val Glu Leu Arg Val Asp Gly Val Ser Asp Ile Cys Thr Lys Gly Gly<br>                  80                    85                    90 | 336 |
| gac atc aac ttc ctg ttc acc ggc ttc tct gtg aat ggc aag gtc ctc<br>Asp Ile Asn Phe Leu Phe Thr Gly Phe Ser Val Asn Gly Lys Val Leu<br>              95                    100                  105 | 384 |
| agc aaa ggg cag ccc ctg ggc cca gca gga gtt cag gta tcc ctg aga<br>Ser Lys Gly Gln Pro Leu Gly Pro Ala Gly Val Gln Val Ser Leu Arg<br>          110                    115                  120 | 432 |
| agc acc ggt gct gac tcg aag atc cag tct aca gtc acg cag cct ggc<br>Ser Thr Gly Ala Asp Ser Lys Ile Gln Ser Thr Val Thr Gln Pro Gly<br>          125                    130                  135 | 480 |
| gga aag ttt gcg ttt ttc aaa gtt ctt cct gga gat tat gaa atc ctt<br>Gly Lys Phe Ala Phe Phe Lys Val Leu Pro Gly Asp Tyr Glu Ile Leu<br>140                    145                    150                  155 | 528 |
| gca act cac ccg acc tgg gcg ctg aag gag gca agt acc acg gtg cgt<br>Ala Thr His Pro Thr Trp Ala Leu Lys Glu Ala Ser Thr Thr Val Arg<br>                  160                    165                  170 | 576 |
| gtg acg aac tcg aat gct aac gca gct ggt ccc ctc ata gtg gct ggc<br>Val Thr Asn Ser Asn Ala Asn Ala Ala Gly Pro Leu Ile Val Ala Gly<br>          175                    180                  185 | 624 |
| tat aat gtg tcc ggc tct gtc cgc agt gac ggg gag ccc atg aaa ggg<br>Tyr Asn Val Ser Gly Ser Val Arg Ser Asp Gly Glu Pro Met Lys Gly<br>                  190                    195                  200 | 672 |
| gtg aag ttt ctt ctc ttt tct tct tta gtg aac aaa gag gat gtc ctg<br>Val Lys Phe Leu Leu Phe Ser Ser Leu Val Asn Lys Glu Asp Val Leu<br>205                    210                    215 | 720 |
| ggc tgc aat gtg tcc cca gtg tcc ggg ttc cag ccc cca gat gag agc<br>Gly Cys Asn Val Ser Pro Val Ser Gly Phe Gln Pro Pro Asp Glu Ser<br>220                    225                    230                  235 | 768 |
| ctg gtt tat ctg tgc tat gcg gtc tcc aaa gaa gac ggc cca ttt tct<br>Leu Val Tyr Leu Cys Tyr Ala Val Ser Lys Glu Asp Gly Pro Phe Ser<br>                  240                    245                  250 | 816 |
| ttc tat tcc ttg ccg agt ggg ggc tac act gtg gtg ccc ttc tac cga<br>Phe Tyr Ser Leu Pro Ser Gly Gly Tyr Thr Val Val Pro Phe Tyr Arg<br>          255                    260                  265 | 864 |
| gga gaa agg atc acc ttc gac gtg gcg ccc tcc cgg ctt gac ttc acg<br>Gly Glu Arg Ile Thr Phe Asp Val Ala Pro Ser Arg Leu Asp Phe Thr<br>          270                    275                  280 | 912 |
| gtg gag cac ggc agc ctg aga atc gag cct gta ttc cac gtc atg ggc<br>Val Glu His Gly Ser Leu Arg Ile Glu Pro Val Phe His Val Met Gly<br>285                    290                    295 | 960 |
| ttc tct gtc acc ggg aga gtc ttg aat gga cct gac gga gaa ggc gtc<br>Phe Ser Val Thr Gly Arg Val Leu Asn Gly Pro Asp Gly Glu Gly Val<br>300                    305                    310                  315 | 1008 |
| ccg gag gct gtg gtc acc ctg aac aac cag att aaa gtc aaa acg aag<br>Pro Glu Ala Val Val Thr Leu Asn Asn Gln Ile Lys Val Lys Thr Lys<br>                  320                    325                  330 | 1056 |
| gcc gac ggc tcc ttc cgc ctg gag aac ata acg aca ggg aca tac acc<br>Ala Asp Gly Ser Phe Arg Leu Glu Asn Ile Thr Thr Gly Thr Tyr Thr<br>          335                    340                  345 | 1104 |
| atc cac gct cag aag gag cac ctc tac ttc gag atg gtc acc atc aaa<br>Ile His Ala Gln Lys Glu His Leu Tyr Phe Glu Met Val Thr Ile Lys<br>          350                    355                  360 | 1152 |

```
att gcc ccc aat acc cca cag ctg gct gac ctc atc gct aca ggg ctt    1200
Ile Ala Pro Asn Thr Pro Gln Leu Ala Asp Leu Ile Ala Thr Gly Leu
365                 370                 375 ctc cct gca ggt tca gca tct gtg gtc aga tcg cca tcg tcc gct ccc    1248
Leu Pro Ala Gly Ser Ala Ser Val Val Arg Ser Pro Ser Ser Ala Pro
380                 385                 390                 395 ccg aca cca tca agc aga tga                                        1269
Pro Thr Pro Ser Ser Arg
                400

<210> SEQ ID NO 16
<211> LENGTH: 422
<212> TYPE: PRT
<213> ORGANISM: Mus musculus

<400> SEQUENCE: 16
```

Met Arg Ala Gly Arg Cys Ala Ala Ala Leu Leu Leu Leu Leu Leu Ser
    -20             -15                 -10

Gly Ala Gly Arg Ala Ile Gly Ser Glu Asp Ile Val Val Gly Cys Gly
-5              -1  1               5                   10

Gly Phe Val Lys Ser Asp Val Glu Ile Asn Tyr Ser Leu Ile Glu Ile
            15                  20                  25

Lys Leu Tyr Thr Lys His Gly Thr Leu Lys Tyr Gln Thr Asp Cys Ala
            30                  35                  40

Pro Asn Asn Gly Tyr Phe Met Ile Pro Leu Tyr Asp Lys Gly Asp Phe
            45                  50                  55

Ile Leu Lys Ile Glu Pro Pro Leu Gly Trp Ser Phe Glu Pro Thr Asn
60                  65                  70                  75

Val Glu Leu Arg Val Asp Gly Val Ser Asp Ile Cys Thr Lys Gly Gly
                80                  85                  90

Asp Ile Asn Phe Leu Phe Thr Gly Phe Ser Val Asn Gly Lys Val Leu
            95                  100                 105

Ser Lys Gly Gln Pro Leu Gly Pro Ala Gly Val Gln Val Ser Leu Arg
            110                 115                 120

Ser Thr Gly Ala Asp Ser Lys Ile Gln Ser Thr Val Thr Gln Pro Gly
            125                 130                 135

Gly Lys Phe Ala Phe Phe Lys Val Leu Pro Gly Asp Tyr Glu Ile Leu
140                 145                 150                 155

Ala Thr His Pro Thr Trp Ala Leu Lys Glu Ala Ser Thr Thr Val Arg
                160                 165                 170

Val Thr Asn Ser Asn Ala Asn Ala Ala Gly Pro Leu Ile Val Ala Gly
            175                 180                 185

Tyr Asn Val Ser Gly Ser Val Arg Ser Asp Gly Glu Pro Met Lys Gly
            190                 195                 200

Val Lys Phe Leu Leu Phe Ser Ser Leu Val Asn Lys Glu Asp Val Leu
            205                 210                 215

Gly Cys Asn Val Ser Pro Val Ser Gly Phe Gln Pro Pro Asp Glu Ser
220                 225                 230                 235

Leu Val Tyr Leu Cys Tyr Ala Val Ser Lys Glu Asp Gly Pro Phe Ser
            240                 245                 250

Phe Tyr Ser Leu Pro Ser Gly Gly Tyr Thr Val Val Pro Phe Tyr Arg
            255                 260                 265

Gly Glu Arg Ile Thr Phe Asp Val Ala Pro Ser Arg Leu Asp Phe Thr
            270                 275                 280

Val Glu His Gly Ser Leu Arg Ile Glu Pro Val Phe His Val Met Gly

```
                 285                 290                 295
Phe Ser Val Thr Gly Arg Val Leu Asn Gly Pro Asp Gly Glu Gly Val
300                 305                 310                 315

Pro Glu Ala Val Val Thr Leu Asn Asn Gln Ile Lys Val Lys Thr Lys
                320                 325                 330

Ala Asp Gly Ser Phe Arg Leu Glu Asn Ile Thr Thr Gly Thr Tyr Thr
                335                 340                 345

Ile His Ala Gln Lys Glu His Leu Tyr Phe Glu Met Val Thr Ile Lys
            350                 355                 360

Ile Ala Pro Asn Thr Pro Gln Leu Ala Asp Leu Ile Ala Thr Gly Leu
        365                 370                 375

Leu Pro Ala Gly Ser Ala Ser Val Val Arg Ser Pro Ser Ser Ala Pro
380                 385                 390                 395

Pro Thr Pro Ser Ser Arg
                400

<210> SEQ ID NO 17
<211> LENGTH: 531
<212> TYPE: DNA
<213> ORGANISM: Mus musculus
<220> FEATURE:
<221> NAME/KEY: CDS
<222> LOCATION: (1)..(528)
<223> OTHER INFORMATION:
<220> FEATURE:
<221> NAME/KEY: sig_peptide
<222> LOCATION: (1)..(81)
<223> OTHER INFORMATION:
<220> FEATURE:
<221> NAME/KEY: mat_peptide
<222> LOCATION: (82)..()
<223> OTHER INFORMATION:

<400> SEQUENCE: 17 atg gca gcg agc acg gac ata gct ggg ctg gag gag agc ttc cgg aag        48
Met Ala Ala Ser Thr Asp Ile Ala Gly Leu Glu Glu Ser Phe Arg Lys
        -25                 -20                 -15 ttt gcc atc cat ggc gac ccc aag gcc agc ggg caa gag atg aat ggc        96
Phe Ala Ile His Gly Asp Pro Lys Ala Ser Gly Gln Glu Met Asn Gly
    -10                 -5                  -1  1               5 aag aac tgg gcc aag ctg tgc aag gac tgt aag gtg gcc gac gga aag       144
Lys Asn Trp Ala Lys Leu Cys Lys Asp Cys Lys Val Ala Asp Gly Lys
                10                  15                  20 gcc gta acg ggc acc gac gtc gac atc gtc ttc tcc aaa gtc aag gcg       192
Ala Val Thr Gly Thr Asp Val Asp Ile Val Phe Ser Lys Val Lys Ala
                25                  30                  35 aaa tct gct aga gta atc aac tat gag gag ttc aag aag gcc ctg gaa       240
Lys Ser Ala Arg Val Ile Asn Tyr Glu Glu Phe Lys Lys Ala Leu Glu
            40                  45                  50 gag ctg gca act aag cgg ttc aag ggg aag tcc aag gag gag gcc ttt       288
Glu Leu Ala Thr Lys Arg Phe Lys Gly Lys Ser Lys Glu Glu Ala Phe
        55                  60                  65 gat gcc atc tgc cag ctg ata gcg ggc aag gaa ccg gcc aac att ggc       336
Asp Ala Ile Cys Gln Leu Ile Ala Gly Lys Glu Pro Ala Asn Ile Gly
70                  75                  80                  85 gtc acc aaa gct aaa acg ggt ggt gct gtg gac cgg ctg acg gac acc       384
Val Thr Lys Ala Lys Thr Gly Gly Ala Val Asp Arg Leu Thr Asp Thr
                90                  95                  100 agt aag tat acg ggc tcc cac aaa gaa cgc ttt gat gag agc ggc aag       432
Ser Lys Tyr Thr Gly Ser His Lys Glu Arg Phe Asp Glu Ser Gly Lys
            105                 110                 115
```

```
gga aag ggc atc gct gga cgg cag gac atc ctg gac gac agt ggc tac      480
Gly Lys Gly Ile Ala Gly Arg Gln Asp Ile Leu Asp Asp Ser Gly Tyr
        120             125             130 gtg agt gcc tac aaa aac gca ggc acc tat gac gcc aag gtg aag aag      528
Val Ser Ala Tyr Lys Asn Ala Gly Thr Tyr Asp Ala Lys Val Lys Lys
    135             140             145 tga                                                                  531
```

```
<210> SEQ ID NO 18
<211> LENGTH: 176
<212> TYPE: PRT
<213> ORGANISM: Mus musculus

<400> SEQUENCE: 18

Met Ala Ala Ser Thr Asp Ile Ala Gly Leu Glu Glu Ser Phe Arg Lys
        -25                 -20                 -15

Phe Ala Ile His Gly Asp Pro Lys Ala Ser Gly Gln Glu Met Asn Gly
    -10                 -5              -1   1                   5

Lys Asn Trp Ala Lys Leu Cys Lys Asp Cys Lys Val Ala Asp Gly Lys
                10                  15                  20

Ala Val Thr Gly Thr Asp Val Asp Ile Val Phe Ser Lys Val Lys Ala
            25                  30                  35

Lys Ser Ala Arg Val Ile Asn Tyr Glu Glu Phe Lys Lys Ala Leu Glu
        40                  45                  50

Glu Leu Ala Thr Lys Arg Phe Lys Gly Lys Ser Lys Glu Glu Ala Phe
    55                  60                  65

Asp Ala Ile Cys Gln Leu Ile Ala Gly Lys Glu Pro Ala Asn Ile Gly
70                  75                  80                  85

Val Thr Lys Ala Lys Thr Gly Gly Ala Val Asp Arg Leu Thr Asp Thr
            90                  95                  100

Ser Lys Tyr Thr Gly Ser His Lys Glu Arg Phe Asp Glu Ser Gly Lys
        105                 110                 115

Gly Lys Gly Ile Ala Gly Arg Gln Asp Ile Leu Asp Asp Ser Gly Tyr
    120                 125                 130

Val Ser Ala Tyr Lys Asn Ala Gly Thr Tyr Asp Ala Lys Val Lys Lys
        135                 140                 145
```

```
<210> SEQ ID NO 19
<211> LENGTH: 588
<212> TYPE: DNA
<213> ORGANISM: Mus musculus
<220> FEATURE:
<221> NAME/KEY: CDS
<222> LOCATION: (1)..(585)
<223> OTHER INFORMATION:
<220> FEATURE:
<221> NAME/KEY: sig_peptide
<222> LOCATION: (1)..(51)
<223> OTHER INFORMATION:
<220> FEATURE:
<221> NAME/KEY: mat_peptide
<222> LOCATION: (52)..()
<223> OTHER INFORMATION:

<400> SEQUENCE: 19 atg gct tca gga tgg ttt tac ctg tcc tgc atg gtg ctg gga tcg ctg       48
Met Ala Ser Gly Trp Phe Tyr Leu Ser Cys Met Val Leu Gly Ser Leu
        -15                 -10                 -5 gga tcg atg tgc atc ctc ttc act gcc tac tgg atg cag tac tgg cgc       96
Gly Ser Met Cys Ile Leu Phe Thr Ala Tyr Trp Met Gln Tyr Trp Arg
-1   1               5                   10                  15
```

-continued

```
ggt ggc ttt gcc tgg gat ggc acg gtg ctc atg ttt aac tgg cac cca      144
Gly Gly Phe Ala Trp Asp Gly Thr Val Leu Met Phe Asn Trp His Pro
             20                  25                  30 gtg ctc atg gtt gcc ggc atg gtg gtg ctc tat gga gct gcc tca ctg      192
Val Leu Met Val Ala Gly Met Val Val Leu Tyr Gly Ala Ala Ser Leu
         35                  40                  45 gtg tac cgc ctg cct tca tcg tgg gtg ggg ccc agg ctg ccc tgg aaa      240
Val Tyr Arg Leu Pro Ser Ser Trp Val Gly Pro Arg Leu Pro Trp Lys
     50                  55                  60 gtt ctc cat gca gca ctg cac ctg ctg gcc ttc acc tgc act gtg gtg      288
Val Leu His Ala Ala Leu His Leu Leu Ala Phe Thr Cys Thr Val Val
 65                  70                  75 ggg ctg att gcc gtc ttt cgg ttt cac aac cac tcg aga atc gca cac      336
Gly Leu Ile Ala Val Phe Arg Phe His Asn His Ser Arg Ile Ala His
80                  85                  90                  95 ctc tac tcc ctg cac agc tgg ctg ggt atc acc act gta gtc ctc ttc      384
Leu Tyr Ser Leu His Ser Trp Leu Gly Ile Thr Thr Val Val Leu Phe
                100                 105                 110 gcc tgc cag tgg ttc ctg ggc ttt gct gtc ttc ctc ctg ccc tgg gca      432
Ala Cys Gln Trp Phe Leu Gly Phe Ala Val Phe Leu Leu Pro Trp Ala
            115                 120                 125 tcc cag tgg ctg cga agc ctc ctg aaa cct ctg cat gta ttc ttt gga      480
Ser Gln Trp Leu Arg Ser Leu Leu Lys Pro Leu His Val Phe Phe Gly
        130                 135                 140 gcc tgc atc ctt tcc ctg tcc atc aca tct gtt att tcc ggc atc aat      528
Ala Cys Ile Leu Ser Leu Ser Ile Thr Ser Val Ile Ser Gly Ile Asn
    145                 150                 155 gag aag ctt ttc ttt gtt ttg aaa aat gcc acc aag ccc cta ctc cag      576
Glu Lys Leu Phe Phe Val Leu Lys Asn Ala Thr Lys Pro Leu Leu Gln
160                 165                 170                 175 cct gcc tgg tga                                                      588
Pro Ala Trp
```

```
<210> SEQ ID NO 20
<211> LENGTH: 195
<212> TYPE: PRT
<213> ORGANISM: Mus musculus

<400> SEQUENCE: 20

Met Ala Ser Gly Trp Phe Tyr Leu Ser Cys Met Val Leu Gly Ser Leu
        -15                 -10                  -5

Gly Ser Met Cys Ile Leu Phe Thr Ala Tyr Trp Met Gln Tyr Trp Arg
 -1   1               5                  10                  15

Gly Gly Phe Ala Trp Asp Gly Thr Val Leu Met Phe Asn Trp His Pro
             20                  25                  30

Val Leu Met Val Ala Gly Met Val Val Leu Tyr Gly Ala Ala Ser Leu
         35                  40                  45

Val Tyr Arg Leu Pro Ser Ser Trp Val Gly Pro Arg Leu Pro Trp Lys
     50                  55                  60

Val Leu His Ala Ala Leu His Leu Leu Ala Phe Thr Cys Thr Val Val
 65                  70                  75

Gly Leu Ile Ala Val Phe Arg Phe His Asn His Ser Arg Ile Ala His
80                  85                  90                  95

Leu Tyr Ser Leu His Ser Trp Leu Gly Ile Thr Thr Val Val Leu Phe
                100                 105                 110

Ala Cys Gln Trp Phe Leu Gly Phe Ala Val Phe Leu Leu Pro Trp Ala
            115                 120                 125

Ser Gln Trp Leu Arg Ser Leu Leu Lys Pro Leu His Val Phe Phe Gly
```

```
                    130             135             140
Ala Cys Ile Leu Ser Leu Ser Ile Thr Ser Val Ile Ser Gly Ile Asn
    145                 150                 155

Glu Lys Leu Phe Phe Val Leu Lys Asn Ala Thr Lys Pro Leu Leu Gln
160                 165                 170                 175

Pro Ala Trp

<210> SEQ ID NO 21
<211> LENGTH: 3147
<212> TYPE: DNA
<213> ORGANISM: Mus musculus
<220> FEATURE:
<221> NAME/KEY: CDS
<222> LOCATION: (1)..(3144)
<223> OTHER INFORMATION:
<220> FEATURE:
<221> NAME/KEY: sig_peptide
<222> LOCATION: (1)..(147)
<223> OTHER INFORMATION:
<220> FEATURE:
<221> NAME/KEY: mat_peptide
<222> LOCATION: (148)..()
<223> OTHER INFORMATION:

<400> SEQUENCE: 21
```

| | | | | | | | | | | | | | | | | |
|---|---|---|---|---|---|---|---|---|---|---|---|---|---|---|---|---|
| atg | gag | aag | aga | ctg | gga | gtc | aag | cca | agt | ccc | gct | tcc | tgg | gtt | ttg | 48 |
| Met | Glu | Lys | Arg | Leu | Gly | Val | Lys | Pro | Ser | Pro | Ala | Ser | Trp | Val | Leu | |
| | | | -45 | | | | -40 | | | | -35 | | | | | |
| cca | gga | tat | tgt | tgg | cag | aca | tca | gtg | aag | ctg | ccg | aga | agc | ctg | tac | 96 |
| Pro | Gly | Tyr | Cys | Trp | Gln | Thr | Ser | Val | Lys | Leu | Pro | Arg | Ser | Leu | Tyr | |
| | | | -30 | | | | -25 | | | | -20 | | | | | |
| ctg | ctt | tac | agt | ttc | ttc | tgc | ttc | agc | gtt | ctg | tgg | ttg | tca | aca | gat | 144 |
| Leu | Leu | Tyr | Ser | Phe | Phe | Cys | Phe | Ser | Val | Leu | Trp | Leu | Ser | Thr | Asp | |
| | | | -15 | | | | -10 | | | | -5 | | | | | |
| gct | gat | gag | agc | aga | tgc | caa | cag | ggg | aag | aca | ctt | tat | gga | gct | ggc | 192 |
| Ala | Asp | Glu | Ser | Arg | Cys | Gln | Gln | Gly | Lys | Thr | Leu | Tyr | Gly | Ala | Gly | |
| -1  | 1   |     |     | 5   |     |     |     |     | 10  |     |     |     |     | 15  | | |
| ttg | aga | act | gag | gga | gaa | aat | cac | ctc | cgg | ctt | ctt | gca | gga | agc | ctg | 240 |
| Leu | Arg | Thr | Glu | Gly | Glu | Asn | His | Leu | Arg | Leu | Leu | Ala | Gly | Ser | Leu | |
| | | | 20 | | | | 25 | | | | 30 | | | | | |
| cct | ttc | cac | gcc | tgt | cgg | gct | gcc | tgc | tgc | cgg | gac | tct | gcc | tgc | cac | 288 |
| Pro | Phe | His | Ala | Cys | Arg | Ala | Ala | Cys | Cys | Arg | Asp | Ser | Ala | Cys | His | |
| | | 35 | | | | 40 | | | | 45 | | | | | | |
| gct | cta | tgg | tgg | ctg | gaa | ggg | atg | tgc | ttt | cag | gct | gac | tgc | agc | aag | 336 |
| Ala | Leu | Trp | Trp | Leu | Glu | Gly | Met | Cys | Phe | Gln | Ala | Asp | Cys | Ser | Lys | |
| | | 50 | | | | 55 | | | | 60 | | | | | | |
| ccc | cag | agc | tgc | cag | cct | ttt | agg | aca | gac | tct | tcc | aat | tcc | atg | ctg | 384 |
| Pro | Gln | Ser | Cys | Gln | Pro | Phe | Arg | Thr | Asp | Ser | Ser | Asn | Ser | Met | Leu | |
| | 65 | | | | 70 | | | | 75 | | | | | | | |
| atc | att | ttt | caa | aaa | tcc | caa | act | aca | gat | gat | ttg | ggc | ctt | ctg | cct | 432 |
| Ile | Ile | Phe | Gln | Lys | Ser | Gln | Thr | Thr | Asp | Asp | Leu | Gly | Leu | Leu | Pro | |
| 80 | | | | 85 | | | | 90 | | | | 95 | | | | |
| gaa | gat | gat | gaa | cca | cat | ctt | ctg | agg | cta | ggc | tgg | ggc | agg | aca | tcg | 480 |
| Glu | Asp | Asp | Glu | Pro | His | Leu | Leu | Arg | Leu | Gly | Trp | Gly | Arg | Thr | Ser | |
| | | | 100 | | | | 105 | | | | 110 | | | | | |
| tgg | agg | agg | cag | agc | ctt | ctt | ggg | gct | ccc | ctc | acc | ctt | tct | gta | ccc | 528 |
| Trp | Arg | Arg | Gln | Ser | Leu | Leu | Gly | Ala | Pro | Leu | Thr | Leu | Ser | Val | Pro | |
| | | | 115 | | | | 120 | | | | 125 | | | | | |
| tct | agt | cac | cac | cag | agc | tta | ctc | agg | gat | cgg | cag | aag | aga | gat | ctc | 576 |
| Ser | Ser | His | His | Gln | Ser | Leu | Leu | Arg | Asp | Arg | Gln | Lys | Arg | Asp | Leu | |
| | | | 130 | | | | 135 | | | | 140 | | | | | |
| agt | gtg | gta | cct | aca | cat | gga | gcg | atg | cag | cat | tct | aaa | gtg | aat | cac | 624 |

```
                                                        -continued

Ser Val Val Pro Thr His Gly Ala Met Gln His Ser Lys Val Asn His
    145                 150                 155 tcc gag gaa gca ggt gct ctg agt ccc acc tct gca gag gtc cgc aaa        672
Ser Glu Glu Ala Gly Ala Leu Ser Pro Thr Ser Ala Glu Val Arg Lys
160                 165                 170                 175 acc att aca gtt gcc ggt tcc ttc acc agt aac cac act aca cag act        720
Thr Ile Thr Val Ala Gly Ser Phe Thr Ser Asn His Thr Thr Gln Thr
                    180                 185                 190 cct gag tgg ccc aag aat gtg tcc atc cat cct gaa cca tcc gag cac        768
Pro Glu Trp Pro Lys Asn Val Ser Ile His Pro Glu Pro Ser Glu His
                195                 200                 205 tcc agt cct gta tct ggt act ccg caa gta aaa agc act gag cac agt        816
Ser Ser Pro Val Ser Gly Thr Pro Gln Val Lys Ser Thr Glu His Ser
            210                 215                 220 cca act gat gcc cct ctg cca gtg gcc ccc tcc tac agc tat gcc acc        864
Pro Thr Asp Ala Pro Leu Pro Val Ala Pro Ser Tyr Ser Tyr Ala Thr
225                 230                 235 ccc acg ccc cag gcc tct tct cag agc acc tca gca cca cac cca gtt        912
Pro Thr Pro Gln Ala Ser Ser Gln Ser Thr Ser Ala Pro His Pro Val
240                 245                 250                 255 gta aag gag ctg gtg gtg tct gct ggg aag agc gtc cag atc acc ctg        960
Val Lys Glu Leu Val Val Ser Ala Gly Lys Ser Val Gln Ile Thr Leu
                    260                 265                 270 cct aag aat gaa gtt cag tta aat gcc ttc gtc ctt cca gaa gca gag       1008
Pro Lys Asn Glu Val Gln Leu Asn Ala Phe Val Leu Pro Glu Ala Glu
                275                 280                 285 cca gga gaa acc tac acc tac gac tgg cag ctg atc act cat cct aca       1056
Pro Gly Glu Thr Tyr Thr Tyr Asp Trp Gln Leu Ile Thr His Pro Thr
            290                 295                 300 gac tac agt gga gag gtg gag agg aaa cat tcc cag agc ctc caa ctg       1104
Asp Tyr Ser Gly Glu Val Glu Arg Lys His Ser Gln Ser Leu Gln Leu
305                 310                 315 tcc aag ctg act cca ggc ctg tac gaa ttc aag gtg act gtg gat ggc       1152
Ser Lys Leu Thr Pro Gly Leu Tyr Glu Phe Lys Val Thr Val Asp Gly
320                 325                 330                 335 cag aat gcc cat ggg gaa ggc tac gtg aat gtg aca gtg aaa cca gag       1200
Gln Asn Ala His Gly Glu Gly Tyr Val Asn Val Thr Val Lys Pro Glu
                    340                 345                 350 ccc cgt aag aac cgg cct ccc gtt gct gtg gtg tca cct cag ttc cag       1248
Pro Arg Lys Asn Arg Pro Pro Val Ala Val Val Ser Pro Gln Phe Gln
                355                 360                 365 gag atc tcg ctg cca acc act tct acc atc att gat ggc agc cag agc       1296
Glu Ile Ser Leu Pro Thr Thr Ser Thr Ile Ile Asp Gly Ser Gln Ser
            370                 375                 380 acg gat gac gat aaa att gtc cag tac cac tgg gaa gag ctt aag ggg       1344
Thr Asp Asp Asp Lys Ile Val Gln Tyr His Trp Glu Glu Leu Lys Gly
385                 390                 395 ccc ctg aga gaa gag aag atc tct gaa gac aca gcc ata cta aaa ctt       1392
Pro Leu Arg Glu Glu Lys Ile Ser Glu Asp Thr Ala Ile Leu Lys Leu
400                 405                 410                 415 agt aag ctc gtc ccg ggg aac tac acc ttc agc tta act gtt gtc gac       1440
Ser Lys Leu Val Pro Gly Asn Tyr Thr Phe Ser Leu Thr Val Val Asp
                    420                 425                 430 tct gac ggg gct acc aac tcc acc act gca agc ctg act gtg aac aaa       1488
Ser Asp Gly Ala Thr Asn Ser Thr Thr Ala Ser Leu Thr Val Asn Lys
                435                 440                 445 gct gtg gac tac cct ccc gtg gcc aat gca ggc ccc aac caa gtg atc       1536
Ala Val Asp Tyr Pro Pro Val Ala Asn Ala Gly Pro Asn Gln Val Ile
                    450                 455                 460
```

-continued

```
acc ctg cct cag aac tcc atc acc ctc ttt gga aac cag agc acg gat    1584
Thr Leu Pro Gln Asn Ser Ile Thr Leu Phe Gly Asn Gln Ser Thr Asp
465                 470                 475 gac cac ggc atc acc agc tat gag tgg tcg ctc agc ccg agc agc aaa    1632
Asp His Gly Ile Thr Ser Tyr Glu Trp Ser Leu Ser Pro Ser Ser Lys
480                 485                 490                 495 ggg aag gtg gtg gag atg cag gga gtt aga acg cca gcc ctg cag ctg    1680
Gly Lys Val Val Glu Met Gln Gly Val Arg Thr Pro Ala Leu Gln Leu
                500                 505                 510 tcc gca atg caa gaa gga gac tat acc tac cag ctc aca gtg act gac    1728
Ser Ala Met Gln Glu Gly Asp Tyr Thr Tyr Gln Leu Thr Val Thr Asp
            515                 520                 525 acc gca gga caa cag gcc acc gcc caa gtg act gtg att gtg cag cct    1776
Thr Ala Gly Gln Gln Ala Thr Ala Gln Val Thr Val Ile Val Gln Pro
        530                 535                 540 gag aac aac aag cct cct cag gca gat gca ggc cca gac aaa gag ctg    1824
Glu Asn Asn Lys Pro Pro Gln Ala Asp Ala Gly Pro Asp Lys Glu Leu
545                 550                 555 acc ctg ccc gtg gac agc aca acc ctg gac ggc agc aag agc aca gat    1872
Thr Leu Pro Val Asp Ser Thr Thr Leu Asp Gly Ser Lys Ser Thr Asp
560                 565                 570                 575 gac cag aga gtc gtc tct tac ctt tgg gag cag agt cgg gga cct gac    1920
Asp Gln Arg Val Val Ser Tyr Leu Trp Glu Gln Ser Arg Gly Pro Asp
                580                 585                 590 ggg gtg cag ctg gag aat gcc aac agc agt gtc gcc act gtg act ggg    1968
Gly Val Gln Leu Glu Asn Ala Asn Ser Ser Val Ala Thr Val Thr Gly
            595                 600                 605 ctg caa gtc ggg act tat gta ttc acc ttg act gtc aaa gat gag agg    2016
Leu Gln Val Gly Thr Tyr Val Phe Thr Leu Thr Val Lys Asp Glu Arg
        610                 615                 620 aac cta cag agc cag agc tcc gtt aat gtc att gtc aaa gaa gaa ata    2064
Asn Leu Gln Ser Gln Ser Ser Val Asn Val Ile Val Lys Glu Glu Ile
625                 630                 635 aac aaa ccg cca gta gcc aag atc gct ggg aac gtg gtg gtg acc ttg    2112
Asn Lys Pro Pro Val Ala Lys Ile Ala Gly Asn Val Val Val Thr Leu
640                 645                 650                 655 ccc acg agc aca gct gag ctg gat ggc tcg agg tcc tca gat gac aag    2160
Pro Thr Ser Thr Ala Glu Leu Asp Gly Ser Arg Ser Ser Asp Asp Lys
                660                 665                 670 ggg ata gtc agc tac ctg tgg act cga gat gag acg agc cca gcc gca    2208
Gly Ile Val Ser Tyr Leu Trp Thr Arg Asp Glu Thr Ser Pro Ala Ala
            675                 680                 685 ggg gag gtg ctg aat cac tct gac cac cac cct gtc ctc ttc ctc tcc    2256
Gly Glu Val Leu Asn His Ser Asp His His Pro Val Leu Phe Leu Ser
        690                 695                 700 aac ctg gtg gag ggg acc tac acg ttt cac ctg aaa gtg aca gat gca    2304
Asn Leu Val Glu Gly Thr Tyr Thr Phe His Leu Lys Val Thr Asp Ala
705                 710                 715 aag ggc gag agc gac aca gac cgg acg aca gtg gaa gtg aag cct gac    2352
Lys Gly Glu Ser Asp Thr Asp Arg Thr Thr Val Glu Val Lys Pro Asp
720                 725                 730                 735 ccc agg aaa agc aac cta gtg gag atc atc ttg gat gtg aac gtc agt    2400
Pro Arg Lys Ser Asn Leu Val Glu Ile Ile Leu Asp Val Asn Val Ser
                740                 745                 750 cag ctg act gag agg ctg aag ggg atg ctc atc cgc cag att ggg gtc    2448
Gln Leu Thr Glu Arg Leu Lys Gly Met Leu Ile Arg Gln Ile Gly Val
            755                 760                 765 ctc ctg ggg gtg ctg gat tcc gac atc att gtg caa aag att cag ccg    2496
Leu Leu Gly Val Leu Asp Ser Asp Ile Ile Val Gln Lys Ile Gln Pro
        770                 775                 780
```

-continued

```
tac acg gag cag agc acc aag atg ttg ttt ttt gtt cag aac gac cct    2544
Tyr Thr Glu Gln Ser Thr Lys Met Leu Phe Phe Val Gln Asn Asp Pro
785                 790                 795 ccc cac cag ctc ttc aaa ggc cat gag gtg gca gcc atg ctc aag agc    2592
Pro His Gln Leu Phe Lys Gly His Glu Val Ala Ala Met Leu Lys Ser
800                 805                 810                 815 gag ctg cag aag cag aag gct gac ttc ctc atc ttc aga gcc ctg gaa    2640
Glu Leu Gln Lys Gln Lys Ala Asp Phe Leu Ile Phe Arg Ala Leu Glu
                820                 825                 830 atc agc aca gtc aca tgt cag ctg aac tgt tct gac cat ggc cac tgt    2688
Ile Ser Thr Val Thr Cys Gln Leu Asn Cys Ser Asp His Gly His Cys
835                 840                 845 gac tca ttc acc aag cgc tgt gtc tgt gac ccg ttt tgg atg gag aat    2736
Asp Ser Phe Thr Lys Arg Cys Val Cys Asp Pro Phe Trp Met Glu Asn
    850                 855                 860 ttc atc aag gtg cag ctg agg gat gga gac agc aac tgt gaa tgg agc    2784
Phe Ile Lys Val Gln Leu Arg Asp Gly Asp Ser Asn Cys Glu Trp Ser
865                 870                 875 gtg ctc tac gtc atc att gcc tcc ttt gtc att gtt gtt gcc ttg ggg    2832
Val Leu Tyr Val Ile Ile Ala Ser Phe Val Ile Val Val Ala Leu Gly
880                 885                 890                 895 atc ctg tca tgg act aca atc tgc tgc tgc aag agg caa aaa gga aaa    2880
Ile Leu Ser Trp Thr Thr Ile Cys Cys Cys Lys Arg Gln Lys Gly Lys
                900                 905                 910 ccc aag agg aaa agc aga tac aag atc ctg gat gcc aca gat cag gag    2928
Pro Lys Arg Lys Ser Arg Tyr Lys Ile Leu Asp Ala Thr Asp Gln Glu
                915                 920                 925 agc ctg gag ctg aaa cca acc tcc cga gca ggc agc aaa cag aaa ggc    2976
Ser Leu Glu Leu Lys Pro Thr Ser Arg Ala Gly Ser Lys Gln Lys Gly
            930                 935                 940 ccc acg ctg agc agc agc ctg atg cat tct gaa tcg gag ctg gac agc    3024
Pro Thr Leu Ser Ser Ser Leu Met His Ser Glu Ser Glu Leu Asp Ser
945                 950                 955 gac gat gcc atc ttc aca tgg cca gac cgg gag aag ggc aaa cta ctg    3072
Asp Asp Ala Ile Phe Thr Trp Pro Asp Arg Glu Lys Gly Lys Leu Leu
960                 965                 970                 975 tat ggt cag aat ggc tct gtg cca aac ggg caa aca cct ttg aag tcc    3120
Tyr Gly Gln Asn Gly Ser Val Pro Asn Gly Gln Thr Pro Leu Lys Ser
                980                 985                 990 agg agc gca cgg gag gag atc ttg tag                                3147
Arg Ser Ala Arg Glu Glu Ile Leu
                995

<210> SEQ ID NO 22
<211> LENGTH: 1048
<212> TYPE: PRT
<213> ORGANISM: Mus musculus

<400> SEQUENCE: 22

Met Glu Lys Arg Leu Gly Val Lys Pro Ser Pro Ala Ser Trp Val Leu
                -45                 -40                 -35

Pro Gly Tyr Cys Trp Gln Thr Ser Val Lys Leu Pro Arg Ser Leu Tyr
            -30                 -25                 -20

Leu Leu Tyr Ser Phe Phe Cys Phe Ser Val Leu Trp Leu Ser Thr Asp
        -15                 -10                  -5

Ala Asp Glu Ser Arg Cys Gln Gln Gly Lys Thr Leu Tyr Gly Ala Gly
 -1   1               5                  10                  15

Leu Arg Thr Glu Gly Glu Asn His Leu Arg Leu Leu Ala Gly Ser Leu
                 20                  25                  30
```

```
Pro Phe His Ala Cys Arg Ala Ala Cys Cys Arg Asp Ser Ala Cys His
            35                  40                  45

Ala Leu Trp Trp Leu Glu Gly Met Cys Phe Gln Ala Asp Cys Ser Lys
    50                  55                  60

Pro Gln Ser Cys Gln Pro Phe Arg Thr Asp Ser Ser Asn Ser Met Leu
65                  70                  75

Ile Ile Phe Gln Lys Ser Gln Thr Thr Asp Asp Leu Gly Leu Leu Pro
80                  85                  90                  95

Glu Asp Asp Glu Pro His Leu Leu Arg Leu Gly Trp Gly Arg Thr Ser
                100                 105                 110

Trp Arg Arg Gln Ser Leu Leu Gly Ala Pro Leu Thr Leu Ser Val Pro
                115                 120                 125

Ser Ser His His Gln Ser Leu Leu Arg Asp Arg Gln Lys Arg Asp Leu
            130                 135                 140

Ser Val Val Pro Thr His Gly Ala Met Gln His Ser Lys Val Asn His
        145                 150                 155

Ser Glu Glu Ala Gly Ala Leu Ser Pro Thr Ser Ala Glu Val Arg Lys
160                 165                 170                 175

Thr Ile Thr Val Ala Gly Ser Phe Thr Ser Asn His Thr Thr Gln Thr
                    180                 185                 190

Pro Glu Trp Pro Lys Asn Val Ser Ile His Pro Glu Pro Ser Glu His
            195                 200                 205

Ser Ser Pro Val Ser Gly Thr Pro Gln Val Lys Ser Thr Glu His Ser
        210                 215                 220

Pro Thr Asp Ala Pro Leu Pro Val Ala Pro Ser Tyr Ser Tyr Ala Thr
    225                 230                 235

Pro Thr Pro Gln Ala Ser Ser Gln Ser Thr Ser Ala Pro His Pro Val
240                 245                 250                 255

Val Lys Glu Leu Val Val Ser Ala Gly Lys Ser Val Gln Ile Thr Leu
                    260                 265                 270

Pro Lys Asn Glu Val Gln Leu Asn Ala Phe Val Leu Pro Glu Ala Glu
            275                 280                 285

Pro Gly Glu Thr Tyr Thr Tyr Asp Trp Gln Leu Ile Thr His Pro Thr
        290                 295                 300

Asp Tyr Ser Gly Glu Val Glu Arg Lys His Ser Gln Ser Leu Gln Leu
    305                 310                 315

Ser Lys Leu Thr Pro Gly Leu Tyr Glu Phe Lys Val Thr Val Asp Gly
320                 325                 330                 335

Gln Asn Ala His Gly Glu Gly Tyr Val Asn Val Thr Val Lys Pro Glu
                    340                 345                 350

Pro Arg Lys Asn Arg Pro Pro Val Ala Val Ser Pro Gln Phe Gln
            355                 360                 365

Glu Ile Ser Leu Pro Thr Thr Ser Thr Ile Asp Gly Ser Gln Ser
        370                 375                 380

Thr Asp Asp Asp Lys Ile Val Gln Tyr His Trp Glu Glu Leu Lys Gly
    385                 390                 395

Pro Leu Arg Glu Glu Lys Ile Ser Glu Asp Thr Ala Ile Leu Lys Leu
400                 405                 410                 415

Ser Lys Leu Val Pro Gly Asn Tyr Thr Phe Ser Leu Thr Val Val Asp
                    420                 425                 430

Ser Asp Gly Ala Thr Asn Ser Thr Thr Ala Ser Leu Thr Val Asn Lys
            435                 440                 445
```

```
Ala Val Asp Tyr Pro Pro Val Ala Asn Ala Gly Pro Asn Gln Val Ile
            450                 455                 460

Thr Leu Pro Gln Asn Ser Ile Thr Leu Phe Gly Asn Gln Ser Thr Asp
465                 470                 475

Asp His Gly Ile Thr Ser Tyr Glu Trp Ser Leu Ser Pro Ser Ser Lys
480                 485                 490                 495

Gly Lys Val Val Glu Met Gln Gly Val Arg Thr Pro Ala Leu Gln Leu
                500                 505                 510

Ser Ala Met Gln Glu Gly Asp Tyr Thr Tyr Gln Leu Thr Val Thr Asp
                515                 520                 525

Thr Ala Gly Gln Gln Ala Thr Ala Gln Val Thr Val Ile Val Gln Pro
            530                 535                 540

Glu Asn Asn Lys Pro Pro Gln Ala Asp Ala Gly Pro Asp Lys Glu Leu
545                 550                 555

Thr Leu Pro Val Asp Ser Thr Thr Leu Asp Gly Ser Lys Ser Thr Asp
560                 565                 570                 575

Asp Gln Arg Val Val Ser Tyr Leu Trp Glu Gln Ser Arg Gly Pro Asp
                580                 585                 590

Gly Val Gln Leu Glu Asn Ala Asn Ser Ser Val Ala Thr Val Thr Gly
                595                 600                 605

Leu Gln Val Gly Thr Tyr Val Phe Thr Leu Thr Val Lys Asp Glu Arg
            610                 615                 620

Asn Leu Gln Ser Gln Ser Ser Val Asn Val Ile Val Lys Glu Glu Ile
625                 630                 635

Asn Lys Pro Pro Val Ala Lys Ile Ala Gly Asn Val Val Val Thr Leu
640                 645                 650                 655

Pro Thr Ser Thr Ala Glu Leu Asp Gly Ser Arg Ser Ser Asp Asp Lys
                660                 665                 670

Gly Ile Val Ser Tyr Leu Trp Thr Arg Asp Glu Thr Ser Pro Ala Ala
                675                 680                 685

Gly Glu Val Leu Asn His Ser Asp His His Pro Val Leu Phe Leu Ser
            690                 695                 700

Asn Leu Val Glu Gly Thr Tyr Thr Phe His Leu Lys Val Thr Asp Ala
705                 710                 715

Lys Gly Glu Ser Asp Thr Asp Arg Thr Thr Val Glu Val Lys Pro Asp
720                 725                 730                 735

Pro Arg Lys Ser Asn Leu Val Glu Ile Ile Leu Asp Val Asn Val Ser
                740                 745                 750

Gln Leu Thr Glu Arg Leu Lys Gly Met Leu Ile Arg Gln Ile Gly Val
                755                 760                 765

Leu Leu Gly Val Leu Asp Ser Asp Ile Ile Val Gln Lys Ile Gln Pro
            770                 775                 780

Tyr Thr Glu Gln Ser Thr Lys Met Leu Phe Phe Val Gln Asn Asp Pro
785                 790                 795

Pro His Gln Leu Phe Lys Gly His Glu Val Ala Ala Met Leu Lys Ser
800                 805                 810                 815

Glu Leu Gln Lys Gln Lys Ala Asp Phe Leu Ile Phe Arg Ala Leu Glu
                820                 825                 830

Ile Ser Thr Val Thr Cys Gln Leu Asn Cys Ser Asp His Gly His Cys
                835                 840                 845

Asp Ser Phe Thr Lys Arg Cys Val Cys Asp Pro Phe Trp Met Glu Asn
            850                 855                 860

Phe Ile Lys Val Gln Leu Arg Asp Gly Asp Ser Asn Cys Glu Trp Ser
```

| | | | | | | | | |
|---|---|---|---|---|---|---|---|---|
| | | 865 | | | 870 | | | 875 |

Val Leu Tyr Val Ile Ile Ala Ser Phe Val Ile Val Ala Leu Gly
880        885        890        895

Ile Leu Ser Trp Thr Thr Ile Cys Cys Cys Lys Arg Gln Lys Gly Lys
        900        905        910

Pro Lys Arg Lys Ser Arg Tyr Lys Ile Leu Asp Ala Thr Asp Gln Glu
      915        920        925

Ser Leu Glu Leu Lys Pro Thr Ser Arg Ala Gly Ser Lys Gln Lys Gly
    930        935        940

Pro Thr Leu Ser Ser Ser Leu Met His Ser Glu Ser Glu Leu Asp Ser
945        950        955

Asp Asp Ala Ile Phe Thr Trp Pro Asp Arg Glu Lys Gly Lys Leu Leu
960        965        970        975

Tyr Gly Gln Asn Gly Ser Val Pro Asn Gly Gln Thr Pro Leu Lys Ser
        980        985        990

Arg Ser Ala Arg Glu Glu Ile Leu
    995

```
<210> SEQ ID NO 23
<211> LENGTH: 691
<212> TYPE: DNA
<213> ORGANISM: Mus musculus
<220> FEATURE:
<221> NAME/KEY: misc_feature
<222> LOCATION: (633)..(633)
<223> OTHER INFORMATION: 'n' stands for unidentified base.
<220> FEATURE:
<221> NAME/KEY: misc_feature
<222> LOCATION: (680)..(680)
<223> OTHER INFORMATION: 'n' stands for unidentified base.
<220> FEATURE:
<221> NAME/KEY: misc_feature
<222> LOCATION: (682)..(682)
<223> OTHER INFORMATION: 'n' stands for unidentified base.

<400> SEQUENCE: 23
ccggcgtccg gcagatgcac gcggggcggg ggccggggga gaggcgggga gagagaaccc      60
acaacaaaac ttggctcgct cgcccacagg ctcgacttga atgacaggag ccggcgcccg     120
cggagcgcag cggacacccg cgagcctgtt ccgcccacgg cgcggcgcgc agcggcaggt     180
gctggcaagg gccagtggca tcagatcccc cagagctggg gttacaggtg gttgtgagtc     240
atcccagaga gtgctgggct cagtcttctg tgagcagagc actgtcttaa acagataagc     300
ttgtggactt ttatggagac aagccaaagg tgagagaaga aagccagcct gtccagcacc     360
atggctggca gcaggggcct gccactccta ctgctggtgc ttcagctctt cctgggccct     420
gtgctgcctg tgagggcacc tgtgtttggc cgaagtgaca cccccaccct gagccccgag     480
gagaatgaat tgtggagga agagaatcag ccagtgctgg ttctgagctc cgaggagcca     540
gagcctggcc agccactgtc gactgtcccg agattggtgc tgttccagg aaggtgtatg     600 gactgtggtg gcattgacct gcgtgagttt cangggaact gccgagcaca ccaaccatct     660
tctcttgcag aaaaaccagn tngagaaaat c                                    691

<210> SEQ ID NO 24
<211> LENGTH: 572
<212> TYPE: DNA
<213> ORGANISM: Mus musculus

<400> SEQUENCE: 24
gctgctgtca ggtggtccct tttatggtgg gttcctgtgg tcgctgcgca gcggctggcc      60
```

-continued

```
gacttccgca gcgggtctcg ggccaccgag cgccgtcttc acccagcgcc atggctgtgg    120
ccgctgtcgg ccgcccgaga gccctgcgct gcccgctgtt gctcctgctg tcactcctgc    180
tggtagccgg ccctgcgctg gctggaacg accctgacag aatactcttg cgggatgtga     240
aagctcttac cctctactcc gaccgctaca ccacctcccg gaggctggac cctatcccac    300
agttgaagtg tgttggaggc accgccggtt gtgaggccta tacccccagg gtgatacagt    360
gccagaacaa aggctgggat ggctacgatg tacagtggga atgtaagacc gacttggata    420
ttgcatacaa atttggcaaa actgtggtga gctgtgaagg ctacgagtcc tctgaagacc    480
agtatgtcct caggggttcc tgcggcttgg agtacaactt agattacaca gagctgggcc    540
tgaagaaact gaaggagcgc ggccgcgtcg ac                                  572
```

<210> SEQ ID NO 25
<211> LENGTH: 877
<212> TYPE: DNA
<213> ORGANISM: Mus musculus
<220> FEATURE:
<221> NAME/KEY: misc_feature
<222> LOCATION: (662)..(662)
<223> OTHER INFORMATION: 'n' stands for unidentified base.

<400> SEQUENCE: 25

```
ctccgccgca gttctcggtg ggtcgccggg cagccctccc gccatgcacc tgctgcttgc     60
agccgcgttc gggctgctgc tgctgctgcc gccgccgggg ccgtagcct cccggaagcc    120 gacgatgtgc cagagatgcc ggacgctggt ggacaagttc aaccagggga tggccaacac   180
ggccaggaag aatttcggtg gcggcaacac ggcgtgggaa gagaagacgc tgtctaagta   240
cgaattcagt gagatccggc ttctggagat catggagggt ctgtgtgaca gcagtgactt   300
tgagtgcaac caactcttgg agcagcagga ggagcagcta gaggcttggt ggcagacact   360
gaagaaggag caccccaacc tatttgagtg gttctgtgta cacacactga agcgtgctg    420 tcttccaggc acctacgggc cagactgtca agagtgccag ggtgggtccg agaggccttg    480
cagcggaaac ggctattgca gcggagacg cagcagacag ggcgacgggt cctgccagtg    540
tcacacaggc tacaagggac cactgtgtat tgactgcaca gacggcttct tcagcttgca    600
gaggaacgag acccacagca tctgctcagc ctgtgatgag tcttgcaaga cctgctctgg    660
tncaagcaac aaagactgta tccagtgtga agtgggctgg gcacgtgtgg aggatgcctg    720
tgtggatgtg gatgagtgtg cagcagagac atctccgtgc agcgatggcc agtactgtga    780
gaatgtcaac ggctcgtaca catgtgaaga ctgtgattct acctgcgtgg gctgtacagg   840
aaaaggccca gccaactgta aggagtgtat tgccggc                             877
```

<210> SEQ ID NO 26
<211> LENGTH: 930
<212> TYPE: DNA
<213> ORGANISM: Mus musculus

<400> SEQUENCE: 26

```
aggggacccg cggcacgagc gagagctcgc cagccccgcc acgatgcccc cgcgcccagg     60
acgcctcctc cagccgctgg ccgggctgcc ggccctggcc acgctcctgc tgctgctcgg    120
ggcgcgcaaa ggcgcccggg cccaggaggt ggaagcggac agcggggtcg agcaggaccc    180
gcacgccaag cacctgtata cggccgacat gttcacgcac gggatccaga gcgccgcgca    240
cttcgtcatg ttcttcgcgc cctggtgtgg acactgccag cggctgcagc caacttggaa    300
```

```
tgacctggga gacaagtaca acagcatgga ggatgccaag gtctacgtgg ccaaagtgga    360
ctgcacggct gattccgacg tgtgctctgc ccagggagtg cgaggatacc ccaccctgaa    420
gttttttaag cctggacaag aagcagtgaa gtaccagggt cctagagact ttgaaacact    480
ggaaaactgg atgctgcaga cactgaacga ggagccagcc acaccggagc cggaagcgga    540
accacccaga gcccctgagc tcaaacaggg gttgtatgag ctctcggcca acaactttga    600
gctgcatgtt tctcaaggca accactttat caagttcttc gctccgtggt gcggtcactg    660
caaagctctg gctccaacct gggagcagct ggctctgggc cttgaacatt ctgaaaccgt    720
caagattggc aaggttgact gcacgcagca ctacgctgtc tgctcagagc atcaggtcag    780
aggctatcca actctgctct ggtttcgaga tggcaagaag gtggatcagt acaagggaaa    840
gcgggacttg gagtcactga gagactatgt gcagtcccag ctgcagggtt cagaggcagc    900
tccggagact gttgagccgt cagaggcccc                                     930
```

<210> SEQ ID NO 27  
<211> LENGTH: 641  
<212> TYPE: DNA  
<213> ORGANISM: Mus musculus  
<220> FEATURE:  
<221> NAME/KEY: misc_feature  
<222> LOCATION: (325)..(325)  
<223> OTHER INFORMATION: 'n' stands for unidentified base.  
<220> FEATURE:  
<221> NAME/KEY: misc_feature  
<222> LOCATION: (329)..(329)  
<223> OTHER INFORMATION: 'n' stands for unidentified base.

<400> SEQUENCE: 27

```
aggggcggga ccgggcgggt tgcggagggt aggcacgcgg aggccgggcc atgcgtgcgg     60
gccggtgtgc cgcggcgctg ctgctgctgc tactgagcgg cgcggggcgc gcgatcggct    120
ccgaggacat cgtggtaggc tgcgggggtt tcgtgaagtc ggacgtggag atcaactact    180
cgctcatcga gataaagtta tacaccaagc atgggacttt gaaatatcag acggactgtg    240
ctcctaacaa cggctacttt atgatcccct tgtatgataa gggggatttc atcctgaaga    300
tcgaacctcc tctgggctgg agttntganc caaccaacgt gtagctgcga gtggatggtg    360
tgagcgacat ctgcacgaag ggcgggggaca tcaacttcct attcactggc ttctctgtga    420
atggcaaggt cctcagcaaa gggcagcccc tgggcccagc aggagttcag gtatccctga    480
gaagcaccgg tgctgactcg aagatccagt ctacagtcac gcagcctggc ggaaagtttg    540
cgttttccca agttcttcct ggagattatg aaatccttgc aactcacccg acctgggccc    600
tgaaggaggc aagtaccacg gtgcgtgtga cgaactcgaa t                        641
```

<210> SEQ ID NO 28  
<211> LENGTH: 703  
<212> TYPE: DNA  
<213> ORGANISM: Mus musculus

<400> SEQUENCE: 28

```
gcgcgtcgcg gaccccgcc tgggcctcca gtgggacagc ctccctgggg gctttggcag      60
gtgtcacttc ttcaccttgg cgtcataggt gcctgcgttt ttgtaggcac tcacgtagcc    120
actgtcgtcc aggatgtcct gccgtccagc gatgcccttt cccttgccgc tctcatcaaa    180
gcgttctttg tgggagcccg tatacttact ggtgtccgtc agccggtcca cagcaccacc    240
cgttttagct ttggtgacgc caatgttggc cggttccttg cccgctatca gctggcagat    300
ggcatcaaag gcctcctcct tggacttccc cttgaaccgc ttagttgcca gctcttccag    360
```

| | |
|---|---|
| ggccttcttg aactcctcat agttgattac tctagcagat ttcgccttga ctttggagaa | 420 |
| gacgatgtcg acgtcggtgc ccgttacggc ctttccgtcg gccaccttac agtccttgca | 480 |
| cagcttggcc cagttcttgc cattcatctc ttgcccgctg gccttggggt cgccatggat | 540 |
| ggcaaacttc cggaagctct cctccagccc agctatgtcc gtgctcgctg ccatgccacc | 600 |
| cggcttctac cgcttggctg ctcctgagcg tgccttcgga caggaccag gaactgatgc | 660 |
| tggagaccag gaggctccac agctccgctc cctgccggct ccc | 703 |

<210> SEQ ID NO 29
<211> LENGTH: 934
<212> TYPE: DNA
<213> ORGANISM: Mus musculus
<220> FEATURE:
<221> NAME/KEY: misc_feature
<222> LOCATION: (605)..(605)
<223> OTHER INFORMATION: 'n' stands for unidentified base.

<400> SEQUENCE: 29

| | |
|---|---|
| ccgaggttca agaggagcct agggagtggc agctctcgct gaccggcggg tcccagagac | 60 |
| ctgcccccaa ggtgtcccac tgtgtggcta agggtgggat agaacccggg ctgggagagc | 120 |
| cgggttatgg gttccagtgg tggttccgcc gcttccttgc ttcgctctgt cttacctcgg | 180 |
| cgttcagcct attttcctc gtaagaattg gacactttc cgtgcccctt ccataccgca | 240 |
| ggtggtgttc gtagaggctc tcacgctttt caaaaggcgt ctcatctaag acttgctaga | 300 |
| accaacctga ctaaaggagt caccgtcata ccccccttgc acctggagta aatctgactg | 360 |
| tccgaaggac gaaggaccgg tctgtgagca cttgtgctaa ggtggacttt attcacactc | 420 |
| ctgagtggaa tattatttgt cactcactcc tgagtcctgc cgtttggagg ggctgccttt | 480 |
| ggaaatgagt tctgggaact gaacacagga actgggtgcc tgtaccaggc ttgccatttg | 540 |
| cctgaccgag ttactcttct ttggatcccg gcgctgcagt acttttgaat tgttcctgtg | 600 |
| aaggncagaa gtaggtattt ggtcccttgg agctgtgagc tgatgtaggt gctgggaact | 660 |
| cagctgtggt gtgctgcaag accaaggacg agtcttgcag tgttaagtgt tttcctcagg | 720 |
| gtgctcagac ggtgaaaatc agagatcagg ccacctttct gtgagccttc agctgagtct | 780 |
| aaaggtgtta ttgatcagaa tggcttcagg atggttttac ctgtcctgca tggtgctggg | 840 |
| atcgctggga tcgatgtgca tcctcttcac tgcctactgg atgcagtact ggcgcggtgg | 900 |
| ctttgcctgg gatggcacgg tgctcatgtt taac | 934 |

<210> SEQ ID NO 30
<211> LENGTH: 812
<212> TYPE: DNA
<213> ORGANISM: Mus musculus
<220> FEATURE:
<221> NAME/KEY: misc_feature
<222> LOCATION: (589)..(589)
<223> OTHER INFORMATION: 'n' stands for unidentified base.

<400> SEQUENCE: 30

| | |
|---|---|
| ggaggctgag gcaagaggga gctgtccggg tggggagcca gcacttcctt cttcctcctc | 60 |
| tgcgtgaggg gagagaaggt tggggtccc cgagcccatg gatcgggagg aggcggaggc | 120 |
| cgccgagagc cggcacccct ctatgtggcc ctgagccccg tgtactggtt ccgcctctct | 180 |
| ggaaggccat ggagaagaga ctgggagtca agccaagtcc cgcttcctgg gttttgccag | 240 |
| gatattgttg gcagacatca gtgaagctgc cgagaagcct gtacctgctt tacagttttct | 300 |

```
tctgcttcag cgttctgtgg ttgtcaacag atgctgatga gagcagatgc caacaggga      360 agacacttta tggagctggc ttgagaactg agggagaaaa tcacctccgg cttcttgcag     420
gaagcctgcc tttccacgcc tgtcgggctg cctgctgccg ggactctgcc tgccacgctc     480
tatggtggct ggaagggatg tgctttcagg ctgactgcag taagcccag agctgccagc     540 cttttaggac agactcttcc aattccatgc tgatcatttt tcaaaaatnc caaactacag     600
atgatttggg ccttctgcct gaagatgatg aaccacatct tctgaggcta ggctggggca     660
ggacatcgtg gaggaggcag agccttcttg gggctcccct caccctttct gtaccctcta     720
gtcaccacca gagcttactc agggatcggc agaagagaga tctcagtgtg gtacctacac     780
atggagcgat gcagcattct aaagtgaatc ac                                   812
```

<210> SEQ ID NO 31
<211> LENGTH: 19
<212> TYPE: DNA
<213> ORGANISM: Artificial Sequence
<220> FEATURE:
<223> OTHER INFORMATION: Oligonucleotide designed to act as primer for
      amplifying cDNA fragment of secretory or membrane proteins derived
      from mouse white adipose tissue.

<400> SEQUENCE: 31
gggggtggac catcctcta                                                  19

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide designed to act as primer for
      amplifying cDNA fragment of secretory or membrane proteins derived
      from mouse white adipose tissue.

<400> SEQUENCE: 32
cgcgcagctg taaacggtag                                                 20

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST20-14.

<400> SEQUENCE: 33
caggcccctg ctgccagcca t                                               21

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST20-14.

<400> SEQUENCE: 34
atgcacgcgg ggcgggggcc                                                 20

<210> SEQ ID NO 35
<211> LENGTH: 21
<212> TYPE: DNA
<213> ORGANISM: Artificial Sequence

```
<220> FEATURE:
<223> OTHER INFORMATION: Oligonucleotide designed to act as 5'-RACE
      gene-specific primer for identifying base sequence encoding full
      length mSST22-22.

<400> SEQUENCE: 35
gcgaccacag gaacccacca t                                              21

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST22-22.

<400> SEQUENCE: 36
atggtgggtt cctgtggtcg                                                20

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST8-5.

<400> SEQUENCE: 37
ggctgcaagc agcaggtgca t                                              21

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST8-5.

<400> SEQUENCE: 38
atgcacctgc tgcttgcagc                                                20

<210> SEQ ID NO 39
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST19-15.

<400> SEQUENCE: 39
gcgtcctggg cgcgggggca t                                              21

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST19-15.

<400> SEQUENCE: 40
atgcccccgc gcccaggacg                                                20
```

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST13-11.

<400> SEQUENCE: 41
ggcacaccgg cccgcacgca t                                           21

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST13-11.

<400> SEQUENCE: 42
atgcgtgcgg gccggtgtgc                                             20

<210> SEQ ID NO 43
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST9-8.

<400> SEQUENCE: 43
tatgtccgtg ctcgctgcca t                                           21

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST9-8.

<400> SEQUENCE: 44
atgtcctgcc gtccagcgat                                             20

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST21-3.

<400> SEQUENCE: 45
gtaaaaccat cctgaagcca t                                           21

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST21-3.

```
<400> SEQUENCE: 46
atgggttcca gtggtggttc                                              20

<210> SEQ ID NO 47
<211> LENGTH: 21
<212> TYPE: DNA
<213> ORGANISM: Artificial Sequence
<220> FEATURE:
<223> OTHER INFORMATION: Oligonucleotide designed to act as 5'-RACE
      gene-specific primer for identifying base sequence encoding full
      length mSST20-6.

<400> SEQUENCE: 47
gactcccagt ctcttctcca t                                            21

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide designed to act as 3'-RACE
      gene-specific primer for identifying base sequence encoding full
      length mSST20-6.

<400> SEQUENCE: 48
atggatcggg aggaggcgga                                              20
```

PROTEINS AND USE THEREOF

This application is a divisional of U.S. patent application Ser. No. 10/520,783, filed Aug. 9, 2005, now abandoned, which is a national stage application of PCT International Application No. PCT/JP03/08690, filed Jul. 9, 2003, which claims priority to Japanese Application No. 2002-201856, filed Jul. 10, 2002, all of which are incorporated herein by reference.

TECHNICAL FIELD

The present invention relates to a novel secretory or membrane protein or a salt thereof which is derived from mouse white adipocyte, DNA encoding the same, and use thereof.

BACKGROUND ART

Generally, overweight people having accumulated visceral fat are more likely to have diabetes and vascular diseases such as hypertension and arteriosclerosis. Thus, it is considered that visceral fat accumulation is a common base for triggering the development of pathologic conditions. In the development of the pathologic conditions by the fat accumulation, proteins made by adipocytes are considered to be involved, and it has been shown that a gene which is expressed into a fat tissue has a high frequency of secretory protein genes, among which a gene of a biologically active substance such as complement and growth factor is included. Such a substance (also referred to as adipocytokine) essentially plays an important role in the metabolism of adipocyte itself, but is considered to have an adverse effect on the overall metabolism of a subject by causing excessive secretion or conversely insufficient secretion during fat accumulation. For example, Shimomura et al. have shown that plasminogen activator inhibitor-1 (PAI-1), an important regulation factor of fibrinolytic system, is expressed in a remarkably increased amount especially in visceral fat if fat accumulation occurs, and thereby increasing its blood concentration, which can be one of the factors for vascular complication [Shimomura, I. et al., "Nature medicine (Nat. Med.)", (USA), Vol. 2 (No. 7), pp. 800-803 (1996)]. It has been also shown that a gene which is specifically and expressed with high frequency in fat tissues, adipose most abundant gene transcript-1 encoding collagen-like protein (adiponectin), exists abundantly in human blood and has the action of strongly inhibiting the growth of vascular smooth muscle cell, but conversely has such a low level in blood of overweight people that it leads to the development of vascular diseases [Arita, Y. et al., "Biochemical and Biophysical Research Communications (Biochem. Biophys. Res. Commun.)", (USA), Vol. 257 (No. 1), pp. 79-83 (1999)].

It has also been suggested that adipocytes perform fat degradation as well as synthesis of large amount of fats, and release fatty acid and glycerol into the blood, but aquaporin adipose which is a membrane protein and cloned by Kuriyama et al., is likely to serve as glycerol channel molecule in the adipocytes [Kishida, K. et al., "Journal of Biological Chemistry (J. Biol. Chem.)", (USA), Vol. 275 (No. 27), pp. 20896-20902 (2000)].

As described above, the adipocytes secret various biologically active substances (i.e., ligand), and also express a membrane protein (i.e., receptor) on the cell surface. Thus, by regulating the expression or biological activities of such secretory or membrane protein, the development of a novel method of preventing and/or treating obesity, diabetes and vascular disease (e.g., arteriosclerosis) can be expected.

Conventionally, a substance which inhibits the binding of a biologically active substance (i.e., ligand) to a cell surface receptor and a substance which is bound and induces signal transduction like the biologically active substance (i.e., ligand) have been used as medicines regulating biological functions as a specific antagonist or agonist for such receptors. Accordingly, as described above, the discovery of a novel membrane receptor protein and a ligand molecule thereof (e.g., secretory protein) which are important in the expression in the living body and also can be a target for drug development, and cloning of its gene (e.g. cDNA), can be very important means for discovering a specific ligand, agonist, and antagonist of the novel receptor protein, or a specific receptor of the novel secretory protein.

However, all of the proteins secreted from adipocyte or expressed on the cell surface have not been discovered, and many of the secretory or membrane proteins are unknown at present, and thus search for a novel ligand or a receptor and elucidation of its function are strongly desired.

Therefore, an object of the present invention is to identify a novel secretory or membrane protein gene which is specifically and highly expressed in adipocyte, which can be a useful tool for developing prophylactic and/or therapeutic agents for obesity, diabetes, arteriosclerosis, etc., or a useful diagnosis marker for such diseases. Further, another object of the present invention is to provide a recombinant vector containing the novel gene, a transformant having the recombinant vector, a method of producing the secretory or membrane protein by cultivating the transformant, an antibody for the secretory or membrane protein, its partial peptide or a salt thereof, a compound for changing the amount of expression of the secretory or membrane protein, a method of determining a biological substance having specific affinity for the secretory or membrane protein, a method of screening a compound (antagonist and agonist) or a salt thereof for changing the binding property between the biological substance having specific affinity and the secretory or membrane protein, a kit for the screening, a compound for changing the binding property between the biological substance having specific affinity and the secretory or membrane protein (antagonist and agonist) or a salt thereof, which is obtained by using the method of screening or the screening kit, and a medicine comprising the compound for changing the binding property between the biological substance having specific affinity and the secretory or membrane protein (antagonist and agonist) or the compound for changing the expression amount of the secretory or membrane protein or a salt thereof, etc.

DISCLOSURE OF INVENTION

To achieve the above-mentioned object, the present inventors have constructed a cDNA library derived from visceral fat tissue of high fat food-loaded mice, constructed a retrovirus expression library in which the cDNA is incorporated into the 5' side of cDNA of constant and active form thrombopoietin receptor (serine at 498 position is substituted by asparagine) in which extracellular region at N-terminus is deleted, collected a high titer retrovirus from a packaging cell and infected mouse proBcell strain (Ba/F3), to select cells having growing property. The present inventors have extracted genome DNA from the selected cells, subcloned mouse adipocyte-derived cDNA introduced using PCR method, and determined the base sequence. As a result, the present inventors have identified eight cDNA fragments which are considered to encode unknown secretory or membrane proteins. Using such cDNA fragments, the present inventors have isolated the cDNA clone comprising a whole length of the protein code region from mouse adipocyte-derived cDNA, sequenced its base sequence, to find that all of them are novel genes.

Further, the present inventors have analyzed these genes in tissue specificity of expression, expression amount change in obesity and/or diabetes model, response for diet, response for insulin resistance causing factor or an insulin resistance ameliorating agent, effects for adipocyte differentiation, etc., and as results, have found that these genes are associated with adipocyte differentiation and glucose and/or lipid metabolism function.

Based on these findings, the present inventors have made further extensive study, and as results, have completed the present invention.

That is, the present invention provides:

[1] a protein comprising an amino acid sequence which is the same or substantially the same as the amino acid sequence represented by SEQ ID NO: 2, its partial peptide or a salt thereof;

[2] a polynucleotide comprising a base sequence encoding the protein or its partial peptide as described in [1];

[3] a polynucleotide comprising a base sequence which is complementary to the polynucleotide as described in [2] or an initial transcription product generating the polynucleotide as a result of processing, or a part thereof;

[4] an antibody for the protein, its partial peptide or a salt thereof as described in [1];

[5] a protein comprising an amino acid sequence which is the same or substantially the same as the amino acid sequence represented by SEQ ID NO: 4, its partial peptide or a salt thereof;

[6] a polynucleotide comprising a base sequence encoding the protein or its partial peptide as described in [5];

[7] a polynucleotide comprising a base sequence which is complementary to the polynucleotide as described in [6] or an initial transcription product generating the polynucleotide as a result of processing, or a part thereof;

[8] an antibody for the protein, its partial peptide or a salt thereof as described in [5];

[9] a protein comprising an amino acid sequence which is the same or substantially the same as the amino acid sequence represented by SEQ ID NO: 6, its partial peptide or a salt thereof;

[10] a polynucleotide comprising a base sequence encoding the protein or its partial peptide as described in [9];

[11] a polynucleotide comprising a base sequence which is complementary to the polynucleotide as described in [10] or an initial transcription product generating the polynucleotide as a result of processing, or a part thereof;

[12] an antibody for the protein, its partial peptide or a salt thereof as described in [9];

[13] a protein comprising an amino acid sequence which is the same or substantially the same as the amino acid sequence represented by SEQ ID NO: 8, its partial peptide or a salt thereof;

[14] a polynucleotide comprising a base sequence encoding the protein or its partial peptide as described in [13];

[15] a polynucleotide comprising a base sequence which is complementary to the polynucleotide as described in [14] or an initial transcription product generating the polynucleotide as a result of processing, or a part thereof;

[16] an antibody for the protein, its partial peptide or a salt thereof as described in [13];

[17] a protein comprising an amino acid sequence which is the same or substantially the same as the amino acid sequence represented by SEQ ID NO: 10, its partial peptide or a salt thereof;

[18] a polynucleotide comprising a base sequence encoding the protein or its partial peptide as described in [17];

[19] a polynucleotide comprising a base sequence which is complementary to the polynucleotide as described in [18] or an initial transcription product generating the polynucleotide as a result of processing, or a part thereof;

[20] an antibody for the protein, its partial peptide or a salt thereof as described in [17];

[21] a protein comprising an amino acid sequence which is the same or substantially the same as the amino acid sequence represented by SEQ ID NO: 12, its partial peptide or a salt thereof;

[22] a polynucleotide comprising a base sequence encoding the protein or its partial peptide as described in [21];

[23] a polynucleotide comprising a base sequence which is complementary to the polynucleotide as described in [22] or an initial transcription product generating the polynucleotide as a result of processing, or a part thereof;

[24] an antibody for the protein, its partial peptide or a salt thereof as described in [21];

[25] a protein comprising an amino acid sequence which is the same or substantially the same as the amino acid sequence represented by SEQ ID NO: 14, its partial peptide or a salt thereof;

[26] a polynucleotide comprising a base sequence encoding the protein or its partial peptide as described in [25];

[27] a polynucleotide comprising a base sequence which is complementary to the polynucleotide as described in [26] or an initial transcription product generating the polynucleotide as a result of processing, or a part thereof;

[28] an antibody for the protein, its partial peptide or a salt thereof as described in [25];

[29] a protein comprising an amino acid sequence which is the same or substantially the same as the amino acid sequence represented by SEQ ID NO: 16, its partial peptide or a salt thereof;

[30] a polynucleotide comprising a base sequence encoding the protein or its partial peptide as described in [29];

[31] a polynucleotide comprising a base sequence which is complementary to the polynucleotide as described in [30] or an initial transcription product generating the polynucleotide as a result of processing, or a part thereof;

[32] an antibody for the protein, its partial peptide or a salt thereof as described in [29];

[33] a protein comprising an amino acid sequence which is the same or substantially the same as the amino acid sequence represented by SEQ ID NO: 18, its partial peptide or a salt thereof;

[34] a polynucleotide comprising a base sequence encoding the protein or its partial peptide as described in [33];

[35] a polynucleotide comprising a base sequence which is complementary to the polynucleotide as described in [34] or an initial transcription product generating the polynucleotide as a result of processing, or a part thereof;

[36] an antibody for the protein, its partial peptide or a salt thereof as described in [33];

[37] a protein comprising an amino acid sequence which is the same or substantially the same as the amino acid sequence represented by SEQ ID NO: 20, its partial peptide or a salt thereof;

[38] a polynucleotide comprising a base sequence encoding the protein or its partial peptide as described in [37];

[39] a polynucleotide comprising a base sequence which is complementary to the polynucleotide as described in [38] or an initial transcription product generating the polynucleotide as a result of processing, or a part thereof;

[40] an antibody for the protein, its partial peptide or a salt thereof as described in [37];
[41] a protein comprising an amino acid sequence which is the same or substantially the same as the amino acid sequence represented by SEQ ID NO: 22, its partial peptide or a salt thereof;
[42] a polynucleotide comprising a base sequence encoding the protein or its partial peptide as described in [41];
[43] a polynucleotide comprising a base sequence which is complementary to the polynucleotide as described in [42] or an initial transcription product generating the polynucleotide as a result of processing, or a part thereof;
[44] an antibody for the protein, its partial peptide or a salt thereof as described in [41];
[45] a medicine comprising the protein, its partial peptide or a salt thereof as described in any one of [1], [5], [9], [13], [17], [21], [25], [29], [33], [37] and [41];
[46] a medicine comprising the polynucleotide as described in any one of [2], [6], [10], [14], [18], [22], [26], [30], [34], [38] and [42];
[47] a medicine comprising the polynucleotide as described in any one of [3], [7], [11], [15], [19], [23], [27], [31], [35], [39] and [43];
[48] a medicine comprising the antibody as described in any one of [4], [8], [12], [16], [20], [24], [28], [32], [36], [40] and [44];
[49] the medicine as described in any one of [45] to [48], which is a prophylactic and/or therapeutic agent for diseases involving abnormality of adipocyte differentiation and/or metabolism function;
[50] a diagnostic agent comprising the polynucleotide as described in any one of [2], [6], [10], [14], [18], [22], [26], [30], [34], [38] and [42] or a part thereof;
[51] a diagnostic agent comprising the polynucleotide as described in any one of [3], [7], [11], [15], [19], [23], [27], [31], [35], [39] and [43];
[52] a diagnostic agent comprising the antibody as described in any one of [4], [8], [12], [16], [20], [24], [28], [32], [36], [40] and [44];
[53] a diagnostic agent as described in any one of [50] to [52] for diagnosing diseases involving abnormality of adipocyte differentiation and/or metabolism function;
[54] a method of screening a compound or a salt thereof having specific affinity for the protein or a salt thereof as described in any one of [1], [5], [9], [13], [17], [21], [25], [29], [33], [37] and [41], or a compound or a salt thereof changing binding property between the protein or a salt thereof and the compound or a salt thereof, which comprises using said protein, its partial peptide or a salt thereof;
[55] a kit for screening a compound or a salt thereof having specific affinity for the protein or a salt thereof as described in any one of [1], [5], [9], [13], [17], [21], [25], [29], [33], [37] and [41], or a compound or a salt thereof changing binding property between the protein or a salt thereof and the compound or a salt thereof, which comprises said protein, its partial peptide or a salt thereof;
[56] a medicine comprising a compound or a salt thereof obtained by using the method as described in [54] or the kit as described in [55];
[57] the medicine as described in [56], which is a prophylactic and/or therapeutic agent for diseases involving abnormality of adipocyte differentiation and/or metabolism function;
[58] a method of screening a compound or a salt thereof changing the expression amount of a gene encoding the protein as described in any one of [1], [5], [9], [13], [17], [21], [25], [29], [33], [37] and [41], which comprises using the polynucleotide as described in any one of [2], [6], [10], [14], [18], [22], [26], [30], [34], [38] and [42] or a part thereof;
[59] a kit for screening a compound or a salt thereof changing the expression amount of gene encoding the protein as described in any one of [1], [5], [9], [13], [17], [21], [25], [29], [33], [37] and [41], which comprises the polynucleotide as described in any one of [2], [6], [10], [14], [18], [22], [26], [30], [34], [38] and [42] or a part thereof;
[60] a medicine comprising a compound or a salt thereof obtained by using the method as described in [58] or the kit as described in [59];
[61] the medicine as described in [60], which is a prophylactic and/or therapeutic agent for diseases involving abnormality of adipocyte differentiation and/or metabolism function;
[62] a method of screening a compound or a salt thereof changing the amount of the protein or a salt thereof as described in any one of [1], [5], [9], [13], [17], [21], [25], [29], [33], [37] and [41] on the cell membrane or in the extracellular fluid, which comprises using the antibody as described in any one of [4], [8], [12], [16], [20], [24], [28], [32], [36], [40] and [44];
[63] a kit for screening a compound or a salt thereof changing the amount of the protein or a salt thereof as described in any one of [1], [5], [9], [13], [17], [21], [25], [29], [33], [37] and [41] on the cell membrane or in the extracellular fluid, which comprises the antibody as described in any one of [4], [8], [12], [16], [20], [24], [28], [32], [36], [40] and [44];
[64] a medicine comprising a compound or a salt thereof obtained by using the method as described in [62] or the kit as described in [63];
[65] the medicine as described in [64], which is a prophylactic and/or therapeutic agent for diseases involving abnormality of adipocyte differentiation and/or metabolism function;

and the like.

The protein of the present invention is a secretory or membrane protein, etc. expressed in white adipocyte by loading high fat food, and therefore has excellent effects as a prophylactic and/or therapeutic agent for diseases associated with adipocyte differentiation and metabolism function, or as a tool for screening a drug-candidate compound which is effective for preventing and/or treating the diseases.

BEST MODE FOR CARRYING OUT THE INVENTION

The present invention provides a secretory or membrane protein which is expressed specifically or highly in white fat tissue of human or other mammals loaded by high fat foods (hereinafter, sometimes referred to as the "protein of the present invention"). Specifically, the protein of the present invention is a protein comprising an amino acid sequence which is the same or substantially the same as the amino acid sequence represented by SEQ ID NO: 2 (hereinafter, sometimes referred to as "SST20-14 (Long form)"); a protein comprising an amino acid sequence which is the same or substantially the same as the amino acid sequence represented by SEQ ID NO: 4 (hereinafter, sometimes referred to as "SST20-14 (Short form)"); a protein comprising an amino acid sequence which is the same or substantially the same as the amino acid sequence represented by SEQ ID NO: 6 (hereinafter, sometimes referred to as "SST22-22 (Long form)"); a protein comprising an amino acid sequence which is the same or substantially the same as the amino acid sequence represented by SEQ ID NO: 8 (hereinafter, sometimes referred to as "SST22-22 (Short form)"); a protein comprising an amino acid sequence which is the same or substantially the same as the amino acid sequence represented by SEQ ID NO: 10 (hereinafter, sometimes referred to as "SST8-5"); a protein comprising an amino acid sequence which is the same or substantially the same as the amino acid sequence represented by SEQ ID NO: 12 (hereinafter, sometimes referred to as "SST19-15 (Long form)"); a protein comprising an amino acid sequence which is the same or substantially the same as the amino acid sequence represented by SEQ ID NO: 14 (hereinafter, sometimes referred to as "SST19-15 (Short form)"); a protein comprising an amino acid sequence which is the same or substantially the same as the amino acid sequence represented by SEQ ID NO: 16 (hereinafter, sometimes referred to as "SST13-11"); a protein comprising an amino acid sequence which is the same or substantially the same as the amino acid sequence represented by SEQ ID NO: 18 (hereinafter, sometimes referred to as "SST9-8"); a protein comprising an amino acid sequence which is the same or substantially the same as the amino acid sequence represented by SEQ ID NO: 20 (hereinafter, sometimes referred to as "SST21-3"); or a protein comprising an amino acid sequence which is the same or substantially the same as the amino acid sequence represented by SEQ ID NO: 22 (hereinafter, sometimes referred to as "SST20-6").

The protein of the present invention is a secretory or membrane protein which is highly expressed in fat tissue, especially in white fat tissue of mammals, and the source is not particularly limited as long as it has the above-mentioned properties, for example, it may be a protein isolated and purified from any cells [e.g., liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells or the corresponding precursor cells, stem cells, cancer cells, etc.], or from any tissues where such cells are present [e.g., brain or each region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, lung, gastrointestinal tract (e.g., large intestine and small intestine), blood vessel, heart, thymus, spleen, submandibular gland, peripheral blood, prostate, testis, ovary, placenta, uterus, bone, joint, fat tissue (e.g., brown fat tissue and white fat tissue), skeletal muscle, etc.] of mammals (e.g., human, mice, rats, rabbits, sheep, pigs, cattle, horses, cats, dogs, monkeys, chimpanzee, etc.). The protein may be also a protein which is synthesized chemically or biochemically under a cell-free translation system, or a recombinant protein produced from a transformant into which nucleic acid having a base sequence encoding the above-mentioned amino acid sequence is introduced.

The "substantially the same amino acid sequence" includes an amino acid sequence having a homology of about 70% or more, preferably about 80% or more, more preferably about 90% or more, and further more preferably about 95% or more to the amino acid sequence represented by each of the above-mentioned SEQ ID NOs (SEQ ID NO: 2, 4, 6, 8, 10, 12, 14, 16, 18, 20 or 22). As used herein, a "homology" means a proportion (%) of the same amino acid residue and analogous amino acid residue to the whole amino acid residues overlapped in the optimal alignment (preferably, the algorithm is such that a gap can be introduced into one or both of the sequences for an optimal alignment) where two amino acid sequences are aligned using a mathematic algorithm known in the technical field. The "analogous amino acid" means amino acids having similar physiochemical properties, and for example, the amino acids are classified into groups such as an aromatic amino acid (Phe, Trp, Tyr), an aliphatic amino acid (Ala, Leu, Ile, Val), a polar amino acid (Gln, Asn), a basic amino acid (Lys, Arg, His), an acidic amino acid (Glu, Asp), an amino acid having a hydroxy group (Ser, Thr) and an amino acid having a small side-chain (Gly, Ala, Ser, Thr, Met). Substitution by such analogous amino acids is expected not to change the phenotype of proteins (i.e., conservative amino acid substitution). Specific examples the conservative amino acid substitution is known in this technical field and are described in various literatures (e.g., see Bowie et al., Science, 247: 1306-1310 (1990)).

In the present specification, a homology of amino acid sequence can be calculated under the following conditions (an expected value=10; gap allowed; matrix=BLOSUM62; filtering=OFF) using a homology calculation algorithm NCBI BLAST (National Center for Biotechnology Information Basic Local Alignment Search Tool). Other algorithms to determine a homology of amino acid sequence include, for example, the algorithm as described in Karlin et al., Proc. Natl. Acad. Sci. USA, 90: 5873-5877 (1993) [the algorithm is incorporated into NBLAST and XBLAST programs (version 2.0) (Altschul et al., Nucleic Acids Res., 25: 3389-3402 (1997))], the algorithm as described in Needleman et al., J. Mol. Biol., 48: 444-453 (1970) [the algorithm is incorporated into a GAP program in a GCG software package], the algorithm as described in Myers and Miller, CABIOS, 4:11-17 (1988) [the algorithm is incorporated into an ALIGN program (version 2.0) which is a part of a CGC sequence alignment software package], the algorithm as described in Pearson et al., Proc. Natl. Acad. Sci. USA, 85: 2444-2448 (1988) [the algorithm is incorporated into a FASTA program in a GCG software package], etc., which can be preferably used in the same manner.

More preferably, the "substantially the same amino acid sequence" is an amino acid sequence having a homology of about 60% or more, preferably about 70% or more, further preferably about 80% or more, especially preferably about 90% or more to the amino acid sequence represented by each of the above-mentioned SEQ ID NOs.

Preferable examples of the "protein comprising substantially the same amino acid sequence" include a protein comprising the above-mentioned "substantially the same amino acid sequence" and having a substantially equivalent activity to that of the protein comprising the amino acid sequence represented by each of the above-mentioned SEQ ID NOs.

The "substantially equivalent activity" includes, for example, a receptor (or ligand) binding activity and signal transduction action, etc. The expression "substantially equivalent" means that the activity is inherently (e.g. physiologically or pharmacologically) equivalent. Therefore, although it is preferred that the activity such as a receptor (ligand) binding activity and a signal transduction action be equivalent (e.g., about 0.5- to about 2-fold), the quantitative factors such as a level of the activity, a molecular weight of the protein, etc. may differ.

Measurement of the activities such as a receptor (or a ligand) binding activity and a signal transduction action can be performed in accordance with per se known methods, for example, a method of determining a biological substance (receptor or ligand) having specific affinity and a method used in the screening method of agonist and antagonist which will be described later.

The protein of the present invention also includes, for example, a protein comprising (i) an amino acid sequence wherein one or more (preferably, 1 to 30 or so, preferably 1 to 10 or so and further preferably several (1 to 5) amino acids are deleted from the amino acid sequence represented by each of the above-mentioned SEQ ID NOs, (ii) an amino acid sequence wherein one or more (preferably, 1 to 30 or so, preferably 1 to 10 or so, further preferably several (1 to 5) amino acids are added to the amino acid sequence represented by each of the above-mentioned SEQ ID NOs, (iii) an amino acid sequence wherein one or more (preferably, 1 to 30 or so, preferably 1 to 10 or so, and further preferably several (1 to 5) amino acids are inserted into the amino acid sequence represented by each of the above-mentioned SEQ ID NOs, (iv) an amino acid sequence wherein one or more (preferably, 1 to 30 or so, preferably 1 to 10 or so, and further preferably several (1 to 5) amino acids by other amino acids are substituted in the amino acid sequence represented by each of the above-mentioned SEQ ID NOs, or (v) a combination of these amino acid sequences, and having a substantially equivalent activity to that of the protein comprising the amino acid sequence represented by each of the above-mentioned SEQ ID NOs. As used herein, the "substantially equivalent activity" has the same meanings as described above.

As described above, when the amino acid sequence is inserted, deleted or substituted, the position of insertion, deletion or substitution is not particularly limited as long as the activity of protein is retained.

The protein of the present invention is a secretory or membrane protein, and usually translated as a precursor polypeptide having signal peptide at N-terminus in the living body, and subjected to processing by signal peptidase to become mature (or pro) protein. The cleavage site (N-terminus of mature (pro) protein) of the signal peptide can be determined, for example, by subjecting the fully or partially purified protein of the present invention to Adman degradation, or can be estimated from the primary structure of the precursor polypeptide using a known mathematic algorithm. Such algorithm includes, for example, the algorithm as described in Nielsen et al., Int. Neural Syst., 8(5-6): 581-599 (1997) [the algorithm is incorporated into a Signal P program (available on a WWW server: www.cbs.dtu.dk/services/SignalP/)], the algorithm as described in Emanuelsson et al., J. Mol. Biol. 300: 1005-1016 (2000) [the algorithm is incorporated into a Target P program (available on a WWW server: www.cbs.dtu.dk/services/TargetP/)], the algorithm as described in von Heijne, Nucl. Acids Res., 14:4683 (1986) [the algorithm is incorporated into a PSORT II program (available on a WWW server: psort.ims.u-tokyo.ac.jp/form2.html)], the algorithm is incorporated into a SOSUI (Signal) program Beta Version (available on a WWW server: sosui.proteome.bio.tuat.ac.jp/cgi-bin/sosui.cgi?/sosuisignal/sosuisignal_submit.html), etc., but not limited thereto. For example, when the above-mentioned PSORT II program is used, the polypeptide having the amino acid sequence represented by each of the above-mentioned SEQ ID NOs is predicted to be cleaved between the amino acid No. −1 and the amino acid No. 1, respectively, but it does not mean that this always corresponds to the actual cleavage site, and the signal cleavage position may be changed by the cell species expressing the protein of the present invention. Accordingly, the protein of the present invention also comprises a protein comprising an amino acid sequence starting after the amino acid No. 1, among the amino acid sequences represented by each of the above-mentioned SEQ ID NOs, or an amino acid sequence wherein one or more amino acids are added or deleted from the amino acid sequence.

The protein of the present invention is preferably a mouse SST20-14 (Long form) having the amino acid sequence represented by SEQ ID NO: 2, mouse SST20-14 (Short form) having amino acid sequence represented by SEQ ID NO: 4, mouse SST22-22 (Long form) having amino acid sequence represented by SEQ ID NO: 6, mouse SST22-22 (Short form) having amino acid sequence represented by SEQ ID NO: 8, mouse SST8-5 having amino acid sequence represented by SEQ ID NO: 10, mouse SST19-15 (Long form) having amino acid sequence represented by SEQ ID NO: 12, mouse SST19-15 (Short form) having amino acid sequence represented by SEQ ID NO: 14, mouse SST13-11 having amino acid sequence represented by SEQ ID NO: 16, mouse SST9-8 having amino acid sequence represented by SEQ ID NO: 18, mouse SST21-3 having amino acid sequence represented by SEQ ID NO: 20 or mouse SST20-6 having amino acid sequence represented by SEQ ID NO: 22, or a homologue thereof in other mammals.

In the present specification, the proteins and the peptides are represented in accordance with a common way of describing the peptides, so that the N-terminus (amino terminus) is described at the left hand and the C-terminus (carboxyl terminus) is described at the right hand. In the proteins of the present invention including the protein comprising the amino acid sequence starting after the amino acid No. 1 among the amino acid sequences represented by SEQ ID NO: 2 or 4, any of a carboxyl group (—COOH), a carboxylate (—COO⁻), an amide (—CONH$_2$) or an ester (—COOR) may be at the C-terminus.

As used herein, R in the ester includes, for example, a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a phenyl-$C_{1-2}$ alkyl group, e.g., benzyl, phenethyl, etc., or a $C_{7-14}$ aralkyl group, e.g., an α-naphthyl-$C_{1-2}$-alkyl group such as α-naphthylmethyl, etc.; a pivaloyloxymethyl group and the like.

When the protein of the present invention has a carboxyl group (or carboxylate) at a position other than the C-terminus, it may be amidated or esterified and such an amide or ester is also included within the protein of the present invention. As the ester group herein, for example, the same esters as those described with respect to the above C-terminus are used.

Furthermore, examples of the protein of the present invention include those wherein the amino group of the amino acid residue at the N-terminus is protected with a protecting group (e.g., a $C_{1-6}$ acyl group e.g., a $C_{1-6}$ alkanoyl group such as a formyl group, an acetyl group, etc.); those wherein the glutamyl group at the N-terminal region, which may be cleaved in vivo, is pyroglutaminated; those wherein a substituent (e.g., —OH, —SH, an amino group, an imidazole group, an indole group, a guanidino group, etc.) on the side chain of an amino acid in the molecule is protected with a suitable protecting group (e.g., a $C_{1-6}$ acyl group e.g., a $C_{1-6}$ alkanoyl group such as a formyl group, an acetyl group, etc.), and conjugated proteins such as glycoproteins having sugar chains bound thereto.

Partial peptides of the protein of the present invention (hereinafter, sometimes abbreviated as the "partial peptide of the present invention") may be any peptides as long as they are the peptides having a partial amino acid sequence of the protein of the present invention and have substantially equivalent activity to that of the protein of the present invention. As used herein, the "substantially equivalent activity" has the same meanings as described above. Also, measurement of the "substantially equivalent activity" can be performed in the same manner as for the protein of the present invention.

Specifically, the partial peptide of the present invention includes, for example, one having a partial amino acid sequence further comprising a region for binding with a biological substance (receptor or ligand) which can interact with the protein of the present invention and a region for signal transduction mediated by such interaction, among the amino acid sequences represented by each of the above-mentioned SEQ ID NOs.

The partial peptide of the present invention is preferably a peptide having at least 30, preferably at least 60, and more preferably at least 100 amino acids.

On the other hand, a peptide which has a partial amino acid sequence of the protein of the present invention but does not have a substantially equivalent activity to said protein, for example, one having a partial amino acid sequence comprising a region for binding with a biological substance (receptor or ligand) which can interact with the protein of the present invention, but not comprising a region for signal transduction mediated by such interaction, among the amino acid sequence represented by each of the above-mentioned SEQ ID NOs, is not included in the "partial peptide of the present invention." However, such peptide can bind to a biological substance (receptor or ligand) which can interact with the protein of the present invention to block signal transduction action by the protein, and thereby can be useful for preventing and/or treating the conditions and/or diseases involving abnormal elevation of the signal transduction, etc.

Furthermore, in the partial peptide of the present invention, any of a carboxyl group (—COOH), carboxylate (—COO$^-$), amide (—CONH$_2$) or ester (—COOR) may be at the C-terminus. As used herein, R in the ester includes the above-mentioned ones for the protein of the present invention. When the partial peptide of the present invention has a carboxyl group (or carboxylate) at a position other than the C-terminus, it may be amidated or esterified and such an amide or ester is also included within the partial peptide of the present invention. As the ester group herein, the same esters as those described with respect to the above C-terminus are used.

Furthermore, examples of the partial peptide of the present invention include those wherein the amino group of the amino acid residue at the N-terminus is protected with a protecting group, those wherein the glutamine residue at the N-terminus is pyroglutaminated; those wherein a substituent on the side chain of an amino acid in the molecule is protected with a suitable protecting group, and conjugated peptides such as glycopeptides having sugar chains bound thereto, as well as the above-mentioned protein of the present invention.

Salts of the protein or its partial peptide of the present invention include physiologically acceptable salts with acids or bases, preferably physiologically acceptable acid addition salts. Examples of such salts include salts with inorganic acids (e.g., hydrochloric acid, phosphoric acid, hydrobromic acid and sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid and benzenesulfonic acid), etc.

The protein or a salt thereof of the present invention may be manufactured from the mammal cells or tissues described above by a per se known method for protein purification. Specifically, when the protein of the present invention is localized on the cell membrane, the protein or a salt thereof can be prepared by homogenizing tissues or cells of mammals, removing the cell debris by low-speed centrifugation, precipitating the fractions containing the cell membrane by centrifuging the supernatant at a high speed (if necessary, the cell membrane fraction is purified by density gradient centrifugation, etc.), and subjecting the fraction to chromatography such as reverse phase chromatography, ion exchange chromatography, affinity chromatography, etc. Also, when the protein of the present invention is secreted into the extracellular region, the protein or a salt thereof can be prepared by cultivating the tissue or cells of the mammals in a suitable medium, collecting the culture supernatant by filtration or centrifugation, etc., and subjecting the supernatant to chromatography, etc. in the same manner as described above.

The protein, its partial peptide or a salt thereof of the present invention (hereinafter, sometimes abbreviated as the "protein (peptide) of the present invention") also can be prepared according to a known method for peptide synthesis.

For the methods for peptide synthesis, for example, either solid phase synthesis or liquid phase synthesis may be used. That is, the partial peptide or amino acids that can construct the protein (peptide) of the present invention are condensed with the remaining part, and when the product contains a protecting group, this protecting group is removed to give a desired protein.

Condensation and elimination of the protecting groups can be conducted by per se known methods such as those described in (1) to (5) below.

(1) M. Bodanszky & M. A. Ondetti, Peptide Synthesis, Interscience Publishers, New York (1966)

(2) Schroeder & Luebke, The Peptide, Academic Press, New York (1965)

(3) Nobuo Izumiya, et al., Peptide Gosei-no-Kiso to Jikken (Basics and experiments of peptide synthesis), published by Maruzen Co. (1975)

(4) Haruaki Yajima & Shunpei Sakakibara, Seikagaku Jikken Koza (Biochemical Experiment) 1, Tanpakushitsu no Kagaku (Chemistry of Proteins) IV, 205 (1977)

(5) Haruaki Yajima, ed., Zoku Iyakuhin no Kaihatsu (A sequel to Development of Pharmaceuticals), Vol. 14, Peptide Synthesis, published by Hirokawa Shoten Thus obtained protein (peptide) can be purified and be isolated by known purification methods such as solvent extraction, distillation, column chromatography, liquid chromatography, recrystallization, a combination thereof, etc.

When thus obtained protein (peptide) is in a free form, the free form can be converted into a suitable salt form by a known method or an analogue thereto, and on the other hand, when the protein (peptide) is obtained in the form of a salt, it can be converted into the free form or in the form of a different salt by a known method or an analogue thereto.

To synthesize the protein (peptide) of the present invention, commercially available resins that are used for protein synthesis may be used. Examples of such resins include a chloromethyl resin, a hydroxymethyl resin, a benzhydrylamine resin, an aminomethyl resin, a 4-benzyloxybenzyl alcohol resin, a 4-methylbenzhydrylamine resin, a PAM resin, a 4-hydroxymethylmethylphenyl acetamidomethyl resin, a polyacrylamide resin, a 4-(2',4'-dimethoxyphenylhydroxymethyl)phenoxy resin, a 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective protein (peptide) according to various condensation methods known in the art. At the end of the reaction, the protein is excised from the resin and at the same time, the protecting groups are removed. Then, intramolecular disulfide bond-forming reaction is performed in a highly diluted solution to give the objective protein (peptide) or amides thereof.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminopropyl) carbodiimide, etc. For activation by these reagents, the protected amino acids in combination with a racemization inhibitor (e.g., HOBt and HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be appropriately chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; amines such as pyridine, etc.; ethers such as dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids can be acetylated with acetic anhydride or acetylimidazole.

The protection of the functional group which should not be involved in the reaction of the starting materials and the protecting group, and elimination of the protecting group, activation of the functional group involved in the reaction, etc. can be suitably selected from known groups or known means.

Examples of the protecting groups for the amino groups of the starting materials include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, for example, alkyl esterification (e.g., in the form of linear, branched or cyclic alkyl (e.g., methyl, ethyl, propyl, butyl, t-butyl, cyclopentyl, cyclohexyl, cycloheptyl, cyclooctyl, 2-adamantyl, etc.) esters, aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation or the like.

The hydroxyl group of serine can be protected through, for example, its esterification or etherification. Examples of the groups appropriately used for the esterification include a lower alkanoyl group such as an acetyl group, an aroyl group such as benzoyl group, and a group derived from carbonic acid such as a benzyloxycarbonyl group, an ethoxycarbonyl group, etc. Examples of a group appropriately used for the etherification include a benzyl group, a tetrahydropyranyl group, a t-butyl group, etc.

Examples of the groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

To eliminate (split off) the protecting groups, there are used a catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and a reduction with sodium in liquid ammonia. The elimination of the protecting group by the acid treatment described above is performed generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol and 1,2-ethanedithiol. Furthermore, a 2,4-dinitrophenyl group used as the protecting group for the imidazole of histidine is removed by a treatment with thiophenol. A formyl group used as the protecting group of the indole of tryptophan is eliminated by the above-mentioned acid treatment in the presence of 1,2-ethanedithiol or 1,4-butanedithiol, as well as by a treatment with an alkali such as a dilute sodium hydroxide solution and dilute ammonia.

Examples of the activated carboxyl groups in the starting materials include the corresponding acid anhydrides, azides, activated esters [(esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As one in which the amino groups are activated in the starting material, the corresponding phosphoric amides are employed.

In another method for obtaining the amides of the protein (peptide), for example, the α-carboxyl group of the carboxy terminal amino acid is first protected by amidation, and the peptide chain at the amino group side is then extended to a desired length. Thereafter, a protein (peptide) in which only the protecting group of the N-terminal α-amino group in the peptide chain has been eliminated and a protein (peptide) in which only the protecting group of the C-terminal carboxyl group has been eliminated are prepared. The two proteins (peptide) are condensed in a mixture of the solvents described above. The details of the condensation reaction are the same as described above. After the protected protein (protected peptide) obtained by the condensation is purified, all the protecting groups are eliminated by the method described above to give the desired crude protein (crude peptide). This crude protein (crude peptide) is purified by various known purification means. Lyophilization of the major fraction gives the amide of the desired protein (peptide).

The esterified protein (peptide) can be obtained by, for example, condensing the α-carboxyl group of the carboxy terminal amino acid with a desired alcohol to prepare an amino acid ester, which is followed by procedure similar to the preparation of the amidated protein (peptide) above.

The partial peptide or a salt thereof of the present invention can be also manufactured by cleaving the protein or a salt thereof of the present invention with an appropriate peptidase.

Further, the protein (peptide) of the present invention can be also produced by cultivating transformant comprising polynucleotide encoding the protein or its partial peptide of the present invention, and isolating and purifying the protein (peptide) of the present invention from the obtained culture mixture. The polynucleotide encoding the protein or its partial peptide of the present invention may be DNA or RNA, or DNA/RNA chimera, and preferably DNA. Also, the polynucleotide may be double stranded, or single stranded. When the polynucleotide is double stranded, it may be double stranded DNA, double stranded RNA or DNA: RNA hybrid. When the polynucleotide is single stranded, it may be sense strand (i.e., code strand), or antisense strand (i.e., non-code strand).

DNA encoding the protein or its partial peptide of the present invention includes genome DNA of mammals (e.g., human, horses, monkeys, cattle, pigs, sheep, goats, dogs, cats, guinea pigs, rats, mice, rabbits, hamsters, etc.), cDNA derived from any cells from the mammals [e.g., liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophage, T cells, B cells, natural killer cells, mast cells, neutrophil, basophil, eosinophil, monocyte), megakaryocyte, synovial cells, chondrocytes, bone cells, osteoblasts, osteoclasts, mammary gland cells, hepatocytes or interstitial cells, the corresponding precursor cells, stem cells, cancer cells, etc.)], or any tissues where such cells are present [e.g., brain or any region of the brain (e.g., olfactory bulb, amygdaloid nucleus, basal ganglia, hippocampus, thalamus, hypothalamus, cerebral cortex, medulla oblongata and cerebellum), spinal cord, hypophysis, stomach, pancreas, kidney, liver, gonad, thyroid, gall-bladder, bone marrow, adrenal gland, skin, lung, gastrointestinal tract (e.g., large intestine and small intestine), blood vessel, heart, thymus, spleen, submandibular gland, peripheral blood, prostate, testis, ovary, placenta, uterus, bone, joint, fat tissue (e.g., brown fat tissue and white fat tissue), skeletal muscle, etc.] synthetic DNA and the like. The genome DNA and cDNA encoding the protein or its partial peptide of the present invention can be directly amplified by Polymerase Chain Reaction (hereinafter, abbreviated as a "PCR methods") and Reverse Transcriptase-PCR (hereinafter, abbreviated as an "RT-PCR method") using genome DNA fractions and total RNA or mRNA fractions prepared from the above-mentioned cells and/or tissues, respectively as a template. The genome DNA and cDNA encoding the protein or its partial peptide of the present invention can be also cloned by a colony or plaque hybridization method, a PCR method and the like, respectively from genome DNA library and cDNA library which is prepared by inserting genome DNA and total RNA or mRNA fragment prepared by the above-mentioned cell and/or tissue into a suitable vector. The vector to be used for the library may be any of bacteriophage, plasmid, cosmid, phagemid, etc.

DNA encoding the protein of the present invention includes, for example, DNA comprising the base sequence represented by SEQ ID NO: 1 or DNA having a base sequence which hybridizes with the base sequence under highly stringent conditions and encoding a protein having substantially equivalent activity with the protein comprising amino acid sequence represented by SEQ ID NO: 2 (hereinafter, sometimes abbreviated as "Sst20-14 (Long form)"); DNA comprising base sequence represented by SEQ ID NO: 3 or DNA having a base sequence which hybridizes with the base sequence under highly stringent conditions and encoding a protein having substantially equivalent activity with protein comprising amino acid sequence represented by SEQ ID NO: 4 (hereinafter, sometimes abbreviated as "Sst20-14 (Short form)"); DNA comprising base sequence represented by SEQ ID NO: 5 or DNA having a base sequence which hybridizes with the base sequence under highly stringent conditions and encoding a protein having substantially equivalent activity with protein comprising amino acid sequence represented by SEQ ID NO: 6 (hereinafter, sometimes abbreviated as "Sst22-22 (Long form)"); DNA comprising base sequence represented by SEQ ID NO: 7 or DNA having a base sequence which hybridizes with the base sequence under highly stringent conditions and encoding a protein having substantially equivalent activity with protein comprising amino acid sequence represented by SEQ ID NO: 8 (hereinafter, sometimes abbreviated as "Sst22-22 (Short form)"); DNA comprising base sequence represented by SEQ ID NO: 9 or DNA having a base sequence which hybridizes with the base sequence under highly stringent conditions and encoding a protein having substantially equivalent activity with protein comprising amino acid sequence represented by SEQ ID NO: 10 (hereinafter, sometimes abbreviated as "Sst8-5"); DNA comprising base sequence represented by SEQ ID NO: 11 or DNA having a base sequence which hybridizes with the base sequence under highly stringent conditions and encoding a protein having substantially equivalent activity with protein comprising amino acid sequence represented by SEQ ID NO: 12 (hereinafter, sometimes abbreviated as "Sst19-15 (Long form)"); DNA comprising base sequence represented by SEQ ID NO: 13 or DNA having a base sequence which hybridizes with the base sequence under highly stringent conditions and encoding a protein having substantially equivalent activity with protein comprising amino acid sequence represented by SEQ ID NO: 14 (hereinafter, sometimes abbreviated as "Sst19-15 (Short form)"); DNA comprising base sequence represented by SEQ ID NO: 15 or DNA having a base sequence which hybridizes with the base sequence under highly stringent conditions and encoding a protein having substantially equivalent activity with protein comprising amino acid sequence represented by SEQ ID NO: 16 (hereinafter, sometimes abbreviated as "Sst13-11"); DNA comprising base sequence represented by SEQ ID NO: 17 or DNA having a base sequence which hybridizes with the base sequence under highly stringent conditions and encoding a protein having substantially equivalent activity with protein comprising amino acid sequence represented by SEQ ID NO: 18 (hereinafter, sometimes abbreviated as "Sst9-8"); DNA comprising base sequence represented by SEQ ID NO: 19 or DNA encoding protein having a base sequence which hybridizes with the base sequence under highly stringent conditions and substantially equivalent activity with protein comprising having amino acid sequence represented by SEQ ID NO: 20 (hereinafter, sometimes abbreviated as "Sst21-3") or DNA comprising base sequence represented by SEQ ID NO: 21 or DNA having a base sequence which hybridizes with the base sequence under highly stringent conditions and encoding a protein having substantially equivalent activity with protein comprising amino acid sequence represented by SEQ ID NO: 22 (hereinafter, sometimes abbreviated as "Sst20-6").

DNA which can hybridize with the base sequence represented by each of the above-mentioned SEQ ID NOs (SEQ ID NO: 1, 3, 5, 7, 9, 11, 13, 15, 17, 19 or 21) under highly stringent conditions includes DNA comprising base sequence having a homology of about 50% or more, preferably about 60% or more, further preferably about 70% or more, especially preferably about 80% or more, and most preferably about 90% or more with the base sequence, etc.

In the present specification, a homology of the base sequence can be calculated under the following conditions (expected value=10; gap allowed; filtering=ON; match score=1; mismatch score=−3) using a homology calculation algorithm NCBI BLAST (National Center for Biotechnology Information Basic Local Alignment Search Tool). Other algorithms to determine base sequence homology is preferably exemplified by the above-mentioned homology calculation algorithms for the amino acid sequence.

The hybridization can be performed by known methods or by modifications of these methods, for example, according to the method described in Molecular Cloning, 2nd (J. Sambrook et al., Cold Spring Harbor Lab. Press, 1989). If a commercially available library is used, hybridization can be performed according to the instructions of the attached manufacturer's protocol. Preferably, the hybridization can be performed under highly stringent conditions.

The highly stringent conditions used herein are, for example, those in a sodium concentration at about 19 mM to about 40 mM, preferably about 19 mM to about 20 mM at a temperature of about 50° C. to about 70° C., preferably about 60° C. to about 65° C. In particular, the hybridization condition in a sodium concentration of about 19 mM at a temperature of about 65° C. is preferred. Those skilled in this field can easily obtain desired stringency by suitably changing a salt concentration of the hybridization solution, a temperature of hybridization reaction, a probe concentration, a probe length, a mismatch number, a hybridization reaction time, a salt concentration of the washing solution, a washing temperature, etc.

DNA encoding the protein of the present invention is preferably DNA having the base sequence represented by SEQ ID NO: 1 and encoding mouse SST20-14 (Long form) protein, DNA having the base sequence represented by SEQ ID NO: 3 and encoding mouse SST20-14 (Short form) protein, DNA having the base sequence represented by SEQ ID NO: 5 and encoding mouse SST22-22 (Long form) protein, DNA having the base sequence represented by SEQ ID NO: 7 and encoding mouse SST22-22 (Short form) protein, DNA having the base sequence represented by SEQ ID NO: 9 and encoding mouse SST8-5 protein, DNA having the base sequence represented by SEQ ID NO: 11 and encoding mouse SST19-15 (Long form) protein, DNA having the base sequence represented by SEQ ID NO: 13 and encoding mouse SST19-15 (Short form) protein, DNA having the base sequence represented by SEQ ID NO: 15 and encoding mouse SST13-11 protein, DNA having the base sequence represented by SEQ ID NO: 17 and encoding mouse SST9-8 protein, DNA having the base sequence represented by SEQ ID NO: 19 and encoding mouse SST21-3 protein, or DNA having the base sequence represented by SEQ ID NO: 21 and encoding mouse SST20-6 protein, etc.

*Escherichia coli* strains having each of the above-mentioned DNA as a plasmid [in order (1) *Escherichia coli* Top10/pCR4-TOPO (SST20-14 long form), (2) *Escherichia coli* Top10/pCR4-TOPO (SST20-14 short form), (3) *Escherichia coli* Top10/pCR4-TOPO (SST22-22 long form), (4) *Escherichia coli* Top10/pCR4-TOPO (SST22-22 short form), (5) *Escherichia coli* Top10/pCR4-TOPO (SST8-5), (6) *Escherichia coli* Top10/pCR4-TOPO (SST19-15 long form), (7) *Escherichia coli* Top10/pCR4-TOPO (SST19-15 short form), (8) *Escherichia coli* Top10/pCR4-TOPO (SST13-11), (9) *Escherichia coli* Top10/pENTR/D-TOPO (SST9-8), (10) *Escherichia coli* Top10/pCR4-TOPO (SST21-3) and (11) *Escherichia coli* Top10/pCR4-TOPO (SST20-6)] have been deposited with International Patent Organism Depositary, National Institute of Advanced Industrial Science and Technology at Central 6, 1-1-1, Higashi, Tsukuba, Ibaraki, Japan (zip code: 305-8566) under the accession number of FERM BP-8406, FERM BP-8407, FERM BP-8408, FERM BP-8409, FERM BP-8402, FERM BP-8404, FERM BP-8405, FERM BP-8403, FERM BP-8411, FERM BP-8413 and FERM BP-8412, respectively, on Jun. 20, 2003 for (1) to (8), and on Jun. 24, 2003 for (9) to (11).

As an easy method to clone the nucleic acids encoding a secretory or membrane protein such as the protein of the present invention, a signal sequence trap (SST) method is known. This method basically comprises constructing a cDNA library derived from the objective tissue, and using a fusion protein expression vector in which the cDNA library is incorporated into the 5' side of the DNA encoding protein which enables selection of cells only in the case of secretion or transferring to a cell membrane, and using this vector to select cDNA encoding a secretory or membrane protein by an index of the secretion of the protein or the transfer of the protein to the cell membrane. The method includes, for example, a method comprising introducing yeast expression plasmids in which an objective cDNA library is fused to the 5' side of the variant invertase gene in which signal sequence is deleted, into a yeast having a variant invertase which cannot assimilate sucrose, and selecting a yeast having growing property on a medium containing sucrose as a carbon source (Klein et al., Proc. Natl. Acad. Sci. USA, 93: 7108-7113, 1996), a method comprising introducing an expression vector for mammals in which an objective cDNA library is fused to 5' side of the signal deficient variant CD25 antigen gene, into suitable mammal cells, and selecting clones having cDNA encoding a secretory or membrane protein by immunostaining using an antiCD25 antibody (Tashiro et al., Science, 261: 600-603, 1993), a method comprising introducing into a Ba/F3 cell an expression vector for mammals in which an objective cDNA library is fused to the 5' side of the variant thrombopoietin receptor (N-terminal extracellular domain code region is deleted) which allows the Ba/F3 cell strain to grow independently from IL-3, and selecting cells having growing property under absence of IL-3 (Kojima and Kitamura, Nature Biotech., 17: 487-490, 1999; Tsuruga et al., Biochem. and Biophys. Res. Commun., 272: 293-297, 2000), etc.

Genome DNA (where the introduced cDNA is incorporated into the genome) or plasmid DNA or virus DNA (where the introduced cDNA is not incorporated into the genome) is extracted from the selected cell, sense and antisense primers are constructed on the basis of the 5' flanking sequence of the used vector and the 5' side sequence of the fused marker protein gene, the PCR method is performed using the above-mentioned DNA as a template, and cDNA encoding a part of the secretory or membrane protein is isolated and subcloned in a suitable cloning vector.

The base sequence of thus obtained cDNA can be sequenced using a known method (a Maxam-Gilbert method, a dideoxy termination method, etc.).

Cloning means for the nucleic acid encoding the protein of the present invention includes a method comprising performing 5'- and 3'-RACE (Rapid Amplification of cDNA Ends) reaction with mRNA derived from the objective tissue as a template by using two kinds of synthetic DNA primers having the partial base sequence of the identified and sequenced cDNA as described above and a suitable adaptor primer, ligating each obtained amplification fragment with restriction enzyme and ligase, etc. to give full length cDNA, or a method comprising screening again by hybridization from the library using DNA comprising partial or whole region of sequenced cDNA as described above as a probe, to give full length cDNA, etc., but not limited thereto. When RACE method is used, the adaptor primer is preferably a primer in which oligo dT is added to the 3' end of any adaptor sequence (e.g., a sequence comprising a restriction enzyme recognition site for subcloning). In the 5'-RACE, where the endogenous terminal transferase activity of a reverse transcription enzyme is used, an adaptor primer in which dG is added to the 3' end is preferably used since several dC's are usually added. In the case of hybridization, the hybridization can be performed by a known method or an analogue thereof, for example, according to the method described in Molecular Cloning, 2nd ed. (J. Sambrook et al., Cold Spring Harbor Lab. Press, 1989). If a commercially available library is used, hybridization can be performed according to the instructions of the attached manufacturer's protocol.

The base sequence of thus obtained full length cDNA can be sequenced in the same manner as in the partial sequence using a known method (Maxam-Gilbert method, dideoxy termination method, etc.).

DNA (mSst20-14 (Long form)) having the base sequence represented by SEQ ID NO: 1 and encoding the full length of mouse SST20-14 (Long form) protein, and DNA (mSst20-14 (Short form)) having the base sequence represented by SEQ ID NO: 3 and encoding the full length of mouse SST20-14 (Short form) protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 23) of nucleic acids (mSst20-14 (partial)) cloned to *Escherichia coli* Top10/pENTR/D-TOPO (20-14) strain.

DNA (mSst22-22 (Long form)) having the base sequence represented by SEQ ID NO: 5 and encoding the full length of mouse SST22-22 (Long form) protein, and DNA (mSst22-22 (Short form)) having the base sequence represented by SEQ ID NO: 7 and encoding the full length of mouse SST22-22 (Short form) protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 24) of nucleic acids (mSst22-22 (partial)) cloned to *Escherichia coli* Top10/pENTR/D-TOPO (22-22) strain.

DNA (mSst8-5) having the base sequence represented by SEQ ID NO: 9 and encoding the full length of mouse SST8-5 protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 25) of nucleic acids (mSst8-5 (partial)) cloned to *Escherichia coli* Top10/pENTR/D-TOPO (8-5) strain.

DNA (mSst19-15 (Long form)) having the base sequence represented by SEQ ID NO: 11 and encoding the full length of mouse SST19-15 (Long form) protein, and DNA (mSst19-15 (Short form)) having the base sequence represented by SEQ ID NO: 13 and encoding the full length of mouse SST19-15 (Short form) protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 26) of nucleic acids (mSst19-15 (partial)) cloned to *Escherichia coli* Top10/pENTR/D-TOPO (19-15) strain.

DNA (mSst13-11) having the base sequence represented by SEQ ID NO: 15 and encoding the full length of mouse SST13-11 protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 27) of nucleic acids (mSst13-11 (partial)) cloned to *Escherichia coli* Top10/pENTR/D-TOPO (13-11) strain.

DNA (mSst9-8) having the base sequence represented by SEQ ID NO: 17 and encoding the full length of mouse SST9-8 protein, are obtained, for example, by using the above-mentioned SST method from a cDNA library derived from white fat tissue of mouse loaded by high fat foods, and can be obtained by a 5'- and 3'-RACE reaction using an adaptor primer and a primer designed on the basis of the base sequence (SEQ ID NO: 28) of nucleic acids (mSst9-8 (partial)) cloned to *Escherichia coli* Top10/pENTR/D-TOPO (9-8) strain.

DNA (mSst21-3) having the base sequence represented by SEQ ID NO: 19 and encoding the full length of mouse SST21-3 protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 29) of nucleic acids (mSst21-3 (partial)) cloned to *Escherichia coli* Top10/pENTR/D-TOPO (21-3) strain.

DNA (mSst20-6) having the base sequence represented by SEQ ID NO: 21 and encoding the full length of mouse SST20-6 protein, are obtained, for example, by using the above-mentioned SST method from the cDNA library derived from white fat tissue of the mouse loaded by high fat foods, and can be obtained by a 5'- and 3'-RACE reaction using an adaptor primer and a primer designed on the basis of the base sequence (SEQ ID NO: 30) of nucleic acids (mSst20-6 (partial)) cloned to *Escherichia coli* Top10/pENTR/D-TOPO (20-6) strain.

The above-mentioned *Escherichia coli* Top10/pENTR/D-TOPO (20-14) strain, *Escherichia coli* Top10/pENTR/D-TOPO (22-22) strain, *Escherichia coli* Top10/pENTR/D-TOPO (8-5) strain, *Escherichia coli* Top10/pENTR/D-TOPO (19-15) strain, *Escherichia coli* Top10/pENTR/D-TOPO (13-11) strain, *Escherichia coli* Top10/pENTR/D-TOPO (9-8) strain, *Escherichia coli* Top10/pENTR/D-TOPO (21-3) strain and *Escherichia coli* Top10/pENTR/D-TOPO (20-6) strain have been deposited with International Patent Organism Depositary, National Institute of Advanced Industrial Science and Technology at Central 6, 1-1-1, Higashi, Tsukuba, Ibaraki, Japan (zip code: 305-8566) under the accession number of FERM BP-8104, FERM BP-8109, FERM BP-8110, FERM BP-8108, FERM BP-8107, FERM BP-8105, FERM BP-8102 and FERM BP-8106, respectively, on Jul. 14, 2002.

DNA encoding the partial peptide of the present invention is not particularly limited as long as it comprises base sequence encoding a peptide having an amino acid sequence which is the same or substantially the same as a part of the amino acid sequence represented by each of the above-mentioned SEQ ID NOs (SEQ ID NO: 2, 4, 6, 8, 10, 12, 14, 16, 18, 20 or 22). Specifically, DNA encoding the partial peptide of the present invention includes, for example, DNA having (1) a partial base sequence of the base sequence represented by each of the above-mentioned SEQ ID NOs or (2) a base sequence which hybridizes with the DNA having the base sequence represented by each of the above-mentioned SEQ ID NOs under highly stringent conditions, and encoding a peptide having substantially equivalent activity (e.g.: receptor (or ligand) binding activity, signal transduction action, etc.) to that of the protein of the above-mentioned present invention, and the like. Examples of the highly stringent conditions include similar conditions to those mentioned above.

The DNA which can hybridize with the DNA having the base sequence represented by each of the above-mentioned SEQ ID NOs under highly stringent conditions, includes, for example, DNA comprising a base sequence having a homology of about 60% or more, preferably about 70% or more, further preferably about 80% or more and most preferably about 90% or more with the base sequence, etc.

Conversion of the base sequence of DNA to be cloned encoding the protein or its partial peptide of the present invention can be effected by per se known methods such as an ODA-LA PCR method, a Gapped duplex method and a Kunkel method or an analogue thereof using a known kit such as Mutan™-super Express Km (manufactured by Takara Shuzo Co., Ltd.) and Mutan™-K (manufactured by Takara Shuzo Co., Ltd.).

The cloned DNA can be used as it is, depending upon purpose or if desired, after digestion with a restriction enzyme or after addition of a linker thereto. The DNA may have ATG as a translation initiation codon at the 5' end thereof and may further have TAA, TGA or TAG as a translation termination codon at the 3' end thereof. These translation initiation and termination codons may also be added by using a suitable synthetic DNA adapter.

The protein (peptide) of the present invention can be prepared by transforming a host with expression vector comprising the DNA encoding the above-mentioned protein or its partial peptide of the present invention, and cultivating the obtained transformant.

The expression vector comprising the DNA encoding the protein or its partial peptide of the present invention can be manufactured, for example, by excising the desired DNA fragment from the DNA encoding the protein of the present invention, and then ligating the DNA fragment to a suitable expression vector downstream from a promoter in the vector.

Examples of the expression vector include plasmids derived from *E. coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); insect cell expression plasmids (e.g.: pFast-Bac); animal cell expression plasmids (e.g.: pA1-11, pXT1, pRc/CMV, pRc/RSV, pcDNAI/Neo); bacteriophages such as a λ phage; insect virus vectors such as baculovirus (e.g.: BmNPV, AcNPV); animal virus vectors such as retrovirus, vaccinia virus and adenovirus, or the like.

The promoter may be any promoter if it matches well with a host to be used for gene expression.

When animal cells are used as the host, examples of the promoter include an SR α promoter, SV40 promoter, an LTR promoter, a CMV (cytomegalovirus) promoter, an RSV (Rous Sarcoma virus) promoter, MoMuLV (Moloney mouse leukemia virus) LTR, an HSV-TK (simple herpes virus thymidine kinase) promoter, etc., and preferably a CMV promoter, an SRα promoter, etc.

When the host is bacteria of the genus *Escherichia*, preferred examples of the promoter include a trp promoter, a lac promoter, a recA promoter, a $\lambda P_L$ promoter, an lpp promoter, a T7 promoter etc.

When bacteria of the genus *Bacillus* are used as the host, preferred example of the promoter are an SPO1 promoter, an SPO2 promoter, a penP promoter, etc.

When yeast is used as the host, preferred examples of the promoter are a PHO5 promoter, a PGK promoter, a GAP promoter, an ADH promoter, etc.

When insect cells are used as the host, preferred examples of the promoter include polyhedrin prompter, P10 promoter, etc.

The expression vector may further optionally contain an enhancer, a splicing signal, a poly A-addition signal, a selection marker, an SV40 replication origin (hereinafter, sometimes abbreviated as SV40 ori), etc. in addition to the foregoing examples. Examples of the selection marker include a dihydrofolate reductase gene (hereinafter, sometimes abbreviated as dhfr), methotrexate (MTX) resistance), an ampicillin resistant gene (hereinafter, sometimes abbreviated as $amp^r$), a neomycin resistant gene (hereinafter, sometimes abbreviated as $neo^r$, G418 resistance), etc. In particular, when dhfr gene is used as the selection marker together with dhfr gene-deficient Chinese hamster cells, the objective genes can also be selected on a thymidine free medium.

If necessary, a base sequence encoding signal sequence (signal codon) that matches with a host may be added (or substituted with a native signal codon) to the 5' end of the DNA encoding the protein or its partial peptide of the present invention. Examples of the signal sequence that can be used are a PhoA signal sequence, an OmpA signal sequence, etc. in the case of using bacteria of the genus *Escherichia* as the host; an α-amylase signal sequence, a subtilisin signal sequence, etc. in the case of using bacteria of the genus *Bacillus* as the host; an MF α signal sequence, an SUC2 signal sequence, etc. in the case of using yeast as the host; and insulin signal sequence, α-interferon signal sequence, antibody molecule signal sequence, etc. in the case of using animal cells as the host, respectively.

As the host, there can be used, for example, bacteria belonging to the genus *Escherichia*, bacteria belonging to the genus *Bacillus*, yeast, insect cells, insects and animal cells, etc.

As the bacteria belonging to the genus *Escherichia*, there can be used, for example, *Escherichia coli* K12 DH1 [Proceedings of the National Academy of Sciences of the USA (Proc. Natl. Acad. Sci. U.S.A.), Vol. 60, 160 (1968)], *Escherichia coli* JM103 (Nucleic Acids Research, Vol. 9, 309 (1981)), *Escherichia coli* JA221 (Journal of Molecular Biology, Vol. 120, 517 (1978)), *Escherichia coli* HB101 (Journal of Molecular Biology, Vol. 41, 459 (1969)), *Escherichia coli* C600 (Genetics, Vol. 39, 440 (1954)), etc.

As the bacteria belonging to the genus *Bacillus*, there can be used, for example, *Bacillus subtilis* MI114 (Gene, Vol. 24, 255 (1983)), *Bacillus subtilis* 207-21 (Journal of Biochemistry, Vol. 95, 87 (1984)), etc.

As the yeast, there can be used, for example, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71, etc.

As the insect cells, there can be used, for example, for the virus AcNPV, established cell line derived from cabbage armyworm (*Spodoptera frugiperda* cells; Sf cells), MG1 cells derived from mid-intestine of *Trichoplusia* ni, High Five™ cells derived from egg of *Trichoplusia* ni, cells derived from *Mamestra brassicae*, cells derived from Estigmena acrea, etc.; and for the virus BmNPV, established cell line derived from *Bombyx mori* (*Bombyx mori* N cells; BmN cells), etc. As the Sf cells, there can be used, for example, Sf9 cells (ATCC CRL1711) and Sf21 cells (both cells are described in Vaughn, J. L. et al., In Vivo, 13, 213-217 (1977), etc.

As the insect, there can be used, for example, a larva of *Bombyx mori* can be used (Maeda, et al., Nature, Vol. 315, 592 (1985)).

As the animal cells, there can be used, for example, monkey COS-7 cells, monkey Vero cells, Chinese hamster cells CHO (hereinafter, referred to as CHO cells), dhfr gene-deficient Chinese hamster cells CHO (hereinafter, abbreviated as CHO(dhfr⁻) cell), mouse L cells, mouse AtT-20, mouse myeloma cells, rat GH3 cells, human FL cells, etc.

Transformation can be performed according to a known method depending on the kinds of the host.

Bacteria belonging to the genus *Escherichia* can be transformed, for example, by the method described in Proceedings of the National Academy of Sciences of the USA (Proc. Natl. Acad. Sci. U.S.A.), Vol. 69, 2110 (1972) or Gene, Vol. 17, 107 (1982).

Bacteria belonging to the genus *Bacillus* can be transformed, for example, by the method described in Molecular & General Genetics, Vol. 168, 111 (1979).

Yeast can be transformed, for example, by the method described in Methods in Enzymology, Vol. 194, 182-187 (1991), Proc. Natl. Acad. Sci. U.S.A., Vol. 75, 1929 (1978), etc.

The insect cells or the insects can be transformed, for example, according to the method described in Bio/Technology, Vol. 6, 47-55 (1988), etc.

The animal cells can be transformed, for example, according to the method described in Saibo Kogaku (Cell Engineering), Extra issue 8, Shin Saibo Kogaku Jikken Protocol (New Cell Engineering Experimental Protocol), 263-267 (1995), published by Shujunsha, or Virology, Vol. 52, 456 (1973).

Cultivation of a transformant can be performed according to a known method depending on the kinds of the host.

For example, when the host is bacteria belonging to the genus *Escherichia* or the genus *Bacillus*, the transformant can be suitably cultivated in a liquid medium. Preferably the medium contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials include calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

The medium for cultivation of a transformant when the host is the bacteria belonging to the genus *Escherichia*, is preferably, for example, M9 medium supplemented with glucose and Casamino acids (Miller, Journal of Experiments in Molecular Genetics, 431-433, Cold Spring Harbor Laboratory, New York, 1972). If necessary, chemicals such as 3β-indolylacrylic acid can be added to the medium thereby to function the promoter efficiently.

When the bacteria belonging to the genus *Escherichia* are used as the host, the transformant is usually cultivated at about 15° C. to about 43° C. for about 3 hours to about 24 hours. If necessary, the culture may be aerated or agitated.

When the bacteria belonging to the genus *Bacillus* are used as the host, the transformant is cultivated generally at about 30° C. to about 40° C. for about 6 hours to about 24 hours. If necessary, the culture can be aerated or agitated.

When yeast is used as the host, the transformant is cultivated, for example, in Burkholder's minimal medium [Bostian, K. L. et al., Proceedings of the National Academy of Sciences of the USA (Proc. Natl. Acad. Sci. U.S.A.), Vol. 77, 4505 (1980)] or in SD medium supplemented with 0.5% Casamino acids [Bitter, G. A. et al., Proceedings of the National Academy of Sciences of the USA (Proc. Natl. Acad. Sci. U.S.A.), Vol. 81, 5330 (1984)). Preferably, pH of the medium is adjusted to about 5 to about 8. The transformant is usually cultivated at about 20° C. to about 35° C. for about 24 hours to about 72 hours. If necessary, the culture can be aerated or agitated.

When insect cells or insects are used as the host, the transformant is cultivated in, for example, Grace's Insect Medium (Grace, T. C. C., Nature, vol. 195, 788 (1962)) to which a suitable additive such as 10% inactivated bovine serum is added. Preferably, pH of the medium is adjusted to about 6.2 to about 6.4. The transformant is usually cultivated at about 27° C. to about 50° C. for about 3 days to about 5 days and, if necessary and desired, the culture can be aerated or agitated.

When animal cells are employed as the host, the transformant is cultivated in, for example, MEM medium containing about 5% to about 20% fetal bovine serum (Science, vol. 122, 501 (1952)), Dulbecco's Modified Eagle's Medium (DMEM medium; Virology, vol. 8, 396 (1959)), RPMI 1640 medium (The Journal of the American Medical Association, vol. 199, 519 (1967)), 199 medium (Proceeding of the Society for the Biological Medicine, vol. 73, 1 (1950)), etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the protein (peptide) of the present invention may be prepared in the cell or out of the cell of the transformant.

The protein (peptide) of the present invention can be separated and purified from the culture described above which is obtained by cultivating the transformant by known method.

For example, when the protein (peptide) of the present invention is extracted from the culture cells or cytoplasm of the cells, a method can be used in which the cell bodies or cells collected by a known method from the culture are suspended in a suitable buffer and then disrupted by ultrasonication, lysozyme and/or freeze-thaw, followed by centrifugation, filtration, etc. to obtain the crude extract of the soluble protein. The buffer used for the procedures may contain a protein denaturing agent such as urea or guanidine hydrochloride, or a surfactant such as Triton X-100™, etc. On the other hand, when the protein (peptide) of the present invention is extracted from membrane fractions, a method can be used in which cell bodies or cells are disrupted as described above, cell debris is precipitated and removed by low-speed centrifugation, and the supernatant is centrifuged at high speed to precipitate fractions containing the cell membrane (if necessary, cell membrane fractions are purified by density gradient centrifugation, etc.). When the protein (peptide) of the present invention is secreted into the extracellular region, the culture supernatant can be separated from the cultures by centrifugation, filtration or the like to collect the supernatant.

The protein (peptide) of the present invention contained in soluble fractions, membrane fractions or culture supernatant thus obtained can be isolated and purified according to per se known methods. Such methods include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis, etc. These methods may be suitably used in combination.

When the protein (peptide) thus obtained is in a free form, it can be converted into the salt by a per se known method or an analogue thereof. On the other hand, when the protein or peptide is obtained in the form of a salt, it can be converted into the free form or in the form of other salts by a per se known method or an analogue thereof.

The protein (peptide) of the present invention produced by the transformant can be treated, prior to or after the purification, with a suitable protein-modifying enzyme so that the protein can be optionally modified and a polypeptide can be removed partially. Examples of the protein-modifying enzyme include trypsin, chymotrypsin, arginyl endopeptidase, protein kinase, glycosidase or the like.

The existence of the thus produced protein (peptide) of the present invention can be identified by an enzyme immunoassay, Western blotting or the like, using a specific antibody.

Further, the protein (peptide) of the present invention can be synthesized in vitro using a cell-free protein translation system comprising rabbit reticulocyte lysate, wheat germ lysate, *Escherichia coli* lysate, etc. with RNA corresponding to DNA encoding the above-mentioned protein or its partial peptide of the present invention as template. Also, the protein (peptide) of the present invention can be synthesized using cell-free transcription/translation system comprising RNA polymerase, with DNA encoding the protein or its partial peptide of the present invention as template.

The nucleic acids having "the base sequence encoding the protein of the present invention (i.e., the protein comprising an amino acid sequence which is the same or substantially the same as the amino acid sequence represented by SEQ ID NO 2, 4, 6, 8, 10, 12, 14, 16, 18, 20 or 22) or a part thereof", or "the base sequence which is complementary to the base sequence or a part thereof" are meant to include not only above-described nucleic acids encoding the protein or its partial peptide of the present invention, but also a base sequence having mismatch frame.

The nucleic acid comprising a base sequence complementary to a subject region of the objective nucleic acid, i.e., the nucleic acid capable of hybridizing with the objective nucleic acid can be said to be "antisense" against the objective nucleic acid. On the other hand, the nucleic acid comprising a base sequence having homology to a subject region of the objective nucleic acid can be said to be "sense" against the objective nucleic acid. As used herein, "having homology" or "(being) complementary" means having homology or complementarity of about 70% or more, preferably about 80% or more, more preferably about 90% or more, most preferably about 95% or more between the base sequences.

Nucleic acid comprising a base sequence which is complementary to the base sequence encoding the protein of the present invention or a part thereof (hereinafter, also referred to as the "antisense nucleic acid of the present invention") can be designed and synthesized on the basis of base sequence information of cloned or sequenced nucleic acid encoding the protein of the present invention. Such nucleic acid can inhibit replication or expression of the gene encoding the protein of the present invention. That is, the antisense nucleic acid of the present invention can hybridize to RNA transcribed from the genes encoding the protein of the present invention and inhibit mRNA synthesis (processing) or function (translation into protein).

The length of the subject region of the antisense nucleic acid of the present invention is not particularly limited as long as the antisense nucleic acid inhibits translation of the protein of the present invention as results of hybridization of the antisense nucleic acid, and may be whole sequence or partial sequence of mRNA encoding the protein, for example, about 15 bases or so in the case of a short one and full-length in the case of a long one, of mRNA or initial transcription product. Considering ease of synthesis and antigenicity, an oligonucleotide comprising about 15 to about 30 bases is preferred but not limited thereto. Specifically, for example, the 5' end hairpin loop; 5' end 6-base-pair repeats, 5' end untranslated region, polypeptide translation initiation codon, protein coding region, ORF translation initiation codon, 3' end untranslated region, 3' end palindrome region, and 3' end hairpin loop of nucleic acid encoding the protein of the present invention, may be selected as subject regions, though any other region may be selected as a target in the genes encoding the protein of the present invention. For example, the subject region is also preferably intron part of the gene.

Further, the antisense nucleic acid of the present invention may inhibit RNA transcription by forming triple strand (triplex) by binding to the genes encoding the protein of the present invention which is double stranded DNA as well as inhibits translation into protein by hybridizing with mRNA or initial transcription product encoding the protein of the present invention.

Examples of the antisense nucleic acid include deoxypolynucleotides containing 2-deoxy-D-ribose, ribonucleotides containing D-ribose, any other type of nucleotides which are N-glycosides of a purine or pyrimidine base, or other polymers containing non-nucleotide backbones (e.g., commercially available nucleic acid polymers specific for protein nucleic acids and synthetic sequence) or other polymers containing particular linkages (provided that the polymers contain nucleotides having such an alignment that allows base pairing or base bonding, as found in DNA or RNA), etc. It may be double-stranded DNA; single-stranded DNA, double-stranded RNA, single-stranded RNA or a DNA:RNA hybrid, and may further include unmodified polynucleotides (or unmodified oligonucleotides), those with known modifications, for example, those with labels known in the art, those with caps, those which are methylated, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g.; α anomeric nucleic acids, etc.), etc. As used herein, the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides or modified nucleotides also include modifications on the sugar moiety, wherein, for example, one or more hydroxyl groups may optionally be substituted with a halogen atom(s), an aliphatic group(s), etc., or may be converted into the functional groups such as ethers, amines, or the like.

The antisense nucleic acid is RNA, DNA or a modified nucleic acid (RNA and DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be designed preferably based on the following plan, that is by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid. Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acids may contain sugars, bases or bonds, which are changed or modified. The antisense nucleic acids may also be provided in a specialized form such as liposomes, microspheres, or may be applied to gene therapy, or may be provided in combination with attached moieties. Such attached moieties include polycations such as polylysine that act as charge neutralizers of the phosphate group backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other groups may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol, etc.

Ribozymes which can cleave specifically mRNA or initial transcription product encoding the protein of the present invention inside the code region (comprising intron moiety in the case of initial transcription product) can be also included in the antisense nucleic acid of the present invention. The "ribozyme" means RNA having enzyme activity cleaving nucleic acid. However, it has been shown recently that oligo DNA having base sequence of the enzyme activity site also has nucleic acid cleavage activity similarly. Thus, in the present specification, ribozyme is meant to include DNA as long as it has sequence-specific nucleic acid cleavage activity. As most highly used ribozyme, there is self-splicing RNA found in infectious RNA such as viroid and virusoid. Hammerhead type and hairpin type, etc. are known. The hammerhead type exhibits enzyme activity at about 40 bases or so, and can specifically cleave only target mRNA by rendering several bases (about 10 bases or so in total) at the both ends which are adjacent to hammerhead structure moiety, to a sequence complementary to mRNA of the desired cleavage site. This type of ribozyme takes RNA only as a substrate, and thus has an advantage of not attacking genome DNA. When SS169 mRNA has double strand structure by itself, the target sequence can be made to be single stranded by using hybrid ribozyme ligated to RNA motif derived from virus nucleic acid which can bind specifically to RNA helicase [Proc. Natl. Acad. Sci. USA, 98(10): 5572-5577 (2001)]. Further, when ribozyme is used in the form of an expression vector comprising DNA encoding the same, it can be also made to be a hybrid ribozyme further ligated to the sequence obtained by modifying tRNA to promote transfer of the transcription product to cytoplasm [Nucleic Acids Res., 29(13): 2780-2788 (2001)].

Double stranded oligo RNA (siRNA) which is complementary to a partial sequence (comprising intron part in the case of initial transcription product) in the code region of mRNA or initial transcription product encoding the protein of the present invention can be also included in the antisense nucleic acid of the present invention. It has been known that so-called RNA interference (RNAi), which is a phenomenon that if short double stranded RNA is introduced into cells, mRNA complementary to its RNA is degraded, occur in the nematodes, insect, plant, etc. Recently, it has been found that this phenomenon also occurs in mammal cells [Nature, 411 (6836): 494-498 (2001)], which is drawing attention as an alternative technique to ribozymes.

The antisense oligonucleotide and ribozyme of the present invention can be prepared by determining a subject region of mRNA or initial transcription product on the basis of sequence information of cDNA or genome DNA encoding the protein of the present invention, and synthesizing its complementary sequence using commercially available DNA/RNA automatic synthesizer (Applied Biosystems, Beckman, etc.). siRNA having RNAi activity can be prepared by synthesizing sense strand and antisense strand with a DNA/RNA automatic synthesizer, respectively, denaturing them in a suitable annealing buffer, for example, at about 90 to about 95° C. for about 1 minute or so, and annealing them at about 30 to about 70° C. for about 1 to about 8 hours. It can be also prepared as longer double stranded polynucleotide by synthesizing complementary oligonucleotide chains to overlap alternately, annealing them, and ligating them with ligase.

The inhibitory activity of gene expression of the antisense nucleic acid of the present invention can be examined using a transformant comprising nucleic acid encoding the protein of the present invention, a gene expression system for gene encoding the protein of the present invention in vivo and in vitro, or a translation system of the protein of the present invention in vivo and in vitro. The nucleic acid can be applied to cells by a variety of known methods.

The present invention also provides an antibody for the protein (peptide) of the present invention. The antibodies may be any of polyclonal antibodies and monoclonal antibodies as long as they have specific affinity to the protein (peptide) of the present invention. The antibodies for the protein (peptide) of the present invention may be manufactured by known methods for manufacturing antibodies or antisera, using the protein (peptide) of the present invention as antigens.

[Preparation of Monoclonal Antibody]

(a) Preparation of Monoclonal Antibody-producing Cells

The protein (peptide) of the present invention is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually performed once in every 2 to 6 weeks and approximately 2 to 10 times in total. Examples of the applicable mammals are monkeys, rabbits, dogs, guinea pigs, mice, rats, sheep and goats, with mice and rats being preferred.

In the preparation of monoclonal antibody-producing cells, from mammals, e.g., mice, immunized with an antigen, one wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting labeled SS169s, which will be described later, with the antiserum followed by assaying the binding activity of the labeling agent bound to the antibody. The fusion may be operated, for example, by the known Koehler and Milstein method [Nature, vol. 256, 495 (1975)]. Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% or so followed by incubating at 20° C. to 40° C., preferably at 30° C. to 37° C. for 1 to 10 minutes, an efficient cell fusion can be performed.

Various methods can be used for screening of a monoclonal antibody-producing hybridoma. Examples of such methods include a method which comprises adding the culture supernatant of a hybridoma to a solid phase (e.g., microplate) adsorbed with the protein, etc. as an antigen directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase; a method which comprises adding the culture supernatant of a hybridoma to a solid phase adsorbed with an anti-immunoglobulin antibody or Protein A, adding the protein labeled with a radioactive substance or an enzyme and detecting the monoclonal antibody bound to the solid phase; etc.

The monoclonal antibody can be selected by known methods or by analogues of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal calf serum, GIT medium (Wako Pure Chemical Industries, Ltd.) containing 1% to 10% fetal calf serum, a serum free medium for culture of a hybridoma (SFM-101, Nissui Seiyaku Co., Ltd.), etc. may be used for the selection and growth medium. The cultivation is performed generally at 20° C. to 40° C., preferably at about 37° C., for 5 days to 3 weeks, preferably 1 to 2 weeks. The cultivation may be performed normally in 5% $CO_2$. The antibody titer of the culture supernatant of hybridomas can be determined as in the assay for the antibody titer in the antisera described above.

(b) Purification of Monoclonal Antibody

Separation and purification of the monoclonal antibody can be performed by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to give the antibody].

[Preparation of Polyclonal Antibody]

The polyclonal antibody of the present invention can be manufactured by known methods or analogues thereof. For example, a complex of an immunizing antigen (an antigen such as protein) and a carrier protein is prepared, and a mammal is immunized with the complex in a manner similar to the method described above for the manufacture of monoclonal antibodies. The product containing the antibody to the protein (peptide) of the present invention is collected from the immunized animal followed by separation and purification of the antibody.

In the complex of an immunogen and a carrier protein used to immunize a mammal, the type of carrier protein and the mixing ratio of the carrier to hapten may be of any type in any ratio, as long as the antibody is efficiently produced to the hapten immunized by crosslinking to the carrier. For example, bovine serum albumin, bovine thyroglobulins, keyhole limpet hemocyanin, etc. is coupled to hapten with the weight ratio of approximately 0.1 to 20, preferably about 1 to about 5, per one hapten.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to a mammal either solely or together with carriers or diluents to the site in which the antibody may be prepared by the administration. In order to potentiate the antibody productivity upon the administration, complete Freund's adjuvant or incomplete Freund's adjuvant may be administered. The administration is usually made once approximately in approximately every 2 to 6 weeks and about 3 to about 10 times in total.

The polyclonal antibody can be collected from the blood, ascites, etc., preferably from the blood of mammal immunized by the method described above.

The polyclonal antibody titer in antiserum can be assayed by the same procedure as that for the determination of serum antibody titer described above. The separation and purification of the polyclonal antibody can be performed, following the method for the separation and purification of immunoglobulins performed as applied to the separation and purification of monoclonal antibodies described hereinabove.

Expression localization (e.g.: white fat tissue, brown fat tissue, liver, skeletal muscle and the like) of the gene corresponding to cDNA encoding the protein of the present invention which has been cloned and sequenced by the above-mentioned method, and expression change under condition of prescribed stress (e.g.: high fat food loading, fasting, re-feeding following fasting, insulin resistance causing factor stimulation, etc.) can be identified by carrying out Northern blot analysis for RNA derived from various tissues, or RNA derived from the tissue under prescribed conditions of stress and non-stress, using cloned cDNA as itself or a part of the cDNA synthesized on the basis of the determined base sequence as probe, or performing quantitative RT-PCR using synthetic oligonucleotide as primer.

The genes encoding the protein of the present invention are highly expressed in any white fat tissue which has been loaded by high fat food. Among these genes, Sst20-14 gene is specifically expressed in white fat tissue, but Sst19-15, Sst13-11, Sst9-8 and Sst21-3 genes are also expressed in brown fat tissue. Sst21-3 gene is also expressed in undifferentiated precursor adipocyte.

Sst20-14 gene is decreased in expression at the time of fasting, and elevated (recovered) by re-feeding following fasting. Further, the gene is decreased in expression in response to stimulation of insulin resistance causing factor such as TNF-α. Also, by excessive expression of the gene, differentiation of precursor adipocyte into mature adipocyte is suppressed.

Sst8-5 gene is elevated in expression in response to stimulation of an insulin sensitizer.

Sst13-11 gene is decreased in expression at the time of fasting, and elevated (recovered) by re-feeding following fasting. Also, the gene is elevated in expression in response to high fat-high sucrose loading. Further, the genes are highly expressed in the obesity model.

Sst21-3 gene is decreased in expression at the time of fasting, and elevated (recovered) by re-feeding following fasting. Also, the gene is highly expressed in diabetes model.

Sst19-15 gene is also decreased in expression at the time of fasting, and elevated (recovered) by re-feeding following fasting.

As mentioned above, the genes encoding the protein of the present invention is changed in expression in response to stimulation of meal and an insulin resistance regulating agent, or in the conditions of obesity and diabetes, and thus the change of expression affects differentiation of adipocyte.

Therefore, the protein (peptide) of the present invention, nucleic acid (including antisense nucleic acid) encoding the protein (peptide), and an antibody for the protein (peptide) can be used for (1) determination of a compound having specific affinity for the protein of the present invention (the ligand when the protein of the present invention is a membrane protein, and the receptor when the protein of the present invention is a secretory protein), (2) a prophylactic and/or therapeutic agent for diseases associated with dysfunction of the protein of the present invention, (3) a prophylactic and/or therapeutic agent for diseases associated with excessive expression of the protein of the present invention, (4) a gene diagnostic agent, (5) a method of screening a compound changing the expression amount of the protein of the present invention, (6) a prophylactic and/or therapeutic agent for various diseases comprising a compound changing the expression amount of the protein of the present invention, (7) a method of quantifying a compound having specific affinity for the protein of the present invention, (8) a method of screening a compound changing binding property between the protein of the present invention and a compound having specific affinity for the same (agonist and antagonist, etc.), (9) a prophylactic and/or therapeutic agent for various diseases comprising a compound changing binding property between the protein of the present invention and a compound having specific affinity for the same (agonist and antagonist), (10) quantification of the protein (peptide) of the present invention, (11) a method of screening a compound changing the amount of the protein of the present invention on the cell membrane or in the extracellular fluid, (12) a prophylactic and/or therapeutic agent for various diseases comprising a compound changing the amount of the protein of the present invention on the cell membrane or in the extracellular fluid, (13) construction of non-human transgenic animal having DNA encoding the protein (peptide) of the present invention, (14) construction of knockout non-human animal in which the genes encoding the protein of the present invention is inactivated, etc.

Especially, by using affinity assay system with the expression system of the recombinant protein (peptide) of the present invention, a compound changing binding property of the protein of the present invention and its receptor (or ligand) (e.g.: agonist and antagonist, etc.) can be screened, and the agonist or antagonist can be used as a prophylactic and/or therapeutic agent for various diseases, etc.

Uses of the protein (peptide) of the present invention, DNA encoding the protein (peptide) (hereinafter, sometimes abbreviated as the "DNA of the present invention"), the antisense nucleic acid of the present invention and an antibody for the protein (peptide) of the present invention (hereinafter, sometimes abbreviated as the "antibody of the present invention"), will be specifically described below.

(1) Determination of a Compound Having Specific Affinity for the Protein of the Present Invention The proteins (peptides) of the present invention are useful as reagents for screening and determining a compound (receptor or ligand) having specific affinity for the proteins of the present invention or a salt thereof.

That is, the present invention provides a method for determining a compound having specific affinity for the protein of the present invention, which comprises bringing the protein (peptide) of the present invention into contact with a test compound.

When the protein of the present invention is a membrane receptor, examples of the test compound include known ligands (e.g., angiotensin, bombesin, canavinoid, cholecystokinin, glutamine, serotonin, melatonin, neuropeptide Y, opioid, purines, vasopressin, oxytocin, PACAP (pituitary adenylate cyclase-activating polypeptide), secretin, glucagon, calcitonin, adrenomedulin, somatostatin, GHRH (growth hormone releasing hormone), CRF (corticotropin-releasing factor), ACTH (adrenocorticotropic hormone), GRP (gastrin-releasing factor), PTH (parathyroid hormone), VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, $\alpha$- and $\beta$-chemokine (e.g., IL-8, GRO $\alpha$ (growth-related oncogene $\alpha$), GRO $\beta$, GRO $\gamma$, NAP-2 (neutrophil-activating peptide-2), ENA-78 (epithelial neutrophil-activating peptide-78), PF4 (platelet factor 4), IP10 (interferon-producible protein 10), GCP-2 (granulocyte chemotactic protein-2), MCP-1 (monocyte chemotactic protein-1), HC14 (also termed MCP2 (monocyte chemoattractant protein 2)), MCP-3 (monocyte chemoattractant protein-3), I-309 (also termed CCL1 (CC chemokine ligand 1)), MIP1$\alpha$ (macrophage inflammatory protein $\alpha$), MIP-1$\beta$, RANTES (regulated upon activation, normal T-cell expressed and secreted), etc.), endothelin, enterogastrin, histamine, neurotensin, TRH (thyrotropin releasing hormone), pancreatic polypeptide, galanin, etc.) as well as other substances, for example, tissue extracts and cell culture supernatants from mammals (e.g., humans, mice, rats, swine, bovine, sheep, monkeys, etc.). For example, the tissue extract or cell culture supernatant is added to the receptor protein of the present invention and fractionated while assaying cell stimulation activities, etc. to finally give a single ligand. On the other hand, when the protein of the present invention is a secretory protein, for example, tissue extracts derived from human or other mammals, intact cell, cell membrane fractions, cell culture supernatant, etc. may be used as the test compound as described above, in addition to the known receptors for the above-mentioned ligand. For example, the tissue extracts, intact cell, cell membrane fraction, cell culture supernatant, etc. is added to the secretory protein of the present invention, fractionated while assaying cell stimulation activity, etc., finally to give single receptor, etc.

Specifically, a method of determining a compound having specific affinity for the protein or a salt thereof of the present invention, is a method of using the protein (peptide) of the present invention or using an affinity assay system employing the expression system of the protein (peptide) constructed by recombinant techniques, to determine a compound having a cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) (e.g., peptide, protein, non-peptide compound, synthetic compound, fermentation product, etc.) by binding to the receptor protein of the present invention, a compound having a cell stimulation activity by binding to the secretory protein of the present invention, or a salt thereof.

The method of determining a compound having specific affinity for the protein or a salt thereof of the present invention is characterized, for example, by measuring binding amount of the test compound for the protein (peptide) of the present invention and cell stimulation activity, etc. in the case of bringing the protein (peptide) of the present invention into contact with a test compound.

More specifically, the present invention provides:

(1) a method of determining a compound having specific affinity for the protein or a salt thereof of the present invention which is characterized by measuring binding amount of a labeled test compound for the protein (peptide) in the case of bringing labeled test compound into contact with the protein (peptide) of the present invention, (2) a method of determining a compound having specific affinity for the protein or a salt thereof of the present invention which is characterized by measuring binding amount of a labeled test compound for cell, cell membrane fraction, extracellular fluid or cell culture supernatant producing the protein of the present invention in the case of bringing the labeled test compound into contact with the cell or the cell membrane fractions, or the extracellular fluid or the cell culture supernatant (in this case, secretory protein is solidified using, for example, solid phase in which the above-mentioned antibody of the present invention is immobilized (cell cultivation plate, etc.)), (3) a method of determining a compound having specific affinity for the protein or a salt thereof of the present invention which is characterized by measuring binding amount of a labeled test compound for the protein or a salt thereof in the case of bringing labeled test compound into contact with the protein (peptide) of the present invention which is expressed on the cell membrane by cultivating a transformant comprising DNA encoding the protein or its partial peptide of the present invention, or secreted into the culture supernatant (in this case, secretory protein (peptide) is solidified using, for example, solid phase in which the above-mentioned antibody of the present invention is immobilized (cell cultivation plate, etc.)), (4) a method of determining ligand (or receptor) for the membrane protein of the present invention (or secretory protein) or a salt thereof which is characterized by measuring cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) mediated by the membrane protein of the present invention (or a membrane protein which is a test compound, etc.) in the case of bringing a test compound (or cells having a membrane protein which is a test compound, etc. on the cell membrane) into contact with cells producing the membrane protein of the present invention (or culture supernatant of cells producing the secretory protein of the present invention), and (5) a method of determining ligand (or receptor) for the membrane protein of the present invention (or secretory protein) or a salt thereof which is characterized by measuring cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) mediated by the membrane protein of the present invention (or a membrane protein which is a test compound, etc.) in the case of bringing a test compound (or cells having a membrane protein which is a test compound, or the like on the cell membrane) into contact with the membrane protein expressed on the cell membrane by cultivating a transformant comprising DNA encoding the membrane protein of the present invention (or a secretory protein secreted into the culture supernatant by cultivating a transformant comprising DNA encoding the secretory protein of the present invention).

It is particularly preferred to perform the tests (1) to (3) described above thereby confirming that the test compound can bind to the protein (peptide) of the present invention, followed by the test (4) or (5) described above.

As the protein (peptide) of the present invention used in the method of determining ligands (or receptor), any one comprising the protein, its partial peptide or a salt thereof of the present invention may be used, but the recombinant protein of the present invention produced in a large amount by animal cells is appropriate.

The recombinant protein of the present invention can be manufactured by the expression method described above, preferably by expressing DNA encoding the protein of the present invention in mammalian or insect cells. As DNA fragments encoding the desired portion of the protein, cDNA is generally used but not necessarily limited thereto. For example, gene fragments or synthetic DNA may also be used. For introducing a DNA fragment encoding the protein of the present invention into host animal cells (or insect) and efficiently expressing the same, it is preferred to insert the DNA fragment downstream of an SV40-derived promoter, a retrovirus promoter, a metallothionein promoter, a human heat shock promoter, a cytomegalovirus promoter, an SR α promoter, a polyhedrin promoter of nuclear polyhedrosis virus (NPV), which is a baculovirus having insect hosts or the like. The amount and quality of the protein expressed can be determined by a known method. For example, this determination can be made by the method described in the literature [Nambi, P., et al., Journal of Biological Chemistry (J. Biol. Chem.), vol. 267, 19555-19559 (1992)).

In the method of determining ligand (or receptor) of the present invention, the protein (peptide) of the present invention may be the protein (peptide) of the present invention purified according to a known method, or may be in the form of cell producing the protein (peptide) of the present invention or cell membrane fraction thereof, or culture supernatant secreting the protein (peptide) of the present invention.

In the ligand determination method of the present invention where cells containing the protein (peptide) of the present invention are used, the cells may be fixed with glutaraldehyde, formalin, etc. The cells can be fixed by known methods.

The cells containing the protein (peptide) of the present invention are host cells that have expressed the protein (peptide) of the present invention. As the host cells, *Escherichia coli, Bacillus subtilis*, yeast, insect cells, animal cells, etc. are used.

The cell membrane fraction refers to a fraction abundant in cell membrane obtained by a known method after cell disruption. Cell disruption methods include cell squashing using a Potter-Elvehjem homogenizer, disruption using a Waring blender or Polytron (manufactured by Kinematica Inc.), disruption by ultrasonication, and disruption by cell spraying through thin nozzles under an increased pressure using a French press or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), and the resulting supernatant is then centrifuged at a higher speed (15,000 rpm to 30,000 rpm) normally for 30 minutes to 2 hours. The precipitate thus obtained is used as the membrane fraction. The membrane fraction is rich in the protein (peptide) of the present invention expressed and membrane components such as cell-derived phospholipids and membrane proteins.

The amount of the protein (peptide) of the present invention in cells producing the protein (peptide) of the present invention or membrane fraction thereof is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of test samples can be assayed with the same lot.

To perform the methods (1) to (3) supra for determination of a ligand to the protein of the present invention or its salt, an appropriate membrane fraction containing the protein (peptide) of the present invention and a labeled test compound are required.

The membrane fraction containing the protein (peptide) of the present invention is preferably a membrane fraction of naturally occurring protein of the present invention or a membrane fraction of recombinant form of the protein (peptide) of the present invention which has an equivalent activity to that of the naturally occurring protein. As used herein, the "equivalent activity" is intended to mean equivalent ligand binding activity, signal transduction action or the like.

Preferred examples of labeled test compounds include angiotensin, bombesin, canavinoid, cholecystokinin, glutamine, serotonin, melatonin, neuropeptide Y, opioid, purine, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotriene, pancreastatin, prostaglandin, thromboxane, adenosine, adrenaline, α- and β-chemokine (e.g., IL-8, GRO α, GRO β, GRO γ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, etc, each of which is labeled with [$^3$H]), [$^{125}$I], [$^{14}$C], [$^{35}$S], etc.

Specifically, to determine ligands to the protein or a salt thereof of the present invention, first, the standard of the protein (peptide) of the present invention is prepared by suspending cells producing the protein (peptide) of the present invention or cell membrane fraction thereof in a buffer suitable for the determining. For the buffer, any buffer that does not interfere with the binding of the ligand to the protein of the present invention is usable and examples of such a buffer are phosphate buffer, Tris-hydrochloride buffer, etc., having a pH value of 4 to 10 (preferably a pH value of 6 to 8). To minimize a non-specific binding, a surfactant such as CHAPS, Tween-80™ (Kao-Atlas Co.), digitonin, deoxycholate, or various proteins such as bovine serum albumin and gelatin may be added to the buffer. To inhibit degradation of the receptor and the ligand by proteases, protease inhibitors such as PMSF, leupeptin, E-64 (manufactured by Peptide Research Laboratory, Co.), and pepstatin may be added. Test compound labeled with [$^3$H], [$^{125}$I], [$^{14}$C], [$^{35}$S], etc. in a predetermined amount (5,000 to 500,000 cpm) is added to 0.01 to 10 ml suspension of the protein (peptide) of the present invention. To examine non-specific binding (NSB), a reaction tube containing the unlabeled test compound in large excess is also prepared. The reaction is performed at about 0° C. to 50° C., preferably about 4° C. to 37° C. for about 20 minutes to about 24 hours, preferably about 30 minutes to about 3 hours. After completion of the reaction, the reaction mixture is filtrated through glass fiber filter paper, etc. and washed with a suitable volume of the same buffer. The residual radioactivity on the glass fiber filter paper is then counted by means of a liquid scintillation counter or γ-counter. A test compound of which the count (B-NSB) obtained by subtracting the amount of non-specific binding (NSB) from entire binding amount (B) is more than 0 cpm can be selected as a ligand (agonist) for the protein or a salt thereof of the present invention.

To perform the methods (4) and (5) of determining the ligands to the protein and a salt thereof of the present invention as described above, the cell stimulation activity (e.g., activities that enhance or suppress arachidonic acid release, acetylcholine release, intracellular $Ca^{2+}$ release, intracellular cAMP production, intracellular cGMP production, inositol-phosphate production, cell membrane potential changes, phosphorylation of intracellular protein, activation of c-fos, reduction of pH, etc.) mediated by the protein of the present invention may be assayed by known methods, or using assay kits commercially available. Specifically, the cells producing the protein (peptide) of the present invention are firstly cultivated on a multi-well plate, etc. Prior to ligand-determination, the medium is replaced with a fresh medium or with an appropriate non-cytotoxic buffer, and a test compound or the like is added thereto, followed by incubation for a predetermined time. Subsequently, the cells are extracted or the supernatant is recovered and the resulting product is quantified by the respective methods. Where it is difficult to detect the production of an indicator substance (e.g., arachidonic acid, etc.) for the cell stimulation activity due to a degrading enzyme contained in the cells, an inhibitor against the degrading enzyme may be added prior to the assay. For detecting activities such as the cAMP production suppressing activity, the suppressing effect on the cells wherein the baseline production is increased by forskolin or the like can be detected.

Although the method of determining the compound having specific affinity for the protein of the present invention has been described in detail taking the case that the protein of the present invention is a membrane protein, those skilled in this field can perform determination of the compound having specific affinity easily also in the case that the protein of the present invention is a secretory protein by applying the above-mentioned method.

A kit for determining a compound having specific affinity for the protein or a salt thereof of the present invention comprises the protein (peptide) of the present invention, cells producing the protein of the present invention or its membrane fraction, culture supernatant of cells secreting the protein of the present invention, etc.

Examples of the kit for determining the ligands (receptor) of the present invention are as follow.

1. Reagents for Determining Ligand (Receptor)

(1) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a pore size 0.45 μm filter, and stored at 4° C. or may be prepared at use.

(2) Standard of the Protein (Peptide) of the Present Invention

CHO cells wherein the protein (peptide) of the present invention is expressed are subcultured on a 12-well plate at a density of $5 \times 10^5$ cells/well and cultured at 37° C. under 5% $CO_2$ and 95% air for 2 days (when the protein of the present invention is a secretory protein, the plate is coated with antibody for the protein).

(3) Labeled Test Compound

Compound labeled with [$^3$H], [$^{125}$I], [$^{14}$C], [$^{35}$S] and the like which is commercially available, or compound labeled by a suitable method.

A solution of the compound is stored at 4° C. or −20° C. and upon use, diluted to 1 μM with the assay buffer. The test compound which is poorly soluble in water, is dissolved in dimethylformamide, DMSO, methanol, etc.

(4) Non-Labeled Test Compound

The same compound as the labeled compound was prepared, which has a 100- to 1,000-fold concentration.

2. Assay Method (1) The CHO cells expressing the protein (peptide) of the present invention which has been cultured on a 12-well tissue culture plate are washed twice with 1 ml of the assay buffer (when the protein of the present invention is secreted, cells and culture supernatant are removed and then the plate is washed in the same manner with the assay buffer), and 490 μl of the assay buffer is added to each well.

(2) 5 μl of the labeled test compound is added and the reaction is performed at room temperature for an hour. To examine the non-specific binding, 5 μl of the non-labeled test compound is previously added.

(3) The reaction solution is removed and the wells are washed 3 times with 1 ml of the wash buffer. The labeled test compound bound to the cells (plate) is dissolved in 0.2N NaOH-1% SDS, and mixed with 4 ml of liquid scintillator A (manufactured by Wako Pure Chemical Industries, Ltd.).

(4) The radioactivity is measured using a liquid scintillation counter (manufactured by Beckman Co.).

The ligand which can bind to the membrane protein or a salt thereof of the present invention includes, for example, substances which specifically exist in brain, hypothalamus, pancreas, etc., specifically, angiotensin, bombesin, canavinoid, cholecystokinin, glutamine, serotonin, melatonin, neuropeptide Y, opioid, purine, vasopressin, oxytocin, PACAP, secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotriene, pancreastatin, prostaglandin, thromboxane, adenosine, adrenaline, α- and β-chemokine (e.g., IL-8, GRO α, GRO β, GRO γ, NAP-2, ENA-78, PF4, IP10, GCP-2, MCP-1, HC14, MCP-3, I-309, MIP1α, MIP-1β, RANTES, etc.), endothelin, enterogastrin, histamine, neurotensin, TRH, pancreatic polypeptide, galanin, etc. The receptor which can bind to the secretory protein or a salt thereof of the present invention includes receptors for the above-mentioned ligand and various orphan receptor, etc.

(2) A prophylactic and/or Therapeutic Agent for Diseases Associated with Dysfunction of the Protein of the Present Invention In the above-mentioned (1), if a compound having specific affinity for the protein of the present invention is shown, (i) the protein (peptide) of the present invention or (ii) DNA encoding the protein (peptide) can be used as medicines such as a prophylactic and/or therapeutic agent for diseases associated with dysfunction of the protein of the present invention, depending on the action of the compound.

For example, for patients in which the protein of the present invention is reduced in the body so physiological action of the ligands (or receptor) is not expected to be exerted (the protein of the present invention-deficient diseases), actions of ligands (or receptor) can be exerted enough by (1) supplementing the amount of the protein of the present invention by administering the protein (peptide) of the present invention to the patients, or (2) by increasing the amount of the protein of the present invention in the body of the patients through (i) administering DNA encoding the protein (peptide) of the present invention to the patients and expressing it, or (ii) introducing DNA encoding the protein (peptide) of the present invention into the subject cells, expressing it, and then implanting the cells to the patients. That is, the protein (peptide) of the present invention or DNA encoding the same is useful as a prophylactic and/or therapeutic agent for diseases associated with dysfunction of the protein of the present invention, which is safe and less toxic.

The protein of the present invention is highly expressed in white adipocyte at the time of stress by high fat foods loading, and changed in expression depending on stimulation by meal or an insulin resistance regulating agent and conditions such as obesity and/or diabetes, and its expression change affects differentiation of adipocyte. From this fact, examples of diseases associated with dysfunction of the protein of the present invention include diseases involving abnormality (dysfunction or elevation) of adipocyte differentiation and/or metabolism function (especially glucose and/or lipid metabolism) (e.g., obesity, diabetes, impaired glucose tolerance, arteriosclerosis, hypertension, hyperlipidemia, etc.), etc.

(i) The protein (peptide) of the present invention and (ii) DNA encoding the protein (peptide) (in the present specification, referred to sometimes as the "DNA of the present invention"), is mixed with pharmacologically acceptable carriers to prepare pharmaceutical composition, if necessary, and can be used as a prophylactic and/or therapeutic agent for diseases associated with dysfunction of the protein of the present invention.

The pharmacologically acceptable carrier includes various kinds of organic or inorganic carriers which are conventionally used as pharmaceutical materials, such as excipient, lubricant, binder, and disintegrator for solid preparations; or the solvent, solubilizer, suspending agent, isotonizing agent, buffer, and soothing agent for liquid preparations. Further, additives such as antiseptics, antioxidant, colorant, sweetener, etc. can also be incorporated, if necessary.

The excipient preferably includes lactose, sucrose, D-mannitol, D-sorbitol, starch, α-starch, dextrin, crystalline cellulose, low-substituted hydroxypropylcellulose, carboxymethylcellulose sodium, gum arabic, dextrin, pullulan, light silicic anhydride, synthetic aluminum silicate, magnesium metasilicate aluminate, etc.

The lubricant includes magnesium stearate, calcium stearate, talc, colloidal silica, etc.

The binder includes, for example, α-starch, cane sugar, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone, etc.

The disintegrator includes lactose, sucrose, starch, carboxymethylcellulose, carboxymethylcellulose calcium, croscarmellose sodium, carboxymethylstarch sodium, light silicic anhydride, low-substituted hydroxypropylcellulose, etc.

The solvent includes water for injection, physiological saline, Ringer's solution, alcohol, propylene glycol, polyethylene glycol, sesame oil, corn oil, olive oil, cottonseed oil, etc.

The solubilizer includes polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate, etc.

The suspending agent includes surfactants such as stearyltriethanolamine, sodium lauryl sulfate, laurylaminopropionic acid, lecithin, benzalkonium chloride, benzethonium chloride, glyceryl monostearate, etc.; and hydrophilic polymer such as polyvinyl alcohol, polyvinylpyrrolidone, carboxymethylcellulose sodium, methylcellulose, hydroxymethylcellulose, hydroxyethylcellulose, hydroxypropylcellulose, etc.; polysorbates, polyoxyethylene hydrogenated castor oil, etc.

The isotonizing agent includes sodium chloride, glycerin, D-mannitol, D-sorbitol, glucose, etc.

The buffer includes phosphate, acetate, carbonate, citrate, etc.

The soothing agent includes benzyl alcohol, etc.

The antiseptic includes p-oxybenzoic acid esters, chlorobutanol, benzyl alcohol, phenethyl alcohol, dehydroacetic acid, sorbic acid, etc.

The antioxidant includes sulfites, ascorbic acid salts, etc.

The colorant includes, for example, water-soluble food tar colors (e.g., Food Color Red No. 2 and 3, Food Color Yellow No. 4 and No. 5, and Food Color Blue No. 1 and No. 2; and water-insoluble lake colors (e.g., aluminum salt of the above-mentioned water-soluble food tar colors), natural colors (e.g., β-carotene, chlorophyll, Bengala and the like), etc.

The sweetener includes, for example, saccharin sodium, dipotassium glycyrrhizinate, aspartame, stevia, etc.

Formulation of the pharmaceutical composition includes, for example, oral preparations such as tablets, capsules (including soft capsule and microcapsule), granules, powders, syrups, emulsion, suspension, etc., or non-oral preparations such as injections (e.g., subcutaneous injections, intravenous injections, intramuscular injections, peritoneal injections, etc.), external preparations (e.g., nasal preparations, transdermal preparations, ointments, etc.) and suppositories (e.g., rectal suppositories, vaginal suppositories, etc.), pellet, drops, sustained-release preparations (e.g., sustained-release microcapsule, etc.).

These pharmaceutical compositions can be produced according to a conventional method in the technical field of the drug formulation, for example, the method described in the Japanese Pharmacopoeia. Specific methods of preparing the preparations will be described below. Content of active ingredients in the pharmaceutical composition varies depending on formulation, dose of the active ingredients, etc., and is for example about 0.1 to 100% by weight.

The oral preparation can be produced by adding an excipient (e.g., lactose, sucrose, starch, D-mannitol, etc.), a disintegrator (e.g., carboxymethylcellulose calcium, etc.), a binder (e.g., α-starch, gum arabic, carboxymethylcellulose, hydroxypropylcellulose, polyvinylpyrrolidone, etc.), a lubricant (e.g., talc, magnesium stearate, polyethylene glycol 6000, etc.), etc. to active ingredients, followed by compressing it and, coating the formulated product with a coating base for the purpose of taste masking, enteric dissolution or sustained release according to a per se known method, if necessary.

The coating base includes, for example, sugar-coating base, water-soluble film-coating base, enteric film-coating base, sustained-release film-coating base and the like.

The sugar-coating base includes, for example, sucrose, which may be used in combination with one or more of talc, precipitated calcium carbonate, gelatin, gum arabic, pullulan, Carnauba Wax, etc.

The water-soluble film-coating base includes, for example, cellulose polymers such as hydroxypropylcellulose, hydroxypropylmethylcellulose, hydroxyethylcellulose and methylhydroxyethylcellulose; synthetic polymers such as polyvinylacetal diethylaminoacetate, aminoalkylmethacrylate copolymer E [Eudragit E (trademark), Roehm Pharma GmbH], polyvinylpyrrolidone; polysaccharides such as pullulan and the like.

The enteric film-coating base includes, for example, cellulose polymers such as hydroxypropylmethylcellulose phthalate, hydroxypropylmethylcellulose acetatosuccinate, carboxymethylethylcellulose and cellulose acetate phthalate; acrylate polymers such as methacrylate copolymer L [Eudragit L (trademark), Roehm Pharma GmbH], methacrylate copolymer LD [Eudragit L-30D55 (trademark), Roehm Pharma GmbH] and methacrylate copolymer S [Eudragit S (trademark), Roehm Pharma GmbH]; natural substances such as Shellac and the like.

The sustained-release film-coating base includes, for example, cellulose polymers such as ethylcellulose; acrylate polymers such as aminoalkylmethacrylate copolymer RS [Eudragit RS (trademark), Roehm Pharma GmbH], ethyl acrylate/methyl methacrylate copolymer suspension [Eudragit NE (trademark), Roehm Pharma GmbH], etc.

The above-mentioned coating bases may be used in a suitable mixture of two or more. Also, a light-blocking agent such as titanium oxide and iron sesquioxide may be used in coating.

The injections can be produced by dissolving, suspending or emulsifying active ingredients in aqueous solvent (e.g., distilled water, physiological saline, Ringer's solution, etc.) or oily solvent (e.g., vegetable oils such as olive oil, sesame oil, cottonseed oil and corn oil, propylene glycol, etc.) with a dispersing agent (e.g., polysorbate 80, polyoxyethylene hydrogenated castor oil 60, polyethylene glycol, carboxymethylcellulose, and sodium alginate, etc.), a preservative (e.g., methylparaben, propylparaben and benzyl alcohol, chlorobutanol, phenol, etc.), an isotonizing agent (e.g., sodium chloride, glycerin, D-mannitol, D-sorbitol, glucose, etc), etc. If desired, additives such as a solubilizer (e.g., sodium salicylate, sodium acetate, etc.), a stabilizer (e.g., human serum albumin, etc.), soothing agents (e.g., benzyl alcohol, etc.) may be used. The injection is usually filled in suitable ampoules.

The preparations thus obtained are safe and less toxic, can be administered to, for example, mammals (e.g., human, rats, rabbits, sheep, swine, bovine, cats, dogs, monkey, etc.).

When the DNA of the present invention is used as the above-mentioned prophylactic and/or therapeutic agents, the DNA of the present invention can be administered alone; or it is inserted into an appropriate expression vector such as retrovirus vector, adenovirus vector, adenovirus-associated virus vector, etc. and then can be administered according to a conventional method. The DNA of the present invention may also be administered as it is, or with adjuvants to assist its uptake by gene gun or through a catheter such as a catheter with a hydrogel.

The dose of the protein (peptide) of the present invention varies depending on the subject to be administered, the subject organ, symptoms, route for administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, route for administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). In the case that the subject to be administered to is other than human, the corresponding dose as converted per 60 kg body weight can be administered.

The dose of the DNA of the present invention varies depending on the subject to be administered, the subject organ, symptoms, route for administration, etc.; for example, in oral administration, the dose is normally about 0.1 to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, route for administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). In the case that subject to be administered is other than human, the corresponding dose as converted per 60 kg body weight can be administered.

(3) a Prophylactic and/or Therapeutic Agent for Diseases Associated with Excessive Expression of the Protein of the Present Invention An antibody for the protein (peptide) of the present invention can inactivate (that is, neutralize) signal transduction function involved with the protein of the present invention, for example, cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) mediated by the protein of the present invention. On the other hand, antisense nucleic acid of the protein or a partial peptide thereof of the present invention (comprising double stranded oligo RNA having ribozyme and RNAi activity) can inhibit expression of the protein of the present invention by blocking transcription of the gene of the protein of the present invention, processing of the transcription product and/or translation from mRNA. Accordingly, (i) the antibody of the present invention or (ii) the antisense nucleic acid of the present invention can be used as medicines such as a prophylactic and/or therapeutic agent for diseases associated with excessive expression of the protein of the present invention.

The protein of the present invention is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, examples of diseases associated with excessive expression of the protein of the present invention include diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.), etc.

The antibody of the present invention and the antisense nucleic acid of the present invention can be formulated in the same manner as in "the prophylactic and/or therapeutic agent for diseases associated with dysfunction of the protein of the present invention." Also, the antisense nucleic acid can be administered as it is by gene gun or through a catheter such as a catheter with a hydrogel.

The dose of the antibody of the present invention varies depending on the subject to be administered, the subject organ, symptoms, route for administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, route for administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). In the case that subject to be administered is other than human, the corresponding dose as converted per 60 kg body weight can be administered.

The dose of the antisense nucleic acid of the present invention varies depending on the subject to be administered, the subject organ, symptoms, route for administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, route for administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). In the case that subject to be administered is other than human, the corresponding dose as converted per 60 kg body weight can be administered.

(4) A Gene Diagnostic Agent

By using the nucleic acid comprising base sequence encoding the protein of the present invention or a part thereof (hereinafter, referred to as "the sense nucleic acid of the present invention") or the antisense nucleic acid of the present invention as a probe, an abnormality of the DNA or mRNA (gene abnormality) encoding the protein of the present invention in mammal (e.g., human, rats, rabbits, sheep, swine, bovine, cats, dogs, monkey, etc.) can be detected. Therefore, they are useful as a gene diagnostic product for damages to the DNA or mRNA, its mutation or decreased expression, or increased expression or overexpression of the DNA or mRNA.

The gene diagnosis described above using the sense nucleic acid or antisense nucleic acid of the present invention can be performed by, for example, per se known northern hybridization or PCR-SSCP assay (Genomics, vol. 5, pp. 874-879 (1989); Proceedings of the National Academy of Sciences of the United States of America, vol. 86, pp. 2766-2770 (1989)).

For example, when decreased expression of the protein of the present invention is detected by northern hybridization, it can be diagnosed that the subject has been affected with a disease associated with dysfunction of the protein or the subject is highly likely to suffer in the future from the disease. Conversely, when overexpression of the protein of the present invention is detected by northern hybridization, it can be diagnosed that the subject has been affected with a disease associated with enhancement of the function of the protein or the subject is highly likely to suffer in the future from the disease.

The protein of the present invention is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, the sense nucleic acid or antisense nucleic acid of the present invention is useful for diagnosing diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.).

(5) A Method of Screening a Compound Changing the Expression Amount of the Genes Encoding the Protein of the Present Invention The sense or antisense nucleic acid of the present invention can be used in screening a compound changing the expression amount of the genes encoding the protein of the present invention as probe. The compound changing the expression amount of the genes encoding the protein of the present invention can also be screened by carrying out RT-PCR using the sense nucleic acid and antisense nucleic acid of the present invention as a pair of primers.

That is, the present invention provides a method of screening a compound changing the expression amount of the genes encoding the protein of the present invention by measuring the amount of mRNA encoding the protein (peptide) of the present invention contained in, for example, (i) (1) blood, (2) certain organ, (3) tissue or cells isolated from the organ of non-human mammal, or (ii) transformant, etc.

Measurement of the amount of mRNA encoding the protein (peptide) of the present invention is specifically performed as follows.

(i) Medicines (e.g., an antiobesity drug, an antidiabetic drug, an antihypertensive drug, a vasoactive drug, an anticancer agent, etc.) or physical stress (e.g., soaking stress, electric shock, light and dark, low temperature, etc.), etc. are given for normal or disease model non-human mammals (e.g., mice, rats, rabbits, sheep, swine, bovine, cats, dogs, monkey, etc., more specifically, obese mice, diabetic mice, hypertensive rats, arteriosclerotic rabbits, tumor-bearing mice, etc.), and after predetermined time, blood, or certain organ (e.g., brain, liver, kidney, etc.), or tissue (e.g., brown or white fat tissue, etc.) isolated from the organ or cell (adipocyte, etc.) is obtained.

mRNA encoding the protein of the present invention contained in the obtained cells can be quantified by extracting mRNA from the cells, etc. by a conventional method and quantifying it by a method such as TaqMan PCR, and can be analyzed by carrying out Northern blot by per se known means.

(ii) Transformant expressing the protein (peptide) of the present invention is constructed according to the above-described method, and mRNA encoding the protein (peptide) of the present invention contained in the transformant can be quantified and analyzed in the same manner.

Screening a compound changing the expression amount of the genes encoding the protein of the present invention can be performed by, (i) administering the test compound to normal or disease model non-human mammal at predetermined time before (30 minutes to 24 hours before, preferably 30 minutes to 12 hours before, more preferably 1 hour to 6 hours before) or at predetermined time after (30 minutes to 3 days after, preferably 1 hour to 2 days after, more preferably 1 hour to 24 hours after) giving medicines or physical stress, etc., or at the same time as giving medicines or physical stress, and at predetermined time after the administration (30 minutes to 3 days after, preferably 1 hour to 2 days after, more preferably 1 hour to 24 hours after), quantifying and analyzing an amount of mRNA encoding the protein of the present invention contained in the cells, (ii) mixing the test compound into the medium when cultivating transformant according to a conventional method, and at predetermined time after the cultivation (1 day to 7 days after, preferably 1 day to 3 days after, more preferably 2 days to 3 days after), quantifying and analyzing the amount of mRNA encoding the protein (peptide) of the present invention contained in the transformant.

A kit for screening a compound changing the expression amount of the genes encoding the protein of the present invention is characterized by comprising (a) a probe composed of the sense and/or antisense nucleic acid of the present invention, preferably double stranded oligo DNA, or (b) a primer set composed of the sense nucleic acid of the present invention and the antisense nucleic acid of the present invention. The probe is labeled with RI, fluorescence or enzyme, etc. by a conventional method.

The screening kit may further comprise, if desired, reagents and/or tool for extracting RNA (e.g., extraction buffer, spin column, etc.), reagents and/or tool for PCR or Northern hybridization (e.g., dNTPs, PCR reaction buffer, heat-resistant DNA polymerase, etc.), transformant expressing the protein (peptide) of the present invention, etc.

The compound or a salt thereof obtained by using the screening method of the present invention is a compound having action of changing the expression amount of the genes encoding the protein of the present invention, specifically, (i) a compound potentiating cell stimulation activity (e.g., activities that enhance or suppress arachidonic acid release, acetylcholine release, intracellular $Ca^{2+}$ release, intracellular cAMP production, intracellular cGMP production, inositol-phosphate production, cell membrane potential changes, phosphorylation of intracellular protein, activation of c-fos, reduction of pH, etc.) mediated by interaction of the protein of the present invention and its receptor (or ligand), by increasing expression amount of the protein of the present invention, and (ii) a compound attenuating the cell stimulation activity by decreasing expression amount of the protein of the present invention.

The compound includes peptide, protein, non-peptide compound, synthetic compound, fermentation product, etc., and these compounds may be a novel compound or a known compound.

The compound potentiating the cell stimulation activity is useful as safe and less toxic medicines for potentiating physiological activity of the protein of the present invention.

The compound attenuating the cell stimulation activity is useful as safe and less toxic medicines for reducing physiological activity of the protein of the present invention.

When the compound or a salt thereof obtained by using the above-mentioned screening method is used as a medicine, it can be formulated in the same manner as in "the prophylactic and/or therapeutic agent for diseases associated with dysfunction of the protein of the present invention."

The preparation thus obtained is safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, mode of administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). When the subject to be administered is non-human animal, the corresponding dose as converted per 60 kg body weight can be administered.

(6) A Prophylactic and/or Therapeutic Agent for Various Diseases Comprising a Compound Changing the Expression Amount of the Genes Encoding the Protein of the Present Invention The protein of the present invention, as described above, is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, the protein is considered to play an important role in regulating adipocyte differentiation and/or metabolism function. Accordingly, a compound changing the expression amount of the genes encoding the protein of the present invention can be used as a prophylactic and/or therapeutic agent for diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.).

When the compound is used as a prophylactic and/or therapeutic agent for diseases associated with dysfunction or enhancement of the protein of the present invention, it can be formulated in the same manner as in "the prophylactic and/or therapeutic agent for diseases associated with dysfunction of the protein of the present invention."

The preparation thus obtained are safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, mode of administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). When the subject to be administered is non-human animal, the corresponding dose as converted per 60 kg body weight can be administered.

(7) A Method of Quantifying a Compound (Ligand or Receptor) Having Specific Affinity for the Protein of the Present Invention Since the protein (peptide) of the present invention has binding property for a ligand (or receptor) for the protein of the present invention, concentration of the ligand (or receptor) in the living body can be quantified with high sensitivity.

The quantifying method for a ligand (or receptor) of the present invention can be performed in combination with, for example, a competitive method. That is, by bringing test samples into contact with the protein (peptide) of the present invention, concentration of the ligand (or receptor) in the test samples can be measured. Specifically, it can be performed according to for example, a method as described in following 1) or 2), etc. or modifications thereof.

1) Hiroshi Irie, ed., "Radioimmunoassay" (Kodansha Ltd., published in 1974)

2) Hiroshi Irie, ed., "Sequel to the Radioimmunoassay" (Kodansha Ltd., 1979)

(8) A Method of Screening a Compound (Agonist and Antagonist, Etc.) Changing Binding Property Between the Protein of the Present Invention and a Compound (Ligand or Receptor) Having Specific Affinity for the Same A compound changing binding property between the protein of the present invention and its ligands (or receptor) (e.g., peptide, protein, non-peptide compound, synthetic compound, fermentation product, etc.) or a salt thereof, can be screened in high efficiency by using the protein (peptide) of the present invention, or by constructing an expression system of the recombinant protein (peptide) of the present invention and using affinity assay system with the expression system.

Such compound includes (i) a compound having receptor-mediated cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) (so-called agonist for receptor of the membrane protein of the present invention or the secretory protein of the present invention), (ii) a compound not having the cell stimulation activity (so-called antagonist for receptor of the membrane protein of the present invention or the secretory protein of the present invention), (iii) a compound potentiating binding ability between the protein of the present invention and its ligands (or receptor), or (iv) a compound reducing binding ability between the protein of the present invention and its ligands (or receptor) (further, the above-mentioned compound (i) is preferably screened by the ligand determining method as described in above-mentioned (1)).

That is, the present invention provides a method of screening a compound changing binding property between the protein of the present invention and its ligands (or receptor) or a salt thereof which is characterized by comparing (i) the case of bringing the protein (peptide) of the present invention into contact with its ligands (or receptor) and (ii) the case of bringing the protein (peptide) of the present invention into contact with its ligands (or receptor) and a test compound.

In the screening method of the present invention, it is characterized by measuring and comparing binding amount of the protein of the present invention for ligands (or receptor), cell stimulation activity, etc. in the cases of (i) and (ii).

More specifically, the present invention provides:

1) a method of screening a compound changing binding property between the protein of the present invention and its ligands (or receptor) or a salt thereof which is characterized by measuring and comparing binding amount of labeled ligands (or receptor) for the protein (peptide) in the case of bringing labeled ligands (or receptor) into contact with the protein (peptide) of the present invention and in the case of bringing the labeled ligands (or receptor) and a test compound into contact with the protein (peptide) of the present invention, 2) a method of screening a compound changing binding property between the protein of the present invention and its ligands (or receptor) or a salt thereof which is characterized by measuring and comparing binding amount of labeled ligands (or receptor) for cells producing the protein of the present invention or its membrane fraction, or extracellular fluid or cell culture supernatant (in this case, the protein of the present invention is solidified using, for example, solid phase (cell cultivation plate, etc.) in which the above-mentioned antibody of the present invention is immobilized), in the case of bringing labeled ligands (or receptor) into contact with the cells producing the protein of the present invention or its membrane fraction, or the extracellular fluid or the cell culture supernatant, and in the case of bringing the labeled ligands (or receptor) and a test compound into contact with the cells producing the protein of the present invention or its membrane fraction, or the extracellular fluid or the cell culture supernatant, 3) a method of screening a compound changing binding property between the protein of the present invention and its ligands (or receptor) or a salt thereof which is characterized by measuring and comparing binding amount of labeled ligands (or receptor) for the protein (peptide) of the present invention, in the case of bringing labeled ligands (or receptor) into contact with the protein (peptide) of the present invention which is expressed on the cell membrane, or secreted into the culture supernatant (in this case, the protein (peptide) of the present invention is solidified using, for example, solid phase (cell cultivation plate, etc.) in which the above-mentioned antibody of the present invention is immobilized) by cultivating a transformant comprising DNA of the present invention, and in the case of bringing the labeled ligands (or receptor) and a test compound into contact with the protein (peptide) of the present invention which is expressed on the cell membrane, or secreted into the culture supernatant by cultivating a transformant comprising DNA of the present invention, 4) a method of screening a compound changing binding property between the protein of the present invention and its ligands (or receptor) or a salt thereof which is characterized by measuring and comparing receptor-mediated cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.), in the case of bringing a compound activating the protein of the present invention (e.g., ligands for the membrane protein of the present invention, etc.) or a compound activated by the protein of the present invention (e.g., receptor for the secretory protein of the present invention, etc.), into contact with cells expressing the protein of the present invention on the cell membrane or culture supernatant into which the protein of the present invention is secreted, and in the case of bringing the compound activating the protein of the present invention or the compound activated by the protein of the present invention and a test compound, into contact with the cells expressing the protein of the present invention on the cell membrane or the culture supernatant into which the protein of the present invention is secreted, and 5) a method of screening a compound changing binding property between the protein of the present invention and its ligands (or receptor) or a salt thereof which is characterized by measuring and comparing receptor-mediated cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.), in the case of bringing a compound activating the protein of the present invention (e.g., ligand for the membrane protein of the present invention, etc.) or a compound activated by the protein of the present invention (e.g., receptor for the secretory protein of the present invention, etc.), into contact with the protein (peptide) of the present invention which is expressed on the cell membrane by cultivating a transformant comprising DNA of the present invention, or the protein (peptide) of the present invention which is secreted into the culture supernatant by cultivating a transformant comprising DNA of the present invention, and in the case of bringing the compound activating the protein of the present invention or the compound activated by the protein of the present invention and a test compound, into contact with the protein (peptide) of the present invention which is expressed on the cell membrane by cultivating a transformant comprising DNA of the present invention, or the protein (peptide) of the present invention which is secreted into the culture supernatant by cultivating a transformant comprising DNA of the present invention.

The screening method of the present invention will be specifically described below.

First, the protein (peptide) of the present invention used for the screening methods of the present invention may be any of those comprising the protein of the present invention or a partial peptide or a salt thereof, preferred is cell membrane fraction of organ or extracellular fluid of mammals producing the protein of the present invention. However, since human-derived organs in particular are obtained only with extreme difficulty, the human-derived protein (peptide) of the present invention produced in a large amount by recombinant host is appropriate for use in screening.

The proteins (peptides) of the present invention can be manufactured by the method described above, preferably by expressing DNA of the present invention in mammalian or insect cells. As DNA fragments encoding the desired portion of the protein, cDNA is generally used but not necessarily limited thereto. For example, gene fragments or synthetic DNA may also be used. For introducing a DNA fragment encoding the protein of the present invention or partial peptide thereof into host animal (insect) cells and efficiently expressing the same, it is preferred to insert the DNA fragment downstream of an SV40-derived promoter, a retrovirus promoter, a metallothionein promoter, a human heat shock promoter, a cytomegalovirus promoter, an SRα promoter, a polyhedrin promoter of nuclear polyhedrosis virus (NPV) which belongs to a baculovirus having insect hosts or the like. The amount and quality of the protein expressed can be determined by a per se known method. For example, this determination can be made by the method described in the literature (Nambi, P., et al., J. Biol. Chem., vol. 267, 19555-19559 (1992)).

Therefore, the proteins (peptides) of the present invention which are used in the screening method of the present invention may be those purified according to a per se known method, or may be in the form of cells producing the protein (peptide) of the present invention or its cell membrane fraction, or culture supernatant of cells secreting the protein (peptide) of the present invention.

When cells producing the protein (peptide) of the present invention are used in the above-mentioned screening method, the cells may be fixed with glutaraldehyde, formalin, etc. The fixation method can be carried out by per se known methods.

The cells producing the protein (peptide) of the present invention are host cells that have expressed the protein (peptide) of the present invention. As the host cells, *Escherichia coli*, *Bacillus subtilis*, yeast, insect cells, animal cells, etc. are used.

The cell membrane fraction refers to a fraction abundant in cell membrane obtained by a per se known method after cell disruption. Cell disruption methods include cell-squashing method using a Potter-Elvehjem homogenizer, disruption using a Waring blender or Polytron (manufactured by Kinematica Inc.), disruption by ultrasonication, and disruption by cell spraying through thin nozzles under an increased pressure using a French press, etc. For cell membrane fractionation, fractionation by a centrifugal force, such as fractional centrifugation method and density gradient centrifugation method is mainly used. For example, cell disruption fluid is centrifuged at a low speed (500 rpm to 3,000 rpm) for a short period of time (normally about 1 to about 10 minutes), and the supernatant is then centrifuged at a higher speed (15,000 rpm to 30,000 rpm) normally for 30 minutes to 2 hours. The precipitate thus obtained is used as the membrane fraction. The membrane fraction is rich in the protein (peptide) of the present invention expressed and membrane components such as cell-derived phospholipids and membrane proteins.

The amount of the protein (peptide) of the present invention in cells producing the protein (peptide) of the present invention or its membrane fraction is preferably $10^3$ to $10^8$ molecules per cell, more preferably $10^5$ to $10^7$ molecules per cell. As the expression amount increases, the ligand binding activity per unit of membrane fraction (specific activity) increases so that not only the highly sensitive screening system can be constructed but also large quantities of samples can be assayed with the same lot.

To perform the methods 1) through 3) supra for screening a compound changing binding property between the protein of the present invention and its ligand, an appropriate fraction containing protein (peptide) of the present invention and a labeled ligand are required.

The fraction containing protein of the present invention is preferably a fraction containing a naturally occurring protein of the present invention, a fraction containing a recombinant protein of the present invention having equivalent activities to those of the naturally occurring protein, or the like. As used herein, the term "equivalent activity" is intended to mean an equivalent ligand binding activity, signal transduction action or the like.

As the labeled ligand, labeled ligand, labeled ligand analogue compound, etc. are used. For example ligand labeled with $[^3H]$, $[^{125}I]$, $[^{14}C]$, $[^{35}S]$, etc. are used.

Specifically, to screen a compound changing binding property between the protein of the present invention and its ligand, first, the standard of the protein (peptide) of the present invention is prepared by suspending cells producing the protein (peptide) of the present invention or its cell membrane fraction in a buffer suitable for the screening. For the buffer, any buffer that does not interfere with the binding of the ligand to the protein of the present invention is usable and examples of such a buffer are phosphate buffer, Tris-hydrochloride buffer, etc., having a pH value of 4 to 10 (preferably a pH value of 6 to 8). To minimize a non-specific binding, a surfactant such as CHAPS, Tween-80™ (Kao-Atlas Co.), digitonin, deoxycholate, etc. may be added to the buffer. To inhibit degradation of the receptor and the ligand by proteases, protease inhibitors such as PMSF, leupeptin, E-64 (manufactured by Peptide Research Laboratory, Co.), and pepstatin may be added. The labeled ligand in a predetermined amount (5,000 to 500,000 cpm) is added to 0.01 to 10 ml solution of the receptor at the same time under coexistence of $10^{-4}$ M to $10^{-10}$ M of test compound. To examine non-specific binding (NSB), a reaction tube containing the unlabeled ligand in large excess is also prepared. The reaction is performed at approximately 0 to 50° C., preferably about 4° C. to 37° C. for about 20 minutes to about 24 hours, preferably about 30 minutes to about 3 hours. After completion of the reaction, the reaction mixture is filtrated through glass fiber filter paper, etc. and washed with a suitable volume of the same buffer. The residual radioactivity on the glass fiber filter paper is then measured by means of a liquid scintillation counter or γ-counter. If a test compound of which specific binding amount (B-NSB) is 50% or less when setting the count ($B_0$-NSB) obtained by subtracting the amount of non-specific binding (NSB) from count ($B_0$) in the absence of antagonistic substance to 100%, it can be selected as candidate substance having antagonistic ability.

To perform a method of screening a compound changing binding property between the protein of the present invention and its ligand according to the above-mentioned 4) or 5), the cell stimulation activity mediated by the protein of the present invention (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) can be measured by a known method, or using an assay kit commercially available.

Specifically, the cells producing the protein (peptide) of the present invention are firstly cultivated on a multi-well plate, etc. Prior to screening, the medium is replaced with a fresh medium or with an appropriate non-cytotoxic buffer, and a test compound or the like is added thereto, followed by incubation for a given period of time. Subsequently, the cells are extracted or the supernatant is recovered and the resulting product is quantified by the respective methods. Where it is difficult to detect the production of an indicator substance for the cell stimulation activity (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To carry out screening by measuring cell stimulation activity, suitable cells expressing the protein (peptide) of the present invention on the membrane are required. The cells expressing the protein (peptide) of the present invention are preferably cell lines producing the naturally occurring membrane protein of the present invention, cell lines expressing above-described recombinant protein (peptide) of the present invention, etc.

The test compound includes, for example, peptide, protein, non-peptide compound, synthetic compound, fermentation product, cell extracts, plant extracts, animal tissue extracts, etc., and these compounds may be a novel compound or a known compound.

Although the method of screening a compound changing binding property between the protein of the present invention and its ligands (or receptor) or a salt thereof, has been described in the above in detail taking the case that the protein of the present invention is a membrane protein, those skilled in this field can perform screening a compound changing binding property of the secretory protein of the present invention and its receptor even in the case that the protein of the present invention is a secretory protein by applying the above-mentioned method.

A kit for screening a compound changing binding property between the protein of the present invention and a compound having specific affinity for the same (ligand or receptor) or a salt thereof comprises the protein (peptide) of the present invention, cells producing the protein (peptide) of the present invention or its membrane fraction, or culture supernatant of cells secreting the protein (peptide) of the present invention, etc.

Examples of the kit for screening of the present invention are as follows.

1. Reagents for Screening (i) Assay Buffer and Wash Buffer

Hanks' balanced salt solution (manufactured by Gibco Co.) supplemented with 0.05% bovine serum albumin (manufactured by Sigma Co.).

The solution is sterilized by filtration through a 0.45 μm filter, and stored at 4° C. or may be prepared at use.

(ii) Standard of the Protein (Peptide) of the Present Invention

CHO cells expressing the protein (peptide) of the present invention are subcultured on a 12-well plate at a density of $5 \times 10^5$ cells/well and cultured at 37° C. under 5% $CO_2$ and 95% air for 2 days (when the protein (peptide) of the present invention is secreted, the plate is coated with antibody for the protein).

(iii) Labeled Ligand (Receptor)

Ligand (receptor) labeled with [$^3$H], [$^{125}$I], [$^{14}$C], [$^{35}$S], etc. which is commercially available A solution thereof is stored at 4° C. or −20° C. and upon use, diluted to 1 μM with the assay buffer.

(iv) Ligand (Receptor) Standard Solution

The ligand (receptor) is dissolved in PBS containing 0.1% bovine serum albumin (manufactured by Sigma Co.) at the concentration of 1 mM, and the solution is stored at −20° C.

As labeled receptor and receptor standard solution, proteoliposome in which receptor protein is embedded into liposome membrane composed of suitable lipid composition is suspended in suitable dispersing solvent (water, PBS, etc.), and stored at 4° C.

2. Assay Method (i) The CHO cells expressing the protein (peptide) of the present invention, which has been cultured on a 12-well tissue culture plate, was washed twice with 1 ml of the assay buffer (when the protein (peptide) of the present invention is secreted, cell and culture supernatant is removed and then the plate is washed in the same manner with the assay buffer), 490 μl of the assay buffer is added to each well.

(ii) 5 μl of $10^{-3}$ to $10^{-10}$ M test compound solution is added, and then 5 μl of labeled ligands (or receptor) is added and the reaction is performed at room temperature for an hour. To examine the non-specific binding, 5 μl of $10^{-3}$ M ligand (or receptor) standard solution is previously added instead of the test compound.

(iii) The reaction solution is removed and the wells are washed 3 times with 1 ml of the wash buffer. The labeled ligands (or receptor) bound to the cells (or plate) is dissolved in 0.2N NaOH-1% SDS, and mixed with 4 ml of liquid scintillator A (manufactured by Wako Pure Chemical Industries, Ltd.).

(iv) The radioactivity is measured using a liquid scintillation counter (manufactured by Beckman Co.), and the percent maximum binding (PMB) is calculated in accordance with the following equation [Equation 1].

$$PMB = [(B-NSB)/(B_0-NSB)] \times 100 \quad \text{[Equation 1]}$$

PMB: Percent maximum binding
B: Value obtained in the presence of a test compound
NSB: Non-specific binding
$B_0$: Maximum binding The compound or a salt thereof obtained by using the above-mentioned screening method or the kit for screening is a compound having action of changing binding property between the protein of the present invention and a compound having specific affinity for the same (ligand or receptor), specifically, (i) a compound having ligand-receptor interaction-mediated cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) (so-called agonist for the membrane protein of the present invention or receptor of the secretory protein of the present invention), (ii) a compound not having the cell stimulation activity (so-called antagonist for the membrane protein of the present invention or receptor of the secretory protein of the present invention), (iii) a compound potentiating binding ability between the protein of the present invention and its ligands (or receptor), or (iv) a compound reducing binding ability between the protein of the present invention and its ligands (or receptor).

The compound includes peptide, protein, non-peptide compound, synthetic compound, fermentation product, etc., and these compounds may be a novel compound or a known compound.

The agonist for the membrane protein of the present invention (or receptor of the secretory protein of the present invention) is useful as safe and less toxic medicines depending on the ligand activity since it has similar biological activities to those of ligands for the membrane protein of the present invention (or to those of the secretory protein of the present invention for receptor).

The antagonist for the membrane protein of the present invention (or receptor of the secretory protein of the present invention) is useful as safe and less toxic medicines for suppressing the ligand activity since it can suppress biological activities of ligands for the membrane protein of the present invention (or the secretory protein of the present invention for receptor).

The compound potentiating binding ability between the membrane protein of the present invention and its ligands (or the secretory protein of the present invention and its receptor) is useful as safe and less toxic medicines for potentiating physiological activity of ligands for the membrane protein of the present invention (or the secretory protein of the present invention for receptor).

The compound reducing binding ability between the membrane protein of the present invention and its ligands (or the secretory protein of the present invention and its receptor) is useful as safe and less toxic medicines for reducing physiological activity of ligands for the membrane protein of the present invention (or the secretory protein of the present invention for receptor).

When the compound or a salt thereof obtained by using the above-mentioned screening method or the kit for screening is used as a medicine, it can be formulated in the same manner as in "the prophylactic and/or therapeutic agent for diseases associated with dysfunction of the protein of the present invention."

The preparations thus obtained are safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal lipid metabolism (as 60 kg body weight). In parenteral administration, a single dose varies depending on the subject to be administered, the subject organ, symptoms, mode of administration, etc.; for example, in injection administration, the dose is normally about 0.01 to 30 mg, preferably about 0.1 to 20 mg, and more preferably about 0.1 to 10 mg per day for a patient having abnormal lipid metabolism (as 60 kg body weight). When the subject to be administered is non-human animal, the corresponding dose as converted per 60 kg body weight can be administered.

(9) A Prophylactic and/or Therapeutic Agent for Various Diseases Comprising a Compound (Agonist and Antagonist) Changing Binding Property Between the Protein of the Present Invention and a Compound (Ligand or Receptor) Having Specific Affinity for the Same The protein of the present invention, as described above, is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, the protein is considered to play an important role in regulating adipocyte differentiation and/or metabolism function. Accordingly, a compound changing binding property between the protein of the present invention and its ligands (or receptor) (agonist and antagonist) can be used as a prophylactic and/or therapeutic agent for diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.).

When the compound is used as a prophylactic and/or therapeutic agent for diseases associated with dysfunction or enhancement of the protein of the present invention, it can be formulated in the same manner as in "the prophylactic and/or therapeutic agent for diseases associated with dysfunction of the protein of the present invention."

The preparations thus obtained are safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, mode of administration, etc.; for example, in injection administration, the dose of about 0.01 to about 30 mg, preferably about 0.1 to about 20 mg, and more preferably about 0.1 to about 10 mg per day is administered intravenously to a patient having abnormal glucose and/or lipid metabolism (as 60 kg body weight). When the subject to be administered is non-human animal, the corresponding dose as converted per 60 kg body weight can be administered.

(10) Quantification of the Protein (Peptide) of the Present Invention

The antibody of the present invention can specifically recognize the protein (peptide) of the present invention. Therefore, the antibody can be used to quantify the protein (peptide) of the present invention in a test fluid, especially for quantification by the sandwich immunoassay, etc. That is, the present invention provides, for example, the following methods of quantification:

(i) A method of quantifying the protein (peptide) of the present invention in a test fluid, which comprises competitively reacting the antibody of the present invention with the test fluid and a labeled form of the protein (peptide) of the present invention, and measuring the ratio of the labeled protein (peptide) of the present invention bound to the antibody; and, (ii) A method of quantifying the protein (peptide) of the present invention in a test fluid, which comprises reacting the test fluid with the antibody of the present invention immobilized on a carrier and a labeled form of the antibody of the present invention simultaneously or sequentially, and measuring the activity of the labeling agent on the immobilized carrier.

In the quantifying method (ii), the antibodies preferably have antigen recognition sites in which insolubilized antibody and labeled antibody do not inhibit binding of the protein (peptide) of the present invention each other (e.g., one antibody recognizes the N-terminus of the protein (peptide) of the present invention, and another antibody reacts with the C-terminus of the protein (peptide) of the present invention).

Using a monoclonal antibody against the protein (peptide) of the present invention (hereinafter, referred to sometimes as the monoclonal antibody of the present invention), the protein (peptide) of the present invention can be measured, and the protein (peptide) of the present invention can further be detected by tissue staining. For these purposes, the antibody molecule itself may be used, or F(ab')2, Fab' or Fab fractions of the antibody molecule may be used as well. The methods for measuring the protein (peptide) of the present invention using the antibody of the present invention are not to be limited particularly. Any method can be used, so long as the amount of antibody, antigen, or antibody-antigen complex corresponding to the amount of antigen (e.g., the amount of the protein of the present invention) in a test fluid can be detected by chemical or physical means and can be calculated from a standard curve prepared from standard solutions containing known amounts of the antigen. For example, nephrometry, competitive method, immunometric method, and sandwich method are advantageously used, among which the sandwich method described below is particularly preferable in terms of sensitivity and specificity.

As labeling agents used for the assay methods using labeled substances, there are employed, for example, radioisotopes, enzymes, fluorescent substances, luminescent substances, etc. As the radioisotopes, there are employed, for example, [$^{125}$I], [$^{131}$I], [$^{3}$H], [$^{14}$C], etc. As the enzymes described above, stable enzymes with a high specific activity are preferred; for example, β-galactosidase, β-glucosidase, alkaline phosphatase, peroxidase, malate dehydrogenase, etc. are used. Examples of the fluorescent substance used are fluorescamine, fluorescein isothiocyanate, etc. As the luminescent substances, there are employed, for example, luminol, luminol derivatives, luciferin, lucigenin, etc. Furthermore, the biotin-avidin system may also be used for binding of an antibody or antigen to the labeling agent.

For immobilization of the antigen or antibody, physical adsorption may be used. Chemical binding methods conventionally used for insolubilization or immobilization of proteins, enzymes, etc. may be used as well. For the carriers, examples include insoluble polysaccharides such as agarose, dextran, cellulose, etc.; synthetic resin such as polystyrene, polyacrylamide, silicone, etc., or glass, etc.

In the sandwich method, the insolubilized monoclonal antibody of the present invention is reacted with a test fluid (primary reaction), then with a labeled form of monoclonal antibody of the present invention (secondary reaction), and the activity of the labeling agent on the immobilizing carrier is assayed, whereby the amount of the protein of the present invention in the test fluid can be quantified. The order of the primary and secondary reactions may be reversed, and the reactions may be performed simultaneously or with some time intervals. The labeling agent and the methods for insolubilization can be performed by modifications of those methods described above.

In the immunoassay by the sandwich method, the antibody used for immobilized antibody or labeled antibody is not necessarily from one species, but a mixture of two or more species of antibodies may be used to increase the measurement sensitivity.

In the methods of assaying the protein (peptide) of the present invention by the sandwich method, antibodies that bind to different sites of the protein (peptide) of the present invention are preferably used as the monoclonal antibodies of the present invention for the primary and secondary reactions. That is, in the antibodies used for the primary and secondary reactions, for example, when the antibody used in the secondary reaction recognizes the C-terminus region of the protein (peptide) of the invention, it is preferable to use the antibody capable of recognizing the region other than the C-terminus region (e.g., the antibody capable of recognizing the N-terminus region) for the primary reaction.

The monoclonal antibody of the present invention can be used for the assay systems other than the sandwich method, for example, the competitive method, immunometric method, nephrometry, etc. In the competitive method, an antigen in a test fluid and a labeled antigen are competitively reacted with an antibody, and the unreacted labeled antigen (F) and the labeled antigen bound to the antibody (B) are separated (B/F separation). The amount of the labeled antigen in B or F is measured, and the amount of the antigen in the test fluid is quantified. This reaction method includes a liquid phase method using a soluble antibody as an antibody, polyethylene glycol and a secondary antibody to the soluble antibody for B/F separation, etc. and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the solid phase is separated from the liquid phase, or an antigen in a test fluid is reacted with an excess amount of labeled antibody, the immobilized antigen is then added to bind the unreacted labeled antibody to the solid phase, and the solid phase is separated from the liquid phase. Then, the amount of the labeled antibody in either phase is measured to quantify an amount of the antigen in the test fluid.

In the nephrometry, an amount of insoluble precipitates produced after the antigen-antibody reaction in gel or solution are measured. Even when the amount of an antigen in a test fluid is small and only a small amount of precipitates is obtained, laser nephrometry utilizing scattering of laser can be advantageously employed.

For applying these individual immunological assay methods to the quantification methods of the protein (peptide) of the present invention, any particular conditions, and setting of procedures and the like are not required. The assay systems for the protein (peptide) of the present invention may be constructed by adding ordinary technical consideration in the art to conventional conditions and procedures in the respective methods. For the details of these general technical means, reference can be made to the following reviews and texts [see, Hiroshi Irie, ed., "Radioimmunoassay" (Kodansha Ltd., published in 1974), Hiroshi Irie, ed., "Sequel to the Radioimmunoassay" (Kodansha Ltd., published in 1979), Eiji Ishikawa, et al., ed., "Enzyme immonoassay" (Igakushoin, published in 1978), Eiji Ishikawa, et al., ed., "Enzyme immonoassay" (2nd ed.) (Igakushoin, published in 1982), Eiji Ishikawa, et al., ed., "Enzyme immonoassay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing), etc].

As described above, the protein (peptide) of the present invention can be quantified with high sensitivity, by using the antibody of the present invention.

Further, by quantifying the protein of the present invention using the antibody of the present invention, various diseases associated with dysfunction or enhancement of the protein of the present invention can be diagnosed. The protein of the present invention is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, diseases associated with dysfunction or enhancement of the protein of the present invention include diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.), etc.

Besides, the antibody of the present invention can be used for specifically detecting the protein of the present invention, which exists in test samples such as body fluids and tissues. It can also be used for preparation of antibody columns used to purify the protein (peptide) of the present invention, for detection of the protein (peptide) of the present invention in each fraction upon purification, for analysis of the behavior of the protein of the present invention in test cells, etc.

(11) A Method of Screening a Compound Changing the Amount of the Protein of the Present Invention on the Cell Membrane or in the Extracellular Region The antibody of the present invention can specifically recognize the protein (peptide) of the present invention. Therefore, it can be used for screening a compound changing the amount of the protein of the present invention on the cell membrane or in the extracellular region.

That is, the present invention provides:

(i) a method of screening a compound changing the amount of the membrane protein of the present invention on the cell membrane, comprising destroying (1) blood, (2) certain organs, (3) tissue or cells isolated from the organ, etc. of non-human mammals, isolating the cell membrane fraction, and quantifying the protein of the present invention contained in the cell membrane fraction (alternatively, a method of screening a compound changing the amount of the protein of the present invention in the extracellular region, comprising separating extracellular fluids such as plasma, urine and other body fluid of non-human mammals, and quantifying protein of the present invention contained in it), (ii) a method of screening a compound changing the amount of the protein of the present invention on the cell membrane, comprising destroying transformant expressing the protein (peptide) of the present invention, etc., isolating the cell membrane fraction, and quantifying the protein (peptide) of the present invention contained in the cell membrane fraction, (alternatively, a method of screening a compound changing the amount of the protein of the present invention in the extracellular region, comprising separating culture supernatant of transformant expressing the protein (peptide) of the present invention, and quantifying the protein (peptide) of the present invention contained in the culture supernatant), (iii) a method of screening a compound changing the amount of the protein of the present invention on the cell membrane, comprising identifying the protein of the present invention on the cell membrane by preparing slices of (1) blood, (2) certain organ, (3) tissue or cells isolated from the organ, etc. of non-human mammals, and quantifying the staining level of the protein of the present invention in the cell surface layer with immunostaining method, and (iv) a method of screening a compound changing the amount of the protein (peptide) of the present invention on the cell membrane, comprising identifying the protein (peptide) of the present invention on the cell membrane by preparing slices of a transformant expressing the protein of the present invention or a partial peptide thereof, etc., and quantifying staining level of the protein (peptide) of the present invention in the cell surface layer with immunostaining method.

Quantification of the protein (peptide) of the present invention contained in the cell membrane fraction is specifically performed as follows.

(i) Medicines (e.g., an antiobesity drug, an antidiabetic drug, an antihypertensive agent, a vasoactive drug, an anticancer agent, etc.) or physical stress (e.g., water immersion stress, electric shock, light and dark, low temperature, etc.), etc. are given for normal or disease model non-human mammals (e.g., mice, rats, rabbits, sheep, swine, bovine, cats, dogs, monkey, etc., more specifically, obese mice, diabetic mice, hypertensive rats, arteriosclerotic rabbits, tumor-bearing mice, etc.), and after predetermined time, blood, certain organ (e.g., liver, kidney, spleen, muscle, etc.), tissue (e.g., brown or white fat tissue, etc.) or cell (e.g., adipocyte, muscle cell, etc.) is obtained. Obtained cells, etc. are suspended in a suitable buffer (e.g., Tris-HCl buffer, phosphate buffer, HEPES buffer, etc.), etc., the cells, etc. are disrupted using surfactant (e.g., Triton X100™, Tween 20™, etc.), etc., further centrifuged, filtered and column-fractionated, to give cell membrane fraction.

The cell membrane fraction refers to a fraction abundant in cell membrane obtained by cell disruption and per se known methods. The cell disruption methods include cell-squashing method using a Potter-Elvehjem homogenizer, disruption using a Waring blender or Polytron (manufactured by Kinematica Inc.), disruption by ultrasonication, disruption by cell spraying through thin nozzles under an increased pressure using a French press, etc. For cell membrane fractionation, fractionation by a centrifugal force, such as fractional centrifugation method and density gradient centrifugation method is mainly used. For example, cell disruption fluid is centrifuged at a low speed (500 rpm to 3,000 rpm) for a short period of time (normally about 1 to about 10 minutes), the supernatant is then centrifuged at a higher speed (15,000 rpm to 30,000 rpm) normally for 30 minutes to 2 hours. The precipitate thus obtained is used as the membrane fraction. The membrane fraction is rich in the protein (peptide) of the present invention and membrane components such as cell-derived phospholipids and membrane proteins.

The protein (peptide) of the present invention contained in cell membrane fraction can be quantified by, for example, the sandwich immunoassay, western blot analysis, etc. using the antibody of the present invention.

Such sandwich immunoassay can be performed in the same manner as in above-described method, and western blot can be performed by per se known means.

(ii) Transformant expressing the protein (peptide) of the present invention is constructed according to the above-described method, and the protein (peptide) of the present invention contained in cell membrane fraction can be quantified.

Screening a compound changing the amount of the protein of the present invention on the cell membrane can be performed by, (i) administering the test compound to normal or disease model non-human mammal at predetermined time before (30 minutes to 24 hours before, preferably 30 minutes to 12 hours before, more preferably 1 hour to 6 hours before) or at predetermined time after (30 minutes to 3 days after, preferably 1 hour to 2 days after, more preferably 1 hour to 24 hours after) giving medicines or physical stress, etc., or at the same time as giving medicines or physical stress, and at predetermined time after the administration (30 minutes to 3 days after, preferably 1 hour to 2 days after, more preferably 1 hour to 24 hours after), quantifying amount of the protein of the present invention on the cell membrane, or (ii) mixing the test compound into the medium in cultivating transformant according to a conventional method, and at predetermined time after the cultivation (1 day to 7 days after, preferably 1 day to 3 days after, more preferably 2 days to 3 days after), quantifying amount of the protein (peptide) of the present invention on the cell membrane.

Confirmation of the protein (peptide) of the present invention contained in cell membrane fraction is specifically performed as follows.

(iii) Medicines (e.g., an antiobesity drug, an antidiabetic drug, an antihypertensive agent, a vasoactive drug, an anticancer agent, etc.) or physical stress (e.g., water immersion stress, electric shock, light and dark, low temperature, etc.), etc. is given for normal or disease model non-human mammals (e.g., mice, rats, rabbits, sheep, swine, bovine, cats, dogs, monkey, etc., more specifically, obese mice, diabetic mice, hypertensive rats, arteriosclerotic rabbits, tumor-bearing mice, etc.), and after predetermined time, blood, or a certain organ (e.g., liver, kidney, etc.), tissue (e.g., brown or white fat tissue, etc.) or cell (e.g., adipocyte, etc.) is obtained. The obtained cell, etc. is prepared as a tissue slice according to a conventional method, and immunostaining is performed using the antibody of the present invention. By quantifying staining level of the protein of the present invention in the cell surface layer, the protein of the present invention on the cell membrane is identified, and by which, the amount of the protein (peptide) of the present invention on the cell membrane can be determined quantitatively or qualitatively.

(iv) It can be also determined by the same means using a transformant expressing the protein (peptide) of the present invention, etc.

The kit for screening a compound changing the amount of the protein of the present invention on the cell membrane is characterized by comprising the antibody of the present invention as a component. The antibody of the present invention can be subjected in any form which is described in the above-mentioned (10) depending on the immunoassay used. For example, when the sandwich method is used, provided is an antibody of the present invention which is used in the primary reaction in a form that is immobilized (or can be immobilized) on a suitable insoluble carrier (e.g., insoluble polysaccharides such as agarose, dextran and cellulose, synthetic resin such as polystyrene, polyacrylamide, silicone, or glass, etc.), and an antibody of the present invention which is used in the secondary reaction in a form that is labeled (or can be labeled) with a suitable labeling agent [e.g., radioisotopes ($[^{125}I]$, $[^{131}I]$, $[^{3}H]$, $[^{14}C]$, etc.), an enzyme (β-galactosidase, β-glucosidase, alkaline phosphatase, peroxidase, malate dehydrogenase, etc.), a fluorescent substance (fluorescamine, fluorescein isothiocyanate, etc.), a luminescent substance (luminol, luminol derivatives, luciferin, lucigenin, etc.), etc.].

Where necessary, the screening kit may further comprise blocking reagents, washing solution, etc. which is necessary or suitable in an immunological assay, and reagents, transformant expressing the protein (peptide) of the present invention, etc. which is necessary or suitable for isolating of cell membrane fraction.

Although the screening method and the screening kit has been described in the above in detail taking the case that the protein of the present invention is a membrane protein, those skilled in this field can perform screening of a compound changing the amount of the protein of the present invention in the extracellular region even in the case that the protein of the present invention is a secretory protein by applying the above-mentioned method.

The compound or a salt thereof obtained by using the above-mentioned screening method is a compound having action of changing amount of the membrane protein of the present invention on the cell membrane, or amount of the secretory protein of the present invention in the extracellular region, specifically, (i) a compound potentiating cell stimulation activity (e.g., activities that enhance or suppress arachidonic acid release, acetylcholine release, intracellular $Ca^{2+}$ release, intracellular cAMP production, intracellular cGMP production, inositolphosphate production, cell membrane potential changes, phosphorylation of intracellular protein, activation of c-fos, reduction of pH, etc.) mediated by ligand-receptor interaction by increasing amount of the membrane protein of the present invention on the cell membrane, or the secretory protein of the present invention in the extracellular region, and (ii) a compound attenuating the cell stimulation activity by decreasing amount of the membrane protein of the present invention on the cell membrane, or the secretory protein of the present invention in the extracellular region.

The compound includes peptide, protein, non-peptide compound, synthetic compound, fermentation product, etc., and these compounds may be a novel compound or a known compound.

The compound potentiating the cell stimulation activity is useful as safe and less toxic medicines for potentiating physiological activity of the protein of the present invention.

The compound attenuating the cell stimulation activity is useful as safe and less toxic medicines for reducing physiological activity of the protein of the present invention.

When the compound or a salt thereof obtained by using the above-mentioned screening method is used as a medicine, it can be formulated in the same manner as in "the prophylactic and/or therapeutic agent for diseases associated with dysfunction of the protein of the present invention."

The preparations thus obtained are safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, mode of administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). When the subject to be administered is non-human animal, the corresponding dose as converted per 60 kg body weight can be administered.

(12) A Prophylactic and/or Therapeutic Agent for Various Diseases Comprising a Compound Changing the Amount of the Protein of the Present Invention on the Cell Membrane or in the Extracellular Region The protein of the present invention, as described above, is highly expressed in white adipocyte under stress by high fat food loading, and changed in expression depending on stimulation by meal or an insulin resistance regulating agent and conditions such as obesity and/or diabetes, and its expression change affects differentiation of adipocyte. From this fact, the protein is considered to play an important role in regulating adipocyte differentiation and/or metabolism function. Accordingly, a compound changing the amount of the protein of the present invention on the cell membrane or in the extracellular region can be used as a prophylactic and/or therapeutic agent for diseases involving abnormality (dysfunction or enhancement) of adipocyte differentiation and/or metabolism function (especially glucose and/or lipid metabolism) (e.g., obesity, diabetes, impaired glucose tolerance, arteriosclerosis, hypertension, hyperlipidemia, etc.).

When the compound is used as a prophylactic and/or therapeutic agent for diseases associated with dysfunction or enhancement of the protein of the present inventions, it can be formulated in the same manner as in "the prophylactic and/or therapeutic agent for diseases associated with dysfunction of the protein of the present invention."

The preparations thus obtained are safe and less toxic. Therefore, they can be administered to, for example, mammals (e.g., human, rats, rabbits, sheep, swine, bovine, cats, dogs, monkey, etc.).

The dose of the compound or a salt thereof varies depending on the subject to be administered, the subject organ, symptoms, mode of administration, etc.; for example, in oral administration, the dose is normally about 0.1 mg to 100 mg, preferably about 1.0 to 50 mg, and more preferably about 1.0 to 20 mg per day for a patient having abnormal glucose and/or lipid metabolism (as 60 kg body weight). In parenteral administration, a single dose varies depending on the subject to be administered, the subject organ, symptoms, mode of administration, etc.; for example, in injection administration, the dose is normally about 0.01 to 30 mg, preferably about 0.1 to 20 mg, and more preferably about 0.1 to 10 mg per day for a patient having abnormal glucose and/or lipid metabolism (as 60 kg body weight). When the subject to be administered is non-human animal, the corresponding dose as converted per 60 kg body weight can be administered.

(13) Construction of Non-Human Transgenic Animal Bearing DNA Encoding the Protein of the Present Invention The present invention provides a non-human mammal bearing an exogenous DNA encoding the protein of the present invention (hereinafter, abbreviated as the exogenous DNA of the present invention) or its variant DNA (sometimes abbreviated as the exogenous variant DNA of the present invention).

That is, the present invention provides:

1) A non-human mammal bearing the exogenous DNA of the present invention or its variant DNA;

2) The mammal according to 1), which is a rodent;

3) The mammal according to 2), wherein the rodent is mouse or rat; and,

4) A recombinant vector bearing the exogenous DNA of the present invention or its variant DNA and capable of expressing in a mammal.

The non-human mammal bearing the exogenous DNA of the present invention or its variant DNA (hereinafter, abbreviated as the DNA transgenic animal of the present invention) can be prepared by transferring a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by the calcium phosphate method, the electric pulse method, the lipofection method, the aggregation method, the microinjection method, the particle gun method, the DEAE-dextran method or the like. Also, it is possible to transfer the exogenous DNA of the present invention into a somatic cell, a living organ, a tissue cell, or the like by the DNA transfer methods, and utilize them for cell culture, tissue culture, etc. In addition, these cells may be fused with the above-described germinal cell by a per se known cell fusion method to create the DNA transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and, B6C3F$_1$ strain, BDF, strain, B6D2F$_1$ strain, BALB/c strain, ICR strain, etc. for a cross line) or rats (e.g., Wistar, SD, etc.), since they are relatively short in ontogeny and life cycle from a standpoint of creating disease model animals and are easy to breed.

"Mammals" in a recombinant vector that can be expressed in the mammals include the aforementioned non-human mammals and human, etc.

The exogenous DNA of the present invention refers to the DNA of the present invention that is once isolated/extracted from mammals, not the DNA of the present invention inherently possessed by the non-human mammals.

The variant DNA of the present invention includes those resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal protein, etc. of the present invention and exemplified by the DNA that expresses a protein to suppress the functions of the normal protein, etc. of the present invention.

The exogenous DNA of the present invention may be any one of those derived from a mammal of the same species as, or a different species from, the mammal as the target animal. In transferring the DNA of the present invention into the target animal, it is generally advantageous to use the DNA as a DNA construct in which the DNA is ligated downstream from a promoter capable of expressing the DNA in the animal cells. For example, in the case of transferring the human DNA of the present invention, a DNA-introduced mammal that expresses the DNA of the present invention to a high level, can be prepared by microinjecting a DNA construct (e.g., vector, etc.) ligated with the human DNA of the present invention into a fertilized egg of the target mammal, for example mouse, downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for carrying the DNA of the present invention, there are *Escherichia coli*-derived plasmids, *Bacillus subtilis*-derived plasmids, yeast-derived plasmids, bacteriophages such as λ phage, retroviruses such as Moloney leukemia virus, and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include 1) promoters for the DNA derived from viruses (e.g., simian virus, cytomegalovirus, Moloney mouse leukemia virus, JC virus, breast cancer virus, poliovirus, etc.), and 2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscle creatine kinase, glial fibrillary acidic protein, glutathione S-transferase, platelet-derived growth factor β, keratins K1, K10 and K14, collagen types I and II, cyclic AMP-dependent protein kinase β I subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor 1α (EF-1α) promoters, human and chicken β actin promoters etc., which enable high expression systemically in the whole body, are preferred.

It is preferred that the vectors described above have a sequence for terminating the transcription of the desired messenger RNA in the DNA-introduced animal (generally referred to as a terminator); for example, a sequence of each DNA derived from viruses and various mammals. SV40 terminator of the simian virus and the like, are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The normal translational region in the protein of the present invention and the like can be acquired as whole genomic DNA or portion thereof from liver-, kidney-, thyroid cell-, or fibroblast-derived DNA of various mammals (e.g., human, rabbits, dogs, cats, guinea pigs, hamsters, rats, mice, etc.) and commercially available various genomic DNA library, or from a complement DNA as a source, which is prepared by per se known methods from liver-, kidney-, thyroid cell-, or fibroblast-derived RNA. Alternatively, the exogenous abnormal DNA can be prepared by mutating the translational region in the normal protein of the present invention, which is obtained from the above cells or tissues, to variant translational region using point mutagenesis.

The translational region can be prepared as a DNA construct that can be expressed in the transgenic animal by an ordinary DNA engineering method, wherein the DNA is ligated downstream from the abovementioned promoters (and if desired, upstream transcription termination site).

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will carry the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passed as the DNA-bearing animal under ordinary breeding environment, by confirming the fact that the exogenous DNA is stably retained by mating.

By transferring the exogenous DNA of the present invention at the fertilized egg cell stage, the DNA is retained to be excess in all of the germinal and somatic cells of target mammal. The fact that the exogenous DNA of the present invention is excessively present in the germinal cells of the prepared animal after transfer means that the exogenous DNA of the present invention is excessively present in all of the germinal cells and somatic cells of offspring of the prepared animal. The offspring of the animal that inherits the exogenous DNA of the present invention have excessively the exogenous DNA of the present invention in all of the germinal cells and somatic cells thereof.

By obtaining a homozygous animal having the transferred DNA in both of homologous chromosomes and mating a male and female of the animal, all offspring can be passed to retain the DNA in excess.

A non-human mammal having the normal DNA of this invention highly expresses the normal DNA of this invention, and by promoting the function of endogenous normal DNA, the hyperfunction of the protein of this invention may ultimately occur. Thus, it can be used as a pathological model animal. For example, using a transgenic animal of the present invention, to which the normal DNA has been transferred, it is possible to elucidate the pathological mechanism of the hyperfunction of the protein of this invention and the disease involved by the protein of this invention, and to study the therapeutic method of these diseases.

Because a mammal, to which exogenous normal DNA of this invention has been transferred, shows increase in the liberated protein of this invention, it can be used for the screening test of a therapeutic medicine of the diseases related to the protein of this invention.

In the meantime, the non-human mammal, to which the exogenous abnormal DNA of this invention is transferred, can be bred over generations in typical breeding environment as an animal retaining the exogenous DNA, upon confirmation of stable retention of the exogenous DNA by mating.

Moreover, upon incorporation of the objective exogenous DNA in the aforementioned plasmid, it can be used as a starting material. A DNA construct containing a promoter can be prepared according to general DNA engineering technique. The transfer of the abnormal DNA of this invention in the stage of fertilized ovum is ensured to be present in every germinal cell and every somatic cell of the target mammal. The existence of abnormal DNA of this invention in the germinal cell of created animal after DNA transfer means that every germinal cell and every somatic cell in every progeny of the created animal retain the abnormal DNA of the present invention. The offspring of this kind of animal that inherited the exogenous DNA of this invention has the abnormal DNA of this invention in every germinal cell and every somatic cell. By obtaining homozygote animals having the introduced DNA in both the homologous chromosomes and mating male and female of the animals, every offspring can be bred over generations such that the DNA is retained.

A non-human mammal having the abnormal DNA of this invention highly expresses the abnormal DNA of this invention, and inhibition of the function of the endogenous normal DNA sometimes causes ultimately functionally inactive adiaphoria to the protein of this invention. Thus, it can be utilized as a pathological model animal. For example, using an animal, to which the abnormal DNA of this invention has been transferred, elucidation of the pathological mechanism of functionally inactive adiaphoria to the protein of this invention and consideration of the treatment method of these diseases can be afforded.

As a concrete possibility of use, an animal that highly expresses the abnormal DNA of this invention can be a model to clarify the functional inhibition (dominant negative action) of normal protein by abnormal protein of this invention in functionally inactive adiaphoria to the protein of this invention.

Because a mammal, to which the exogenous abnormal DNA of this invention has been transferred, shows condition of increase in the liberated abnormal protein of this invention, it can be utilized for screening test of a therapeutic drug of functionally inactive adiaphoria to the protein of this invention.

As a possibility of other use of the above-mentioned two kinds of the transgenic animals of this invention, for example, 1) use as cell source for tissue cultivation,
2) analysis of relationship with a protein that is specifically expressed or activated due to the protein of this invention, by a direct analysis of DNA or RNA in the tissue of the transgenic animals of this invention or by analysis of protein expressed by the DNA in the tissue,
3) study of cell function from tissue generally difficult to cultivate, by cultivating cells of tissue having a DNA by general tissue cultivation technique and using them,
4) screening of a pharmaceutical agent that enhances the function of cells by the use of the cell described in the above-mentioned 3), and
5) isolation and purification of mutant protein of this invention and production of its antibody, and the like.

Furthermore, clinical condition of the diseases relating to the protein of this invention, including functionally inactive adiaphoria to the protein of this invention can be investigated using the transgenic animal of this invention, and detailed pathological findings in each organ of the disease model relating to the protein of this invention can be obtained, thus contributing to the development of a new therapeutic method, and study and therapy of secondary disease due to said disease.

Establishment of cultivated cells is also possible by removing each organ from the transgenic animal of this invention, followed by dicing, liberating DNA-transferred cells by a protease such as trypsin, and cultivation thereof. Moreover, characterization of a cell producing the protein of this invention, relationship with apoptosis, differentiation or propagation, or signal transduction mechanism thereof can be examined to look for abnormality therein and the like, thus providing effective research material for the elucidation of the protein of this invention and its action.

Furthermore, for the development of a therapeutic medicine of diseases relating to the protein of this invention, including functionally inactive adiaphoria to the protein of this invention, by the use of the transgenic animal of this invention, an effective and rapid screening method of a said therapeutic medicine of the disease can be provided, using the aforementioned test method, quantification method and the like. In addition, using the transgenic animal of this invention or an exogenous DNA expression vector of this invention, a DNA therapy of diseases relating to the protein of this invention can be studied and developed.

(14) Preparation of Knockout Non-Human Animal in which the Gene Encoding the Protein of the Present Invention is Inactivated The present invention further provides a non-human mammal embryonic stem cell where the DNA of this invention is inactivated and non-human mammal deficient in expression of DNA of this invention.

Accordingly, the present invention provides:

1) A non-human mammal embryonic stem cell in which the DNA of the present invention is inactivated;

2) The embryonic stem cell according to 1), wherein the DNA is inactivated by introducing a reporter gene (e.g., β-galactosidase gene derived from *Escherichia coli*);

3) The embryonic stem cell according to 1), which is resistant to neomycin;

4) The embryonic stem cell according to 1), wherein the non-human mammal is a rodent;

5) The embryonic stem cell according to 4), wherein the rodent is mouse;

6) A non-human mammal deficient in expressing the DNA of the present invention, wherein the DNA of the present invention is inactivated;

7) The non-human mammal according to 6), wherein the DNA is inactivated by introducing a reporter gene (e.g., β-galactosidase derived from *Escherichia coli*) therein and the reporter gene is capable of being expressed under control of the promoter to the DNA of the present invention;

8) The non-human mammal according to 6), which is a rodent;

9) The non-human mammal according to 8), wherein the rodent is mouse; and

10) A method for screening a compound or salt thereof that promotes or inhibits the promoter activity for the DNA of the present invention, which comprises administering a test compound to the animal of 7) and detecting expression of the reporter gene.

The non-human mammal embryonic stem cell where the DNA of this invention is inactivated means an embryonic stem cell (hereinafter to be briefly referred to as ES cell) of a non-human mammal, wherein the DNA does not substantially have the expression capability of the protein of this invention (hereinafter sometimes to be referred to as knockout DNA of the present invention), which is achieved by artificially introducing a mutation to the DNA of this invention possessed by the non-human mammal to suppress expression capability of DNA, or by substantially obliterating the activity of the protein of this invention that the DNA codes for.

As the non-human mammal, those similar to the aforementioned can be used.

As a method for artificially introducing a mutation to the DNA of the present invention, for example, a part or the entire DNA sequence can be deleted, or different DNA can be inserted or substituted by genetic engineering technique. With these mutations, a knockout DNA of this invention can be prepared, for example, by shifting the reading frame of codon or destroying the function of promoter or exon.

Specific examples of the non-human mammal embryonic stem cell where the DNA of this invention is inactivated (hereinafter to be briefly referred to as DNA-inactivated ES cell of this invention or knockout ES cell of this invention) can be obtained as follows. First, the DNA of this invention that the objective non-human mammal possesses is isolated, and a drug resistant gene represented by neomycin resistant gene and hygromycin resistant gene, a reporter gene represented by lacZ (β-galactosidase gene) and cat (chloramphenicol acetyl transferase gene) or the like is inserted into the exon portion of the DNA to destroy its function, or a DNA sequence (e.g., poly A-adding signal and the like) that terminates transcription of gene into an intron portion between the exons, in order to construct a DNA chain (hereinafter to be briefly referred to as targeting vector) having a DNA sequence constructed to consequently destroy gene by preventing synthesis of complete messenger RNA. Then, the DNA chain is transferred into the chromosome of the animal by, for example, homologous recombination. The knockout ES cell of the present invention is selected by analyzing the obtained ES cell by southern hybridization analysis using the DNA sequence on the DNA of this invention or in the vicinity thereof as a probe, or by PCR using the DNA sequence on a targeting vector, and a DNA sequence in the vicinity of the DNA that is other than the DNA of the present invention and is used for preparation of the targeting vector, as primers.

The original ES cell in which the DNA of this invention is inactivated by homologous recombination and the like, may be already established one as aforementioned, or even a new ES cell established according to the known method of Evans and Kaufma. For example, in the case of mouse ES cell, ES cell of 129 strain is generally used at present. However, since the immunological background of the cell of 129 strain is unclear, the ES cell which is established by the use of C57BL/6 mouse, BDF1 mouse (F1 of C57BL/6 and DBA/2) that has been established by crossing C57BL/6 with DBA/2 to increase the number of eggs obtained from C57BL/6, and the like can be also alternatively used, with the aim of obtaining an ES cell from pure strain and having clear immunologically and genetic background, and the like. BDF1 mouse advantageously produces many eggs that are strong, and in addition, it is derived from C57BL/6 mouse. Therefore, when a pathological model mouse is created from ES cell obtained from the BDF1 mouse, it is advantageous that the genetic background of the BDF1 mouse can be changed to that of C57BL/6 mouse by backcrossing with C57BL/6 mouse.

For the establishment of ES cell, blastocyst at day 3.5 after fertilization is generally used. In addition, many early embryos can be efficiently obtained by getting an 8 cell embryo and cultivating it up to blastocyst.

While either male or female ES cell can be used, generally, male ES cell is more convenient for creating a chimera of germ line than a female one. For eliminating complicated cultivation procedure, moreover, it is desirable to judge the sexuality of the cell as early as possible.

A method for judging sexuality of ES cells comprises, for example, a method comprising amplifying and detecting a gene in the sex determining region on Y chromosome by PCR. Using this method, the number of ES cells as small as one colony (about 50) is enough for karyotype analysis, though conventional method required about $10^6$ cells. Thus, primary selection of ES cells in the early stage of cultivation can be made based on judgment of sexuality. The selection of male cells in the early stage drastically reduces labor in the early stage of the cultivation.

The secondary selection can be made by, for example, confirmation of the number of chromosomes by G-binding method and the like. Although the number of chromosomes in the obtained ES cells is desirably 100% of the normal number, if it is difficult to achieve 100% due to physiological manipulation for establishment and the like, the gene of ES cell is desirably re-cloned into a normal cell (e.g., cell wherein number of chromosome is 2n=40 for mouse) after the knocking out.

Although the embryonic stem cell line obtained in this manner generally shows highly superior proliferation performance, careful subculture thereof is necessary, because it easily loses the ability of ontogeny. For example, the cell is cultivated according to a method comprising cultivation on a suitable feeder cell such as STO fibroblast in the presence of LIF (1-10000 U/ml) in a $CO_2$ culture vessel (preferably 5% $CO_2$, 95% air or 5% oxygen, 5% $CO_2$, 90% air) at about 37° C., or other method, and for subculture, for example, a method is employed which comprises a treatment with a trypsin/EDTA solution (generally 0.001-0.5% trypsin/0.1-5 mM EDTA, preferably about 0.1% trypsin/1 mM EDTA) to give a single cell, and seeded on a newly prepared feeder cell, and the like. Such subculture is done generally every 1 to 3 days. On this occasion, the cells are observed and when a morphologically abnormal cell is found, the cultivated cell is desirably discarded.

ES cells can be differentiated to various types of cells of, for example, vertex muscle, visceral muscle, cardiac muscle and the like by single layer cultivation until they reach high density or by float cultivation until cell agglomeration is formed under suitable conditions [M. J. Evans and M. H. Kaufman, Nature, vol. 292, p. 154 (1981); G. R. Martin, Proc. Natl. Acad. Sci. U.S.A., vol. 78, p. 7634 (1981); T. C. Doetschman et. al., Journal of Embryology and Experimental Morphology, vol. 87, p. 27 (1985)]. The cell deficient in expression of the DNA of the present invention, which is obtained by differentiating the ES cell of the present invention, is useful for the protein of this invention or cell biological investigation of the protein of this invention in vitro.

Non-human mammal deficient in expression of the DNA of this invention can be distinguished from normal animals by measuring and indirectly comparing the expression level of the mRNA of said animal by a publicly known method.

As the non-human mammal, those similar to the aforementioned can be used.

The non-human mammal which is deficient in the expression of DNA of the present invention can be produced as follows. For example, a targeting vector prepared as mentioned above is introduced into a mouse embryonic stem cell or mouse ovum, and as a result of the introduction, a DNA sequence in the targeting vector in which the DNA of this invention is inactivated, is replaced with the DNA of this invention on the chromosome of the mouse embryonic stem cell or mouse ovum, by homologous recombination, whereby the DNA of this invention can be knocked out.

Since many recombinations in mammal are non-homologous, examples of screening means for cells which have homologous recombinant include, for example, a method which comprises constructing targeting vector comprising the DNA of the present invention in which drug-resistant gene such as neomycin-resistant gene is inserted and thymidine kinase(tk) gene in the vicinity of the DNA of the present invention, and introducing the vector into embryonic stem cells or oocytes, and selecting surviving cells in the presence of the drug corresponding to the inserted drug-resistant gene (e.g., G418 for neomycin resistant gene, etc.) and ganciclovir. That is, if insertion mutant DNA of the present invention is incorporated into the chromosome by the homologous recombination, it is ganciclovir-resistant since tk gene is excluded, but in the case of incorporation by non-homologous recombination, it is ganciclovir-sensitive since tk gene is incorporated at the same time. Furthermore, if diphtheria toxin gene, etc. is used instead of tk gene, it is possible to select with a single drug since random-inserted cells are perished by the toxin production.

The cell wherein the DNA of this invention is knocked out can be judged by southern hybridization analysis using a DNA sequence on the DNA of this invention or in the vicinity thereof as a probe, or by PCR using, as primers, the DNA sequence on a targeting vector and a DNA sequence in the vicinity that is other than the DNA of the present invention derived from mouse and was used as the targeting vector.

When a non-human mammal embryonic stem cell is used, a cell line wherein the DNA of this invention is inactivated by gene homologous recombination is cloned, and the cells are injected at a suitable stage, for example, into 8 cell embryo or blastocyst of non-human mammal, and the chimeric embryo prepared is transplanted into the uterus of the pseudopregnant non-human mammal. The created animal is a chimeric animal consisting of cells having a normal locus of the DNA of the present invention and cells having locus of artificially mutated DNA of the present invention.

When part of the germ cells of the chimeric animal has the locus of mutant DNA of the present invention, such chimeric individual and a normal individual are mated to give individual group, from which an individual whose entire tissues consist of cells having the locus of DNA of the present invention in which artificial mutation was added, can be obtained by, for example, judgment of coat color and the like. The thus-obtained individual is generally a heterozygote which is deficient in the expression of the protein of this invention. The heterozygotes, which is deficient in the expression of the protein of this invention are mated each other and the homozygote which is deficient in the expression of the protein of this invention, can be obtained from their offspring.

When an ovum is used, for example, a transgenic non-human mammal incorporating a targeting vector in chromosome can be obtained by injecting a DNA solution into an ovum nucleus by a microinjection method, and selecting one that has a mutation in the locus of DNA of this invention by gene homologous recombination, as compared to such transgenic non-human mammal.

An individual in which the DNA of this invention is knocked-out can be bred over generations in ordinary breeding environment, upon confirmation of knocked-out of said DNA in the individual animal obtained by mating.

Moreover, establishment and maintenance of germ line can be performed by following the conventional methods. That is, a homozygote animal having said inactivated DNA in both the homologous chromosomes can be obtained by mating male and female animal retaining said inactivated DNA. The homozygote animal thus obtained can be reproduced efficiently by breeding in the state where normal individual is 1 and homozygote are plural relative to a mother animal. By mating male and female heterozygote animals, homozygote and heterozygote animals having said inactivated DNA can be bred over generations.

Non-human mammal embryonic stem cell wherein the DNA of this invention is inactivated is highly useful for creating the non-human mammal deficient in expression of DNA of the present invention.

In addition, the non-human mammal deficient in expression of the DNA of this invention lacks various biological activities that can be induced by the protein of this invention. Since it can be a model of the disease caused by inactivation of the biological activity of the protein of this invention, it is useful for the investigation of the cause of such disease and consideration of the treatment methods.

(14a) A Method for Screening of Compounds Having Therapeutic and/or Prophylactic Effects for Diseases Caused by Deficiency, Damages, Etc. of the DNA of the Present Invention The non-human mammal deficient in expression of the DNA of the present invention can be used to screen the compounds having therapeutic and/or prophylactic effects for diseases caused by deficiency, damages, and the like of the DNA of the present invention.

That is, the present invention provides a method for screening of a compound or salt thereof having therapeutic and/or prophylactic effects for diseases caused by deficiency, damages, etc. of the DNA of the present invention which comprises administering a test compound to the non-human mammal deficient in expression of the DNA of the present invention, and observing and measuring a change occurred in the animal.

As the non-human mammal deficient in expression of the DNA of the present invention used for the screening method, the same examples as given hereinabove can be used.

Examples of the test compounds include, for example, peptides, proteins, non-peptide compounds, synthetic compounds, fermentation products, cell extracts, vegetable extracts, animal tissue extracts, blood plasma, etc. and these compounds may be novel compounds or per se known compounds.

Specifically, the non-human mammal deficient in the expression of the DNA of the present invention is treated with a test compound, comparison is made with an untreated animal for control and a change in each organ, tissue, disease conditions, etc. of the animal is used as an indicator to assess the therapeutic and/or prophylactic effects of the test compound.

For treating a test animal with a test compound, for example, oral administration, intravenous injection, etc. can be applied and the treatment can be appropriately selected depending upon conditions of the test animal, properties of the test compound, etc. Furthermore, the amount of a test compound administered can be appropriately selected depending on administration route, nature of the test compound, or the like.

In the screening method, when a test compound is administered to a test animal, the test compound can be selected as a compound having the prophylactic and/or therapeutic effect against the above-mentioned diseases if the blood glucose value of the test animal reduced about 10% or more, preferably about 30% or more, more preferably about 50% or more.

The compound obtained using the screening methods is a compound selected from the test compounds described above and can be used as safe and less toxic medicines such as a therapeutic and/or prophylactic agent for the diseases caused by deficiencies, damages, etc. of the protein of the present invention, for example, diseases involving abnormality of adipocyte differentiation and/or metabolism function (e.g., obesity, diabetes, impaired glucose tolerance, arteriosclerosis, hypertension, hyperlipidemia, etc.). Furthermore, compounds derived from such a compound obtained by the above screening can be used as well.

The compound obtained by the screening method may be in the form of salts. As the salts of the compound, there may be used salts with physiologically acceptable acids (e.g., inorganic acids, organic acids, etc.) or bases (e.g., alkali metal, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A medicine comprising the compound or salts thereof obtained by the screening methods can be formulated in the same manner as in "the prophylactic and/or therapeutic agent for diseases associated with dysfunction of the protein of the present invention".

Since the preparation thus obtained is safe and less toxic, it can be administered to mammals (e.g., human, rats, mice, guinea pigs, rabbits, sheep, pigs, bovines, horses, cats, dogs, monkeys, etc.).

The dose of the compound or a salt thereof varies depending on target disease, the subject to be administered, route for administration, etc.; for example, in oral administration of the compound, the dose is normally about 0.1 mg to about 100 mg, preferably about 1.0 to about 50 mg, and more preferably about 1.0 to about 20 mg per day for a patient having abnormal glucose and/or lipid metabolism (as 60 kg body weight). In parenteral administration, a single dose varies depending on the subject to be administered, the subject organ, symptoms, administration method, etc.; for example, in injectable form, the dose is normally about 0.01 to about 30 mg, preferably about 0.1 to about 20 mg, and more preferably about 0.1 to about 10 mg per day for a patient having abnormal glucose and/or lipid metabolism (as 60 kg body weight). For other animal species other than human, the corresponding dose as converted per 60 kg body weight can be administered.

(14b) A Method of Screening a Compound that Promotes or Inhibits the Activities of a Promoter to the DNA of the Present Invention The present invention provides a method of screening a compound or salt thereof that promotes or inhibits the activities of a promoter to the DNA of the present invention, which comprises administering a test compound to a non-human mammal deficient in expression of the DNA of the present invention and detecting expression of the reporter gene.

In the screening method described above, the non-human mammal deficient in expression of the DNA of the present invention is selected from the above-mentioned non-human mammal deficient in expression of the DNA of the present invention for an animal, in which the DNA of the present invention is inactivated by introducing a reporter gene and the reporter gene can be expressed under control of a promoter to the DNA of the present invention.

The same examples given above for the test compound apply to the test compound.

As the reporter gene, the same specific examples given above apply to the reporter gene, with β-galactosidase (lacZ), soluble alkaline phosphatase gene, luciferase gene, etc. being preferred.

In the non-human mammal deficient in expression of the DNA of the present invention wherein the DNA of the present invention is substituted with a reporter gene, the reporter gene is present under control of a promoter to the DNA of the present invention. Thus, the activity of the promoter can be detected by tracing the expression of a substance encoded by the reporter gene.

For example, when a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, in place of the protein of the present invention. Thus, the in vivo expression state of the protein of the present invention can be readily observed in an animal, by staining with a reagent, e.g., 5-bromo-4-chloro-3-indolyl-β-galactopyranoside (X-gal), which is a substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue sample with 1 mM EDTA/PBS solution, the developed color is observed. Alternatively, mRNA encoding lacZ may be detected in a conventional manner.

The compound or salts thereof obtained using the screening methods described above are compounds selected from the test compounds described above, which promote or inhibit the promoter activity for the DNA of the present invention.

The compound obtained by the screening methods may be in the form of salts. The salts of the compound are salts with physiologically acceptable acids (e.g., inorganic acids, etc.) or bases (e.g., organic acids, etc.), and physiologically acceptable acid addition salts are preferred. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Since the compounds or salts thereof that promote the promoter activity to the DNA of the present invention can promote the expression of the protein of the present invention, or can promote the functions of the protein, they are useful as medicines such as prophylactic and/or therapeutic agents for diseases associated with dysfunction of the protein of the present invention.

Since the compounds or salts thereof that inhibit the promoter activity to the DNA of the present invention can inhibit the expression of the protein of the present invention, and can inhibit the functions of the protein, they are useful as medicines such as prophylactic and/or therapeutic agents for diseases associated with overexpression of the protein of the present invention.

The diseases associated with dysfunction or overexpression of the protein of the present invention includes, for example, diseases involving abnormality of adipocyte differentiation and/or metabolism function (e.g., obesity, diabetes, impaired glucose tolerance, arteriosclerosis, hypertension, hyperlipidemia, etc.), etc.

In addition, compound derived from the compounds obtained by the screening method above may be employed as well.

A medicine containing the compounds or salts thereof obtained by the screening methods described above may be prepared in a manner similar to the method for preparing the medicine comprising the compound changing binding property between the protein of the present invention and its ligands (or receptor).

Since the preparation thus obtained is safe and less toxic, it can be administered to mammals (e.g., human, rats, mice, guinea pigs, rabbits, sheep, pigs, bovines, horses, cats, dogs, monkeys, etc.).

The dose of the compound or a salt thereof varies depending on target disease, the subject to be administered, route for administration, etc.; for example, if a compound or salt thereof that promotes or inhibits the activities of a promoter to the DNA of the present invention is administered orally, the dose is normally about 0.1 mg to about 100 mg, preferably about 1.0 to about 50 mg, and more preferably about 1.0 to about 20 mg per day for a patient having abnormal glucose and/or lipid metabolism (as 60 kg body weight). In parenteral administration, a single dose varies depending on the subject to be administered, the subject organ, symptoms, administration method, etc.; for example, in injectable form, the dose is normally about 0.01 to about 30 mg, preferably about 0.1 to about 20 mg, and more preferably about 0.1 to about 10 mg per day for a patient having abnormal glucose and/or lipid metabolism (as 60 kg body weight). For other animal species other than human, the corresponding dose as converted per 60 kg body weight can be administered.

As described above, the non-human mammal deficient in expression of the DNA of the present invention is extremely useful for screening a compound or salt thereof that promotes or inhibits the promoter activity to the DNA of the present invention. Therefore, it can greatly contribute for searching causes of, or developing prophylactic and/or therapeutic agents for various diseases caused by deficiency in expression of the DNA of the present invention.

Further, where so-called transgenic animal (gene-introduced animal) is prepared by using DNA, which contains a promoter region for the protein of the present invention, ligating genes encoding a variety of proteins to downstream thereof and injecting this DNA to animal's egg cell, the protein can be synthesized specifically, so that it will allow to investigate its intravital function. Furthermore, where the cell line expressing an appropriate reporter gene, which binds to the above-mentioned promoter region, leads to establish, it can be used as a screening system of low molecular weight compound having a function that specifically promotes or inhibits intravital producing ability of the protein of the present invention itself.

In the description and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediamine tetraacetic acid
SDS: sodium dodecyl sulfate Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
pGlu: pyroglutamic acid
Me: methyl group
Et: ethyl group
Bu: butyl group
Ph: phenyl group
TC: thiazolidin-4(R)-carboxamide group Furthermore, substituent group, protecting group and reagents which are often used in the present specification are denoted as follows.
Tos: p-toluenesulfonyl
CHO: formyl
Bzl: benzyl
Cl$_2$Bzl: 2,6-dichlorobenzyl
Bom: benzyloxymethyl
Z: benzyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenyl methoxycarbonyl
HOBt: 1-hydroxybenztriazole
HOOBt: 3,4-dihydro-3-hydroxy-4-oxo-1,2,3-benztriazine
HONB: 1-hydroxy-5-norbornene-2,3-dicarboximide
DCC: N,N'-dicyclohexylcarbodiimido The sequence identification numbers in the sequence listing of the description indicates the following sequence, respectively.

[SEQ ID NO: 1]
This represents the base sequence of cDNA encoding mouse white adipose tissue-derived secretory or membrane protein mSST20-14 (Long form).

[SEQ ID NO: 2]
This represents the amino acid sequence of mouse white adipose tissue-derived secretory or membrane protein mSST20-14 (Long form).

[SEQ ID NO: 3]
This represents the base sequence of cDNA encoding mouse white adipose tissue-derived secretory or membrane protein mSST20-14 (Short form).

[SEQ ID NO: 4]
This represents the amino acid sequence of mouse white adipose tissue-derived secretory or membrane protein mSST20-14 (Short form).

[SEQ ID NO: 5]
This represents the base sequence of cDNA encoding mouse white adipose tissue-derived secretory or membrane protein mSST22-22 (Long form).

[SEQ ID NO: 6]
This represents the amino acid sequence of mouse white adipose tissue-derived secretory or membrane protein mSST22-22 (Long form).

[SEQ ID NO: 7]
This represents the base sequence of cDNA encoding mouse white adipose tissue-derived secretory or membrane protein mSST22-22 (Short form).

[SEQ ID NO: 8]
This represents the amino acid sequence of mouse white adipose tissue-derived secretory or membrane protein mSST22-22 (Short form).

[SEQ ID NO: 9]
This represents the base sequence of cDNA encoding mouse white adipose tissue-derived secretory or membrane protein mSST8-5.

[SEQ ID NO: 10]
This represents the amino acid sequence of mouse white adipose tissue-derived secretory or membrane protein mSST8-5.

[SEQ ID NO: 11]
This represents the base sequence of cDNA encoding mouse white adipose tissue-derived secretory or membrane protein mSST19-15 (Long form).

[SEQ ID NO: 12]
This represents the amino acid sequence of mouse white adipose tissue-derived secretory or membrane protein mSST19-15 (Long form).

[SEQ ID NO: 13]
This represents the base sequence of cDNA encoding mouse white adipose tissue-derived secretory or membrane protein mSST19-15 (Short form).

[SEQ ID NO: 14]
This represents the amino acid sequence of mouse white adipose tissue-derived secretory or membrane protein mSST19-15 (Short form).

[SEQ ID NO: 15]
This represents the base sequence of cDNA encoding mouse white adipose tissue-derived secretory or membrane protein mSST13-11.

[SEQ ID NO: 16]
This represents the amino acid sequence of mouse white adipose tissue-derived secretory or membrane protein mSST13-11.

[SEQ ID NO: 17]
This represents the base sequence of cDNA encoding mouse white adipose tissue-derived secretory or membrane protein mSST9-8.

[SEQ ID NO: 18]
This represents the amino acid sequence of mouse white adipose tissue-derived secretory or membrane protein mSST9-8.

[SEQ ID NO: 19]
This represents the base sequence of cDNA encoding mouse white adipose tissue-derived secretory or membrane protein mSST21-3.

[SEQ ID NO: 20]
This represents the amino acid sequence of mouse white adipose tissue-derived secretory or membrane protein mSST21-3.

[SEQ ID NO: 21]

This represents the base sequence of cDNA encoding mouse white adipose tissue-derived secretory or membrane protein mSST20-6.

[SEQ ID NO: 22]

This represents the amino acid sequence of mouse white adipose tissue-derived secretory or membrane protein mSST20-6.

[SEQ ID NO: 23]

This represents the base sequence of mouse white adipose tissue-derived secretory or membrane protein cDNA fragment mSst20-14 (partial).

[SEQ ID NO: 24]

This represents the base sequence of mouse white adipose tissue-derived secretory or membrane protein cDNA fragment mSst22-22 (partial).

[SEQ ID NO: 25]

This represents the base sequence of mouse white adipose tissue-derived secretory or membrane protein cDNA fragment mSst8-5 (partial).

[SEQ ID NO: 26]

This represents the base sequence of mouse white adipose tissue-derived secretory or membrane protein cDNA fragment mSst19-15 (partial).

[SEQ ID NO: 27]

This represents the base sequence of mouse white adipose tissue-derived secretory or membrane protein cDNA fragment mSst13-11 (partial).

[SEQ ID NO: 28]

This represents the base sequence of mouse white adipose tissue-derived secretory or membrane protein cDNA fragment mSst9-8 (partial).

[SEQ ID NO: 29]

This represents the base sequence of mouse white adipose tissue-derived secretory or membrane protein cDNA fragment mSst21-3 (partial).

[SEQ ID NO: 30]

This represents the base sequence of mouse white adipose tissue-derived secretory or membrane protein cDNA fragment mSst20-6 (partial).

[SEQ ID NO: 31]

This represents the base sequence of the primer for amplifying mouse white adipose tissue-derived secretory or membrane protein cDNA fragment.

[SEQ ID NO: 32]

This represents the base sequence of the primer for amplifying mouse white adipose tissue-derived secretory or membrane protein cDNA fragment.

[SEQ ID NO: 33]

This represents the base sequence of the gene-specific primer for 5'-RACE to identify full length base sequence encoding mouse white adipose tissue-derived secretory or membrane protein mSST20-14.

[SEQ ID NO: 34]

This represents the base sequence of the gene-specific primer for 3'-RACE to identify full length base sequence encoding mouse white adipose tissue-derived secretory or membrane protein mSST20-14.

[SEQ ID NO: 35]

This represents the base sequence of the gene-specific primer for 5'-RACE to identify full length base sequence encoding mouse white adipose tissue-derived secretory or membrane protein mSST22-22.

[SEQ ID NO: 36]

This represents the base sequence of the gene-specific primer for 3'-RACE to identify full length base sequence encoding mouse white adipose tissue-derived secretory or membrane protein mSST22-22.

[SEQ ID NO: 37]

This represents the base sequence of the gene-specific primer for 5'-RACE to identify full length base sequence encoding mouse white adipose tissue-derived secretory or membrane protein mSST8-5.

[SEQ ID NO: 38]

This represents the base sequence of the gene-specific primer for 3'-RACE to identify full length base sequence encoding mouse white adipose tissue-derived secretory or membrane protein mSST8-5.

[SEQ ID NO: 39]

This represents the base sequence of the gene-specific primer for 5'-RACE to identify full length base sequence encoding mouse white adipose tissue-derived secretory or membrane protein mSST19-15.

[SEQ ID NO: 40]

This represents the base sequence of the gene-specific primer for 3'-RACE to identify full length base sequence encoding mouse white adipose tissue-derived secretory or membrane protein mSST19-15.

[SEQ ID NO: 41]

This represents the base sequence of the gene-specific primer for 5'-RACE to identify full length base sequence encoding mouse white adipose tissue-derived secretory or membrane protein mSST13-11.

[SEQ ID NO: 42]

This represents the base sequence of the gene-specific primer for 3'-RACE to identify full length base sequence encoding mouse white adipose tissue-derived secretory or membrane protein mSST13-11.

[SEQ ID NO: 43]

This represents the base sequence of the gene-specific primer for 5'-RACE to identify full length base sequence encoding mouse white adipose tissue-derived secretory or membrane protein mSST9-8.

[SEQ ID NO: 44]

This represents the base sequence of the gene-specific primer for 3'-RACE to identify full length base sequence encoding mouse white adipose tissue-derived secretory or membrane protein mSST9-8.

[SEQ ID NO: 45]

This represents the base sequence of the gene-specific primer for 5'-RACE to identify full length base sequence encoding mouse white adipose tissue-derived secretory or membrane protein mSST21-3.

[SEQ ID NO: 46]

This represents the base sequence of the gene-specific primer for 3'-RACE to identify full length base sequence encoding mouse white adipose tissue-derived secretory or membrane protein mSST21-3.

[SEQ ID NO: 47]

This represents the base sequence of the gene-specific primer for 5'-RACE to identify full length base sequence encoding mouse white adipose tissue-derived secretory or membrane protein mSST20-6.

[SEQ ID NO: 48]

This represents the base sequence of the gene-specific primer for 3'-RACE to identify full length base sequence encoding mouse white adipose tissue-derived secretory or membrane protein mSST20-6.

Hereinafter, the present invention will be described in more detail using Examples, but these are not deemed to limit the scope of the invention. Gene manipulation using *Escherichia coli* was done according to a method described in Molecular cloning (described above).

EXAMPLE 1

Screening of Secretory or Membrane Protein cDNA Derived from Mouse White Adipose Tissue Mouse proB cell strain Ba/F3 (RIKEN Cell Bank; RCB0805) requires IL-3 for its survival and/or growth. The cell expresses thrombopoietin receptor (MPL) on the cell membrane and forms homo-dimer by binding thrombopoietin which is a ligand, into which growth signal is transducted. It has been found that MPL becomes ligand-independent constitutive active form ($MPL^M$) by $Ser^{498}Asn$ mutation in the transmembrane region, survival and/or growth of Ba/F3 is maintained in the absence of IL-3, but activity of $MPL^M$ is not necessary for most of extracellular domain, and if 187 amino acids of C-terminus is included, it is expressed on the cell membrane to form homo-dimer (Kojima and Kitamura, described above). That is, if retrovirus vector designed that cDNA is incorporated into 5' side of $MPL^M$ of which extracellular region is deleted is constructed, and the incorporated cDNA has a signal sequence, fusion protein of cDNA encoded protein and $MPL^M$ is expressed on the cell membrane of Ba/F3 and the Ba/F3 can survive and/or grow independent of IL-3. On the basis of these principles, cDNA derived from mouse white adipose tissue loaded by high fat food was inserted into BstXI site of retrovirus vector comprising code region ($\Delta MPL^M$) of $MPL^M$ in which $Met^1$ to $Thr^{441}$ are deleted (pMX-SST; Kojima and Kitamura, described above) to construct retrovirus expression library, and cloning of secretory or membrane protein cDNA was performed.

First, visceral adipose tissue (white adipose around mesentery and epididymis) was excised from high fat food-loaded mouse (30% high fat food was given to C57B1/6J, 12 weeks old, male for 12 days), poly A(+) RNA was isolated with Quick Prep mRNA Purification Kit (Pharmacia) according to the protocols attached, and converted into cDNA by random hexamer using SuperScript Choice System (Gibco-BRL). Obtained cDNA was inserted into BstXI site of retrovirus vector pMX-SST using BstXI adaptor (Invitrogen), and the cDNA was ligated to 5' side of $MPL^M$. Obtained DNA was introduced into *E. coli* DH10B strain using electroporation method, and amplified. Plasmid DNA was purified according to a conventional method, and transfected into packaging cell for constructing retrovirus (Plat-E; Morita et al., Gene Ther., 7(12): 1063-1066, 2000; acquired from Doctor Toshio Kitamura, the Institute of Medical Science, the University of Tokyo) ($2\times10^6$ cell/dish) using Lipofectamine™ reagents (Invitrogen) according to the protocols attached. After incubation on DMEM medium containing 10% fetal bovine serum for 24 hours, the medium was exchanged to a fresh medium, incubated for 24 hours and the culture supernatant was gathered to give high titer retrovirus stock having infectability (infection efficiency 10-30%). Cells for protein expression (Ba/F3) were infected with this retrovirus stock, incubated on RPMI1640 medium containing IL-3 for 1 day, inoculated into 96-well plate at $1\times10^4$/well, and selected on IL-3 free medium. Ba/F3 maintaining growing property after infection was selected, and genome DNA was extracted therefrom by a conventional method. Then, PCR was performed using the oligonucleotides represented by SEQ ID NO 31 and 32 as a primer and the genome DNA as a template (98° C., 60 seconds, followed by 98° C., 20 seconds and then 68° C., 120 seconds; 30 cycles). The amplified fragment was subcloned to pENTR/D-topo (Invitrogen, trademark). The base sequence of each cDNA insert was sequenced using BigDye Terminator Cycle Sequencing FS Ready Kit (PE Biosystems) and DNA automatic sequencer (ABI Prism 377), and as results, eight novel cDNA clones (Sst20-6, Sst22-22, Sst9-8, Sst13-11, Sst19-15, Sst20-14, Sst21-3 and Sst8-5) were identified.

*Escherichia coli* competent cell *Escherichia coli* Top10 (Invitrogen) was transformed with plasmids pENTR/D-TOPO (20-6), pENTR/D-TOPO (22-22), pENTR/D-TOPO (9-8), pENTR/D-TOPO (13-11), pENTR/D-TOPO (19-15), pENTR/D-TOPO (20-14), pENTR/D-TOPO (21-3) and pENTR/D-TOPO (8-5) into which the above-mentioned eight kinds of cDNA clone were inserted, respectively, to give transformants *Escherichia coli* Top10/pENTR/D-TOPO (20-6), *Escherichia coli* Top10/pENTR/D-TOPO (22-22), *Escherichia coli* Top10/pENTR/D-TOPO (9-8), *Escherichia coli* Top10/pENTR/D-TOPO (13-11), *Escherichia coli* Top10/pENTR/D-TOPO (19-15), *Escherichia coli* Top10/pENTR/D-TOPO (20-14), *Escherichia coli* Top10/pENTR/D-TOPO (21-3) and *Escherichia coli* Top10/pENTR/D-TOPO (8-5) strain. These *Escherichia coli* strains have been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566) under the accession number of FERM BP-8106, FERM BP-8109, FERM BP-8105, FERM BP-8107, FERM BP-8108, FERM BP-8104, FERM BP-8102 and FERM BP-8110, respectively on Jul. 2, 2002.

EXAMPLE 2

Analysis of Expression of Novel Secretory or Membrane Protein Gene

Expression states of such genes were investigated under various conditions using the novel cDNAs obtained in Example 1 as probe by Northern blot analysis.

First, expression in white adipose tissue and specificity of expression tissue were analyzed. As a result, Sst20-14 showed expression specific for white adipose tissue. On the other hand, Sst21-3, Sst13-11, Sst9-8 and Sst19-15 were identified to show expression also in brown adipose tissue.

Sst13-11 had increased expression amount in high fat-high sucrose loaded mouse in comparison with control mouse. It also had increased expression amount in obesity model mouse ob/ob in comparison with control C57b16/J mouse.

Sst21-3 had increased expression amount in diabetes model mouse db/db in comparison with control C57b16/J mouse. Expressions in 3T3-L1 cell which can differentiate into white adipose were also investigated, and as results, Sst21-3 was also expressed in undifferentiated precursor adipocyte.

Sst20-14 had a motif which can bind to lipid of lipoprotein in the obtained clone fragment.

Furthermore, Sst20-14, Sst19-15, Sst13-11 and Sst21-3 was decreased in expression amount by fasting, and elevated (recovered) by re-feeding following fasting.

EXAMPLE 3

Cloning of Full Length cDNA

Gene-specific primers for 5'-RACE (GSP1) and gene-specific primers for 3'-RACE (GSP2) were designed for eight cDNA fragments of the novel secretory or membrane proteins obtained in Example 1 (SEQ ID NOS. 33 and 34, respectively for Sst20-14; SEQ ID NOS. 35 and 36, respectively for Sst22-

22; SEQ ID NOS. 37 and 38, respectively for Sst8-5; SEQ ID NOS. 39 and 40, respectively for Sst19-15; SEQ ID NOS. 41 and 42, respectively for Sst13-11; SEQ ID NOS. 43 and 44, respectively for Sst9-8; SEQ ID NOS. 45 and 46 respectively for Sst21-3; SEQ ID NOS. 47 and 48, respectively for Sst20-6) on the basis of the sequenced each base sequence, and 5'-RACE and 3'-RACE reactions were performed using SMART™ RACE cDNA amplification kit (clontech). The experiment was performed according to the instructions attached of the kit. Total RNA was extracted from C57BL/6J mouse in the same manner as in Example 1, adaptor primer was added and reverse transcription reaction was performed to construct cDNA. PCR was performed using this cDNA as template under the following conditions (94° C. 5 sec, 72° C. 3 min=5 cycles, 94° C. 5 sec, 69° C. 10 sec, 72° C. 3 min=5 cycles, 94° C. 5 sec, 66° C. 10 sec, 72° C. 3 min=40 cycles). PCR product was separated with 1% agarose gel electrophoresis, obtained band was extracted by excision from gel, TA cloned into pCR4-TOPO or pENTR/D-TOPO (all, Invitrogen). The sequence of the insert DNA of the obtained plasmids was sequenced by a conventional method. As a result, any of the clones contained complete ORF. Two kinds of clones comprising ORFs of different length were obtained for Sst20-14, Sst22-22 and Sst19-15 (designated as Long form and Short form, respectively according to the length of ORF). *Escherichia coli* competent cell *Escherichia coli* Top10 (Invitrogen) was transformed with plasmids pCR4-TOPO (SST20-14 long form), pCR4-TOPO (SST20-14 short form), pCR4-TOPO (SST22-22 long form), pCR4-TOPO (SST22-22 short form), pCR4-TOPO (SST8-5), pCR4-TOPO (SST19-15 long form), pCR4-TOPO (SST19-15 short form), pCR4-TOPO (SST13-11), pENTR/D-TOPO (SST9-8), pCR4-TOPO (SST21-3) and pCR4-TOPO (SST20-6) into which these total eleven kinds of cDNA clones are inserted, respectively, to give transformants (1) *Escherichia coli* Top10/pCR4-TOPO (SST20-14 long form), (2) *Escherichia coli* Top10/pCR4-TOPO (SST20-14 short form), (3) *Escherichia coli* Top10/pCR4-TOPO (SST22-22 long form), (4) *Escherichia coli* Top10/pCR4-TOPO (SST22-22 short form), (5) *Escherichia coli* Top10/pCR4-TOPO (SST8-5), (6) *Escherichia coli* Top10/pCR4-TOPO (SST19-15 long form), (7) *Escherichia coli* Top10/pCR4-TOPO (SST19-15 short form), (8) *Escherichia coli* Top10/pCR4-TOPO (SST13-11), (9) *Escherichia coli* Top10/pENTR/D-TOPO(SST9-8), (10) *Escherichia coli* Top10/pCR4-TOPO (SST21-3) and (11) *Escherichia coli* Top10/pCR4-TOPO (SST20-6) strain. These *Escherichia coli* strains have been deposited with International Patent Organism Depositary (IPOD), National Institute of Advanced Industrial Science and Technology (AIST) at Central 6, 1-1-1, Higashi, Tsukuba, Ibaraki, Japan (zip code: 305-8566) under the accession number of FERM BP-8406, FERM BP-8407, FERM BP-8408, FERM BP-8409, FERM BP-8402, FERM BP-8404, FERM BP-8405, FERM BP-8403, FERM BP-8411, FERM BP-8413 and FERM BP-8412, respectively, on Jun. 20, 2003 for (1) to (8), and Jun. 24, 2003 for (9) to (11).

EXAMPLE 4

Analysis of Action for Differentiation of Preadipocyte Strain 3T3-L1 into Mature Adipocyte 3T3-L1 cell was inoculated into 6-well plate at $2\times10^5$ cells/well of cell number, and incubated on DMEM (Invitrogen) medium containing 10% fetal bovine serum (Invitrogen) at 37° C. for 7 days, incubation solution was suctioned, and the well was washed twice with PBS (Invitrogen), and then 2 ml/well of OPTI-MEM (Invitrogen) was added thereto. OPTI-MEM (100 μl) and FuGENE™6 (10 μl, Roche) were mixed and stood still at room temperature for 5 minutes. Thereto was added 21g of construct for expression pCMV-SST20-14 prepared by inserting SST20-14 (Long form) cDNA into EcoRI-HindIII cloning site of pCMV-Tag4A (Sigma) which is an expression plasmid, and the mixed solution was stood still at room temperature for 45 minutes. The solution containing the expression construct was added to the above-mentioned 3T3-L1 cell, and incubated at 37° C. for 6 hours, and then incubated on DMEM medium containing 10% fetal bovine serum at 37° C. for 40 hours. Then, the medium was exchanged to a differentiation medium [DMEM medium containing 250 nM dexamethasone (Sigma), 0.5 mM 1-methyl-3-isobutyl xanthine (Wako Pure Chemical Industries, Ltd.), 10 μg/ml insulin (Sigma) and 10% fetal bovine serum] and incubated for 72 hours. Then, the medium was further incubated on DMEM medium containing 10% fetal bovine serum for 8 days. After completing incubation, the incubation solution was suctioned, and the medium was washed twice with PBS. 2 ml of 10% formalin (Wako Pure Chemical Industries, Ltd.) was added to the medium, which was stood still for 30 minutes. After washing with distilled water twice, oil red-O solution was added and stained for 10 minutes. After washing twice with distilled water and air-drying, accumulation of lipid drop was investigated. As a result, 3T3-L1 cell overexpressing SST20-14 reduced in accumulation of lipid drop qualitatively reduced to a half or less as compared with control 3T3-L1 cell under microscopic observation, to confirm that it affected differentiation into mature adipocyte.

EXAMPLE 5

Analysis of Expression of Novel Secretory or Membrane Protein Gene by Insulin Resistance Inducing Factor 3T3-L1 cell was inoculated into 6-well plate at $4\times10^5$ cells/well of cell number and incubated on DMEM (Invitrogen) medium containing 10% fetal bovine serum (Invitrogen) at 37° C. for 5 days. The medium was exchanged to a differentiation medium [DMEM medium containing 250 nM dexamethasone (Sigma), 0.5 mM 1-methyl-3-isobutyl xanthine (Wako Pure Chemical Industries, Ltd.), 10 μg/ml insulin (Sigma) and 10% fetal bovine serum] and further incubated for 24 hours. In exchanging the medium to the differentiation medium, each of TNF-α (Genzyme Techne) at the concentration of 1 nM, 100 pM and 10 pM was added to the medium at the same time. After completing incubation, the medium was washed with PBS (Invitrogen), and the cells were collected. Total RNA was gathered from the collected cells using RNAeasy kit (Qiagen) according to the instructions attached to the kit. Using the gathered total RNA, expression amounts of SST20-14 and mRNA of 36B4 which is used as internal standard were quantified by TaqMan PCR (Applied Biosystems). As a result, the expression amount of SST20-14 changed depending on added TNF-α concentration, and expression amount of SST20-14 reduced about 70% as compared with control (TNF-α free) by addition of 1 nM TNF-α for 24 hours.

EXAMPLE 6

Analysis of Expression of Novel Secretory or Membrane Protein Gene by an Insulin Sensitizer 3T3-L1 cell was inoculated into 6-well plate at $4\times10^5$ cells/well of cell number and incubated on DMEM (Invitrogen) medium containing 10% fetal bovine serum (Invitrogen) at 37° C. for 5 days. The medium was exchanged to a differentiation medium [DMEM medium containing 250 nM dexamethasone (Sigma), 0.5 mM 1-methyl-3-isobutyl xanthine (Wako Pure Chemical Industries, Ltd.), 10 µg/ml insulin (Sigma) and 10% fetal bovine serum]. In exchanging the medium to the differentiation medium, pioglitazone hydrochloride (10 µM, Takeda Pharmaceutical Company, Ltd.) which is an insulin sensitizer was added to the medium, and incubated for 72 hours in the presence of insulin. After completing incubation, the medium was washed with PBS (Invitrogen), and the cells were collected. Total RNA was gathered from the collected cells using RNAeasy kit (Qiagen) according to the instructions attached to the kit. Using the gathered total RNA, expression amounts of SST8-5 and mRNA of 36B4 which is used as internal standard were quantified by TaqMan PCR (Applied Biosystems). As a result, the expression amount of SST8-5 increased 2.4-fold by addition of pioglitazone hydrochloride as compared with control (pioglitazone hydrochloride free).

INDUSTRIAL APPLICABILITY

Since the protein of the present invention is a secretory or membrane protein expressed in white adipocyte by loading high fat food, it exerts excellent effects as a prophylactic and/or therapeutic agent for diseases associated with abnormality of adipocyte differentiation or metabolism function, or tool for screening of a drug-candidate compound effective for prophylaxis and/or treatment of the diseases. Sequence List Free-text

[SEQ ID NO: 31]
Oligonucleotide designed to serve as a primer for amplifying mouse white adipocyte-derived secretory or membrane protein cDNA fragment.

[SEQ ID NO: 32]
Oligonucleotide designed to serve as a primer for amplifying mouse white adipocyte-derived secretory or membrane protein cDNA fragment.

[SEQ ID NO: 33]
Oligonucleotide designed to serve as gene-specific primer for 5'-RACE for identifying a full length base sequence encoding mSST20-14.

[SEQ ID NO: 34]
Oligonucleotide designed to serve as gene-specific primer for 3'-RACE for identifying a full length base sequence encoding mSST20-14.

[SEQ ID NO: 35]
Oligonucleotide designed to serve as gene-specific primer for 5'-RACE for identifying a full length base sequence encoding mSST22-22.

[SEQ ID NO: 36]
Oligonucleotide designed to serve as gene-specific primer for 3'-RACE for identifying a full length base sequence encoding mSST22-22.

[SEQ ID NO: 37]
Oligonucleotide designed to serve as gene-specific primer for 5'-RACE for identifying a full length base sequence encoding mSST8-5.

[SEQ ID NO: 38]
Oligonucleotide designed to serve as gene-specific primer for 3'-RACE for identifying a full length base sequence encoding mSST8-5.

[SEQ ID NO: 39]
Oligonucleotide designed to serve as gene-specific primer for 5'-RACE for identifying a full length base sequence encoding mSST19-15.

[SEQ ID NO: 40]
Oligonucleotide designed to serve as gene-specific primer for 3'-RACE for identifying a full length base sequence encoding mSST19-15.

[SEQ ID NO: 41]
Oligonucleotide designed to serve as gene-specific primer for 5'-RACE for identifying a full length base sequence encoding mSST13-11.

[SEQ ID NO: 42]
Oligonucleotide designed to serve as gene-specific primer for 3'-RACE for identifying a full length base sequence encoding mSST13-11.

[SEQ ID NO: 43]
Oligonucleotide designed to serve as gene-specific primer for 5'-RACE for identifying a full length base sequence encoding mSST9-8.

[SEQ ID NO: 44]
Oligonucleotide designed to serve as gene-specific primer for 3'-RACE for identifying a full length base sequence encoding mSST9-8.

[SEQ ID NO: 45]
Oligonucleotide designed to serve as gene-specific primer for 5'-RACE for identifying a full length base sequence encoding mSST21-3.

[SEQ ID NO: 46]
Oligonucleotide designed to serve as gene-specific primer for 3'-RACE for identifying a full length base sequence encoding mSST21-3.

[SEQ ID NO: 47]
Oligonucleotide designed to serve as gene-specific primer for 5'-RACE for identifying a full length base sequence encoding mSST20-6.

[SEQ ID NO: 48]
Oligonucleotide designed to serve as gene-specific primer for 3'-RACE for identifying a full length base sequence encoding mSST20-6.

The invention claimed is:

1. A method of reducing lipid accumulation in an adipocyte, which comprises contacting the adipocyte with a protein comprising the amino acid sequence of SEQ ID NO: 2 or a salt thereof, thereby reducing lipid accumulation in said adipocyte.

2. A method of reducing lipid accumulation in an adipocyte, which comprises transforming said adipocyte with a polynucleotide encoding a protein comprising the amino acid sequence of SEQ ID NO:2, thereby reducing lipid accumulation in said adipocyte.

* * * * *

UNITED STATES PATENT AND TRADEMARK OFFICE
CERTIFICATE OF CORRECTION

| | | |
|---|---|---|
| PATENT NO. | : 7,833,972 B2 | Page 1 of 1 |
| APPLICATION NO. | : 12/371525 | |
| DATED | : November 16, 2010 | |
| INVENTOR(S) | : Yuji Matsuzawa et al. | |

It is certified that error appears in the above-identified patent and that said Letters Patent is hereby corrected as shown below:

On the Title Page, Item (62), in the "Related U.S. Application Data", line 1, "filed as appli-" should read -- filed on Aug. 9, 2005, which is a National Stage of International Appli- --.

On the Title Page, Item (62), in the "Related U.S. Application Data", line 2, after "No. PCT/JP03/08690," insert -- filed --.

Signed and Sealed this
Twenty-second Day of February, 2011

David J. Kappos
*Director of the United States Patent and Trademark Office*

UNITED STATES PATENT AND TRADEMARK OFFICE
CERTIFICATE OF CORRECTION

PATENT NO. : 7,833,972 B2
APPLICATION NO. : 12/371525
DATED : November 16, 2010
INVENTOR(S) : Yuji Matsuzawa et al.

Page 1 of 1

It is certified that error appears in the above-identified patent and that said Letters Patent is hereby corrected as shown below:

On the Title Page, Item (73) Assignee, line 1, "Takeda Pharmaceutical Company Limited (JP)" should read -- Takeda Pharmaceutical Company Limited, Osaka (JP) --

Signed and Sealed this
Twenty-eighth Day of June, 2011

David J. Kappos
*Director of the United States Patent and Trademark Office*